United States Patent
Haines

(10) Patent No.: US 8,088,167 B2
(45) Date of Patent: *Jan. 3, 2012

(54) FEMORAL PROSTHETIC IMPLANT

(75) Inventor: Timothy G. Haines, Columbia City, IN (US)

(73) Assignee: Hudson Surgical Design, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/638,692

(22) Filed: Dec. 15, 2009

(65) Prior Publication Data
US 2010/0100192 A1 Apr. 22, 2010

Related U.S. Application Data

(63) Continuation of application No. 11/933,298, filed on Oct. 31, 2007, which is a continuation of application No. 10/756,817, filed on Jan. 13, 2004, now Pat. No. 7,344,541, which is a continuation of application No. 09/799,325, filed on Mar. 5, 2001, now Pat. No. 6,695,848.

(51) Int. Cl.
*A61F 2/38* (2006.01)

(52) U.S. Cl. ............... 623/20.35; 623/20.21; 623/20.31; 623/20.36

(58) Field of Classification Search ........................ None
See application file for complete search history.

(56) References Cited

U.S. PATENT DOCUMENTS

| | | |
|---|---|---|
| 2,697,433 A | 12/1954 | Zehnder |
| 3,457,922 A | 7/1969 | Ray |
| 3,739,662 A | 6/1973 | Windelman |
| 3,748,662 A | 7/1973 | Helfet |
| 3,774,244 A | 11/1973 | Walker |
| 3,798,679 A | 3/1974 | Ewald |
| 3,816,855 A | 6/1974 | Saleh |
| 3,906,550 A | 9/1975 | Rostoker |
| 3,943,934 A | 3/1976 | Bent |
| 3,953,899 A | 5/1976 | Charnley |
| 3,958,278 A | 5/1976 | Lee |
| 3,977,289 A | 8/1976 | Tuke |
| 4,016,606 A | 4/1977 | Murray |
| 4,069,824 A | 1/1978 | Weinstock |
| 4,178,641 A | 12/1979 | Gruendel |
| 4,207,627 A | 6/1980 | Cloutier |
| 4,213,209 A | 7/1980 | Insall |

(Continued)

FOREIGN PATENT DOCUMENTS

EP 0104732 4/1984

(Continued)

OTHER PUBLICATIONS

*Hudson Surgical Design v. Zimmer Holdings, Inc., et al.*, Zimmer, Inc.'s and Zimmer Holding Inc's Supplemental Responses to Hudson Surgical Design, Inc.'s First Set of Interrogatories (Nos. 1-18) To Each of Them, dated Aug. 1, 2008.

(Continued)

*Primary Examiner* — David H Willse
*Assistant Examiner* — Javier Blanco
(74) *Attorney, Agent, or Firm* — Patterson Thuente Christensen Pedersen, P.A.

(57) ABSTRACT

Methods and apparatus for knee arthroplasty, including implants, positioning and alignment guides, cutting guides, cutting tools and techniques for the femur and/or tibia.

33 Claims, 40 Drawing Sheets

U.S. PATENT DOCUMENTS

| | | |
|---|---|---|
| 4,249,270 A | 2/1981 | Bahler |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr |
| 4,567,886 A | 2/1986 | Petersen |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,703,751 A | 11/1987 | Pohl |
| 4,709,699 A | 12/1987 | Michael |
| 4,711,639 A | 12/1987 | Grundel |
| 4,714,472 A | 12/1987 | Averill |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,822,365 A | 4/1989 | Walker |
| 4,834,758 A | 5/1989 | Lane |
| 4,841,975 A | 6/1989 | Woolson |
| 4,880,429 A | 11/1989 | Stone |
| 4,892,093 A | 1/1990 | Zarnowski |
| 4,893,619 A | 1/1990 | Dale |
| 4,896,663 A | 1/1990 | Vandewalle |
| 4,919,667 A | 4/1990 | Richmond |
| 4,926,847 A | 5/1990 | Luckman |
| 4,935,023 A | 6/1990 | Whiteside |
| 4,936,853 A | 6/1990 | Fabian |
| 4,938,762 A | 7/1990 | Wehrli |
| 4,938,769 A | 7/1990 | Shaw |
| 4,944,757 A | 7/1990 | Martinez |
| 4,950,298 A | 8/1990 | Gustilo |
| 4,952,213 A | 8/1990 | Bowman |
| 4,963,152 A | 10/1990 | Hofmann |
| 4,971,075 A | 11/1990 | Lee |
| 4,979,949 A | 12/1990 | Matsen |
| 5,002,545 A | 3/1991 | Whiteside |
| 5,002,547 A | 3/1991 | Poggie |
| 5,007,933 A | 4/1991 | Sidebotham |
| 5,007,934 A | 4/1991 | Stone |
| 5,021,056 A | 6/1991 | Hofman |
| 5,021,061 A | 6/1991 | Wevers |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,062,852 A | 11/1991 | Dorr |
| 5,080,675 A | 1/1992 | Lawes |
| 5,092,869 A | 3/1992 | Waldron |
| 5,098,436 A | 3/1992 | Ferrante |
| 5,100,409 A | 3/1992 | Coates |
| 5,112,336 A | 5/1992 | Krevolin |
| 5,116,375 A | 5/1992 | Hofmann |
| 5,122,144 A | 6/1992 | Bert |
| 5,129,909 A | 7/1992 | Sutherland |
| 5,133,758 A | 7/1992 | Hollister |
| 5,133,759 A | 7/1992 | Turner |
| 5,147,365 A | 9/1992 | Whitlock |
| 5,147,405 A | 9/1992 | Van Zile |
| 5,176,710 A | 1/1993 | Hahn |
| 5,178,626 A | 1/1993 | Pappas |
| 5,190,547 A | 3/1993 | Barber, Jr. |
| 5,197,944 A | 3/1993 | Steele |
| 5,201,881 A | 4/1993 | Evans |
| 5,203,807 A | 4/1993 | Evans |
| 5,206,023 A | 4/1993 | Hunziker |
| 5,219,362 A | 6/1993 | Tuke |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,432 A | 8/1993 | Matsen |
| 5,236,461 A | 8/1993 | Forte |
| 5,236,875 A | 8/1993 | Trigg |
| 5,250,050 A | 10/1993 | Poggie |
| 5,263,498 A | 11/1993 | Caspari |
| 5,263,956 A | 11/1993 | Nobles |
| 5,269,786 A | 12/1993 | Morgan |
| 5,275,603 A | 1/1994 | Ferrante |
| 5,279,575 A | 1/1994 | Sugarbaker |
| 5,282,803 A | 2/1994 | Lackey |
| 5,282,867 A | 2/1994 | Mikhall |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,326,358 A | 7/1994 | Aubriot |
| 5,330,533 A | 7/1994 | Walker |
| 5,330,534 A | 7/1994 | Herrington |
| 5,342,368 A | 8/1994 | Peterson |
| 5,358,527 A | 10/1994 | Forte |
| 5,358,529 A | 10/1994 | Davidson |
| 5,358,531 A | 10/1994 | Goodfellows |
| 5,364,401 A | 11/1994 | Ferreante |
| 5,364,402 A | 11/1994 | Mumme |
| 5,370,699 A | 12/1994 | Hood |
| 5,370,701 A | 12/1994 | Finn |
| 5,391,170 A | 2/1995 | McGuire |
| 5,405,349 A | 4/1995 | Burkinshaw |
| 5,413,604 A | 5/1995 | Hodge |
| 5,415,663 A | 5/1995 | Luckman |
| 5,417,694 A | 5/1995 | Marik |
| 5,417,695 A | 5/1995 | Axelson |
| 5,443,464 A | 8/1995 | Russell |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,480,446 A | 1/1996 | Goodfellows |
| 5,514,136 A | 5/1996 | Richelsoph |
| 5,514,139 A | 5/1996 | Goldstein |
| 5,514,143 A | 5/1996 | Bonutti |
| 5,520,694 A | 5/1996 | Dance |
| 5,520,695 A | 5/1996 | Luckman |
| 5,540,695 A | 7/1996 | Levy |
| 5,542,947 A | 8/1996 | Treacy |
| 5,549,684 A | 8/1996 | Amino |
| 5,549,688 A | 8/1996 | Ries |
| 5,551,429 A | 9/1996 | Fitzpatrick |
| 5,562,674 A | 10/1996 | Stalcup |
| 5,569,262 A | 10/1996 | Carney |
| 5,571,100 A | 11/1996 | Goble |
| 5,578,039 A | 11/1996 | Vendrely |
| 5,593,411 A | 1/1997 | Stalcup |
| 5,597,379 A | 1/1997 | Haines |
| 5,601,563 A | 2/1997 | Burke |
| 5,601,566 A | 2/1997 | Dance |
| 5,609,645 A | 3/1997 | Vinciguerra |
| 5,611,802 A | 3/1997 | Samuelson |
| 5,613,969 A | 3/1997 | Jenkins |
| 5,628,749 A | 5/1997 | Vendrely |
| 5,639,279 A | 6/1997 | Burkinshaw |
| 5,643,272 A | 7/1997 | Haines |
| 5,649,928 A | 7/1997 | Grundei |
| 5,653,714 A | 8/1997 | Dietz |

| Patent No. | Date | Name |
|---|---|---|
| 5,658,293 A | 8/1997 | Vanlaningham |
| 5,667,511 A | 9/1997 | Vendrely |
| 5,681,354 A | 10/1997 | Eckhoff |
| 5,682,886 A | 11/1997 | Delp |
| 5,690,632 A | 11/1997 | Schwartz |
| 5,690,635 A | 11/1997 | Matsen, III |
| 5,690,637 A | 11/1997 | Wen |
| 5,697,935 A | 12/1997 | Moran et al. |
| 5,702,458 A | 12/1997 | Burstein |
| 5,723,016 A | 3/1998 | Minns |
| 5,725,530 A | 3/1998 | Popken |
| 5,728,162 A | 3/1998 | Eckhoff |
| 5,755,801 A | 5/1998 | Walker |
| 5,755,803 A | 5/1998 | Haines |
| 5,755,804 A | 5/1998 | Schmotzer |
| 5,766,257 A | 6/1998 | Goodman |
| 5,769,855 A | 6/1998 | Bertin |
| 5,769,899 A | 6/1998 | Schwartz |
| 5,776,200 A | 7/1998 | Johnson |
| 5,782,921 A | 7/1998 | Colleran |
| 5,782,925 A | 7/1998 | Collazo |
| 5,799,055 A | 8/1998 | Peshkin |
| 5,800,552 A | 9/1998 | Forte |
| 5,810,827 A | 9/1998 | Haines |
| 5,824,100 A | 10/1998 | Kester |
| 5,824,102 A | 10/1998 | Buscayret |
| 5,824,105 A | 10/1998 | Ries |
| 5,871,545 A | 2/1999 | Goodfellows |
| 5,871,546 A | 2/1999 | Colleran |
| 5,879,354 A | 3/1999 | Haines |
| 5,879,392 A | 3/1999 | McMinn |
| 5,906,643 A | 5/1999 | Walker |
| 5,908,424 A | 6/1999 | Bertin |
| 5,925,049 A | 7/1999 | Gustilo |
| 5,935,173 A | 8/1999 | Roger |
| 5,954,770 A | 9/1999 | Schmotzer |
| 5,980,526 A | 11/1999 | Johnson |
| 5,986,169 A | 11/1999 | Gjunter |
| 5,997,577 A | 12/1999 | Herrington |
| 6,039,764 A | 3/2000 | Pottenger |
| 6,056,754 A | 5/2000 | Haines |
| 6,059,788 A | 5/2000 | Katz |
| 6,068,658 A | 5/2000 | Insall |
| 6,080,195 A | 6/2000 | Colleran |
| 6,099,570 A | 8/2000 | Livet |
| 6,110,182 A | 8/2000 | Mowlai-Ashtiani |
| 6,120,543 A | 9/2000 | Kubein-Meesenburg |
| 6,132,468 A | 10/2000 | Mansmann |
| 6,139,581 A | 10/2000 | Engh |
| 6,165,223 A | 12/2000 | Metzger |
| 6,171,340 B1 | 1/2001 | McDowell |
| 6,195,577 B1 | 2/2001 | Truwit |
| 6,197,064 B1 | 3/2001 | Haines |
| 6,203,576 B1 | 3/2001 | Afriat |
| 6,206,926 B1 | 3/2001 | Pappas |
| 6,210,443 B1 | 4/2001 | Marceaux |
| 6,235,060 B1 | 5/2001 | Kubein-Meesenburg |
| 6,236,875 B1 | 5/2001 | Becholz |
| 6,264,697 B1 | 7/2001 | Walker |
| 6,285,902 B1 | 9/2001 | Kienzle |
| 6,306,146 B1 | 10/2001 | Dinkler |
| 6,306,172 B1 | 10/2001 | O'Neil |
| 6,325,828 B1 | 12/2001 | Dennis |
| 6,340,363 B1 | 1/2002 | Bolger |
| 6,342,075 B1 | 1/2002 | MacArthur |
| 6,348,058 B1 | 2/2002 | Melkent |
| 6,361,564 B1 | 3/2002 | Marceaux |
| 6,368,353 B1 | 4/2002 | Arcand |
| 6,375,658 B1 | 4/2002 | Hangody |
| 6,379,388 B1 | 4/2002 | Ensign |
| 6,401,346 B1 | 6/2002 | Roberts |
| 6,406,497 B2 | 6/2002 | Takei |
| 6,413,279 B1 | 7/2002 | Metzger |
| 6,430,434 B1 | 8/2002 | Mittelstadt |
| 6,436,145 B1 | 8/2002 | Miller |
| 6,443,991 B1 | 9/2002 | Running |
| 6,458,128 B1 | 10/2002 | Schulze |
| 6,470,207 B1 | 10/2002 | Simon |
| 6,475,241 B2 | 11/2002 | Pappas |
| 6,477,400 B1 | 11/2002 | Barrick |
| 6,482,409 B1 | 11/2002 | Lobb |
| 6,485,519 B2 | 11/2002 | Meyers |
| 6,491,699 B1 | 12/2002 | Henderson |
| 6,491,726 B2 | 12/2002 | Pappas |
| 6,500,208 B1 | 12/2002 | Metzger |
| 6,506,215 B1 | 1/2003 | Letot |
| 6,520,964 B2 | 2/2003 | Tallarida |
| 6,554,838 B2 | 4/2003 | McGovern |
| 6,575,980 B1 | 6/2003 | Robie |
| 6,579,290 B1 | 6/2003 | Hardcastle |
| 6,595,997 B2 | 7/2003 | Axelson |
| 6,620,198 B2 | 9/2003 | Burstein |
| 6,623,526 B1 | 9/2003 | Lloyd |
| 6,645,251 B2 | 11/2003 | Salehi |
| 6,679,917 B2 | 1/2004 | Ek |
| 6,685,711 B2 | 2/2004 | Axelson |
| 6,694,168 B2 | 2/2004 | Traxel |
| 6,694,768 B2 | 2/2004 | Lu |
| 6,695,848 B2 | 2/2004 | Haines |
| 6,697,664 B2 | 2/2004 | Kienzle |
| 6,697,768 B2 | 2/2004 | Yingzhong Lue |
| 6,701,174 B1 | 3/2004 | Krause |
| 6,702,821 B2 | 3/2004 | Bonutti |
| 6,711,432 B1 | 3/2004 | Krause |
| 6,725,080 B2 | 4/2004 | Melkent |
| 6,755,563 B2 | 6/2004 | Wahlig |
| 6,755,864 B1 | 6/2004 | Brack |
| 6,764,516 B2 | 7/2004 | Pappas |
| 6,767,356 B2 | 7/2004 | Kanner |
| 6,770,097 B2 | 8/2004 | Leclercq |
| 6,773,461 B2 | 8/2004 | Meyers |
| 6,783,550 B2 | 8/2004 | MacArthur |
| 6,796,988 B2 | 9/2004 | Melkent |
| 6,827,723 B2 | 12/2004 | Carson |
| 6,858,032 B2 | 2/2005 | Chow |
| 6,866,684 B2 | 3/2005 | Fell |
| 6,875,222 B2 | 4/2005 | Long |
| 6,898,858 B1 | 5/2005 | Spell |
| 6,911,044 B2 | 6/2005 | Fell |
| 6,916,324 B2 | 7/2005 | Sanford |
| 6,916,340 B2 | 7/2005 | Metzger |
| 6,942,627 B2 | 9/2005 | Huitema |
| 6,942,694 B2 | 9/2005 | Liddicoat |
| 7,018,418 B2 | 3/2006 | Amrich |
| 7,029,477 B2 | 4/2006 | Grimm |
| 7,048,741 B2 | 5/2006 | Swanson |
| 7,077,867 B2 | 7/2006 | Pope |
| 7,104,966 B2 | 9/2006 | Shilber |
| 7,104,996 B2 | 9/2006 | Bonutti |
| 7,141,053 B2 | 11/2006 | Rosa |
| 7,172,596 B2 | 2/2007 | Coon |
| 7,175,630 B2 | 2/2007 | Farling |
| 7,241,298 B2 | 7/2007 | Nemec |
| 7,326,252 B2 | 2/2008 | Otto |
| 7,344,541 B2 | 3/2008 | Haines |
| 7,371,240 B2 | 5/2008 | Pinczewski |
| 7,422,605 B2 | 9/2008 | Burstein |
| 7,491,235 B2 | 2/2009 | Fell |
| 2001/0018615 A1 | 8/2001 | Biegun |
| 2001/0044627 A1 | 11/2001 | Justin |
| 2002/0055784 A1 | 5/2002 | Bustein |
| 2002/0103541 A1 | 8/2002 | Meyers |
| 2002/0107576 A1 | 8/2002 | Meyers |
| 2002/0120340 A1 | 8/2002 | Metzger |
| 2002/0161447 A1 | 10/2002 | Salehi |
| 2003/0055501 A1 | 3/2003 | Fell |
| 2003/0055509 A1 | 3/2003 | McQue |
| 2003/0060882 A1 | 3/2003 | Fell |
| 2003/0060883 A1 | 3/2003 | Fell |
| 2003/0060884 A1 | 3/2003 | Fell |
| 2003/0060885 A1 | 3/2003 | Fell |
| 2003/0069585 A1 | 4/2003 | Axelson |
| 2003/0069591 A1 | 4/2003 | Carson |
| 2003/0093156 A1 | 5/2003 | Metzger |
| 2003/0181986 A1 | 9/2003 | Buchholz |
| 2003/0212413 A1 | 11/2003 | Wilk |
| 2004/0039396 A1 | 2/2004 | Couture |
| 2004/0044414 A1 | 3/2004 | Nowakowski |

| | | | |
|---|---|---|---|
| 2004/0122305 A1 | 6/2004 | Grimm | |
| 2004/0152970 A1 | 8/2004 | Hunter | |
| 2004/0153066 A1 | 8/2004 | Coon | |
| 2004/0199249 A1 | 10/2004 | Fell | |
| 2004/0243244 A1* | 12/2004 | Otto et al. | 623/20.27 |
| 2004/0249467 A1 | 12/2004 | Meyers | |
| 2004/0249471 A1 | 12/2004 | Bindseil | |
| 2004/0267363 A1 | 12/2004 | Fell | |
| 2005/0033424 A1 | 2/2005 | Fell | |
| 2005/0149038 A1 | 7/2005 | Haines | |
| 2005/0149039 A1 | 7/2005 | Haines | |
| 2005/0149040 A1 | 7/2005 | Haines | |
| 2005/0171604 A1 | 8/2005 | Michalow | |
| 2006/0015109 A1 | 1/2006 | Haines | |
| 2006/0015115 A1 | 1/2006 | Haines | |
| 2006/0015116 A1 | 1/2006 | Haines | |
| 2006/0015117 A1 | 1/2006 | Haines | |
| 2006/0030853 A1 | 2/2006 | Haines | |
| 2006/0030854 A1 | 2/2006 | Haines | |
| 2006/0030855 A1 | 2/2006 | Haines | |
| 2006/0030944 A1 | 2/2006 | Haines | |
| 2006/0052875 A1 | 3/2006 | Bernero | |
| 2006/0058882 A1 | 3/2006 | Haines | |
| 2007/0078517 A1 | 4/2007 | Engh | |
| 2007/0179607 A1 | 8/2007 | Hodorek | |
| 2009/0076514 A1 | 3/2009 | Haines | |
| 2009/0082773 A1 | 3/2009 | Haines | |
| 2009/0138018 A1 | 5/2009 | Haines | |

FOREIGN PATENT DOCUMENTS

| | | |
|---|---|---|
| EP | 0121142 | 10/1984 |
| EP | 0189253 | 7/1986 |
| EP | 0243109 B1 | 10/1987 |
| EP | 0327249 A2 | 8/1989 |
| EP | 0337901 | 10/1989 |
| EP | 0380451 A2 | 1/1990 |
| EP | 0941719 | 9/1990 |
| EP | 0415837 A2 | 3/1991 |
| EP | 0466659 A2 | 1/1992 |
| EP | 0466659 A3 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0682916 A3 | 11/1995 |
| EP | 0761242 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |
| FR | 2710258 | 3/1995 |
| FR | 2760352 | 9/1998 |
| GB | 1409150 | 10/1975 |
| GB | 2007980 | 7/1982 |
| GB | 2296443 | 7/1996 |
| GB | 2324249 | 10/1998 |
| GB | 2335145 | 9/1999 |
| JP | 02-501806 A | 1/1983 |
| JP | 58-209343 | 12/1983 |
| JP | 61-170453 | 8/1986 |
| JP | 62-133948 | 6/1987 |
| JP | 62-254750 | 6/1987 |
| JP | 01-119244 | 5/1989 |
| JP | 01-126957 | 5/1989 |
| JP | 01-209055 | 8/1989 |
| JP | 02-057247 | 2/1990 |
| JP | 02-234756 | 9/1990 |
| JP | 02-234757 | 9/1990 |
| JP | 02-239861 | 9/1990 |
| JP | 02-243143 | 9/1990 |
| JP | 02-246971 | 10/1990 |
| JP | 2002/274214 | 11/1990 |
| JP | 03-032663 | 2/1991 |
| JP | 04-297254 | 10/1992 |
| JP | 04-361746 | 12/1992 |
| JP | 05-03880 | 1/1993 |
| JP | 05-502814 | 5/1993 |
| JP | 5-41510 | 6/1993 |
| JP | 05-269140 | 10/1993 |
| JP | 05-277130 | 10/1993 |
| JP | 06-08033 | 1/1994 |
| JP | 06-38971 | 2/1994 |
| JP | 6-217984 | 8/1994 |
| JP | 06-233775 | 8/1994 |
| JP | 06-237941 | 8/1994 |
| JP | 7-501966 | 3/1995 |
| JP | 7-116185 | 5/1995 |
| JP | 7-136200 | 5/1995 |
| RU | 2121319 C1 * | 11/1998 |
| SE | 382155 | 1/1976 |
| SU | 577020 T | 10/1977 |
| WO | WO 81/03122 | 11/1981 |
| WO | WO 91/00061 | 1/1991 |
| WO | WO 91/10408 | 7/1991 |
| WO | WO 93/22990 | 11/1993 |
| WO | WO 93/25157 | 12/1993 |
| WO | WO 94/05212 | 3/1994 |
| WO | WO 94/08528 | 4/1994 |
| WO | WO 94/09730 | 5/1994 |
| WO | WO 94/14366 | 7/1994 |
| WO | WO 94/22397 | 10/1994 |
| WO | WO96/01588 | 1/1996 |
| WO | WO96/07361 A1 | 3/1996 |
| WO | WO 96/24295 | 8/1996 |
| WO | WO 97/05827 | 2/1997 |
| WO | WO97/29703 A1 | 8/1997 |
| WO | WO97/29704 A1 | 8/1997 |
| WO | WO 9820817 A1 * | 5/1998 |
| WO | WO 99/27872 | 6/1999 |
| WO | WO 99/30649 | 6/1999 |
| WO | WO 01/13825 | 3/2001 |
| WO | WO 02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

*Hudson Surgical Design v. Zimmer Holdings, Inc., et al.*, Revised Final Claim Construction Chart, dated Mar. 11, 2009.

T.D.V. Cooke et al., *Universal Bone Cutting Device for Precision Knee Replacement Arthroplasty and Osteotomy*, 7 J. Biomed. Eng'g 45, 47, col. 2,11. 52-57 (1985).

E. Marlowe Goble and Daniel F. Justin, *Minimally invasive total knee replacement: principles and technique*, Orthop. Clin. N. Am. 35 (2004) 235-245.

Whiteside Ortholoc Total Knee System: Surgical Procedure, Dow Corning Wright, pp. WMT000001-WMT000040, Jun. 1985.

Zimmer, Insall/Burstein II *Constrained Condylar: Modular Knee System*, Surgical Technique, copyright 1989.

Zimmer, The Miller/Galante Advantage: Total Knee System, pp. ZH000159653-ZH000159668.

Whiteside Ortholoc Total Knee System, Dow Corning Wright, pp. ZH000109679-ZH000109690.

Zimmer, Insall/Burnstein II, *Modular Knee System*, Surgical Technique, pp. ZH000109691-ZH000109710.

*Hudson Surgical Design, Inc. v. Zimmer Holdings, Inc., Zimmer Inc., Rush System for Health and Rush University Medical Center, Hudson Surgical Design, Inc.'s Opening Brief on Claim Construction*, Civil Action No. 08C1566, Document No. 83, Filed Nov. 17, 2008, pp. 1-40 (also includes Exhibits 1-40).

*Hudson Surgical Design, Inc. v. Zimmer Holdings, Inc., Zimmer, Inc. Rush System for Health and Rush University Medical Center*, Civil Action No. 08C1566, *Statement of Thomas D. Petersen, M.D.* (including Exhibit A-G), Dated Sep. 2, 2009.

*Hudson Surgical Design, Inc. v. Zimmer Holdings, Inc. et al.*, *Notification of Docket Entry*, Filed Sep. 21, 2009, Document 138, Case No. 1:08-cv-01566, 1 page.

*Hudson Surgical Design, Inc. v Zimmer Holdings, Inc., et. al*, Case No. 1:08-cv-01566, Jan. 27, 2009, vol. 1-A, Transcript of Markman Hearing Before the Honorable Virginia M. Kendal United States District Judge, pp. 1-66 & index pp. 1-12.
*Hudson Surgical Design, Inc.* v. *Zimmer Holdings, Inc., Rush System for Health and Rush University Medical Center*. Civil Action No. 08C1566, vol. 1-2, (including Non-confidential Exhibits).
*Hudson Surgical Design, Inc.* v *Zimmer Holdings, Inc., et. al*, Case No. 1:08-cv-01566, Jan. 27, 2009, vol. 1-B, Transcript of Markman Hearing Before the Honorable Virginia M. Kendal United States District Judge, pp. 67-133, & index pp. 1-13.
*Hudson Surgical Design, Inc.* v. *Zimmer Holdings, Inc., Zimmer, Inc., Rush System for Health and Rush University Medical Center, Hudson Surgical Design, Inc. 's Reply Brief on Claim Construction*, Civil Action No. 08C1566, Document No. 97, Filed Dec. 19, 2008, pp. 1-28.
*Hudson Surgical Design, Inc.* v. *Zimmer Holdings, Inc., Zimmer Inc. Rush System for Health and Rush University Medical Center*, Civil Action No. 08C1566, *Statement of Dr. E Marlowe Goble* (including Non-Confidential Exhibits).
*Hudson Surgical Design, Inc.* v. *Zimmer Holdings, Inc., Zimmer Inc., Rush. System for Health and Rush University Medical Center, Defendant's Responsive Claim Construction Brief*, Case No. 1:08-cv-01566, Document No. 95, Filed Dec. 8, 2008, pp. 1-40 (also included is Exhibit 1-8).
Documents labeled ZHG000157188-ZHG000157198 disclosed in *HSO, Inc.* v. *Zimmer et al.*, 11 pages.
Documents labeled ZHG000157226- ZHG000157253 disclosed in *HSO, Inc.* v. *Zimmer et al.*, 28 pages.
Documents labeled ZHG000157254- ZHG000157270 disclosed in *HSO, Inc.* v. *Zimmer et al.*, 17 pages.
*Hudson Surgical Design, Inc.* v. *Zimmer Holdings, Inc., Zimmer, Inc., Rush System for Health and Rush University Medical Center*. First Amended Complaint, Filed Apr. 11, 2008, Case No. 1:08-cv-01566, pp. 1-8.
*Hudson Surgical Design, Inc.* v. *Zimmer Holdings, Inc., Zimmer, Inc., Rush System for Health and Rush University Medical Center*. Answer, Affirmative Defenses and Counterclaims of Zimmer Holdings, Inc. and Zimmer, Inc. Filed May 9, 2008, Case No. 1:08-cv-01566, pp. 1-10.
*Hudson Surgical Design, Inc.* v. *Zimmer Holdings, Inc., Zimmer, Inc., Rush System for Health and Rush University Medical Center*. Rush System for Health's and Rush University Medical Center' Answer to First Amended Complaint, Filed May 9, 2008, Case No. 1:08-cv-01566, pp. 1-7.
*Hudson Surgical Design, Inc.* v. *Zimmer Holdings, Inc., Zimmer, Inc., Rush System for Health and Rush University Medical Center*. Plaintiff's Reply to Counterclaims of Defendants Zimmer Holdings, Inc. and Zimmer, Inc., Case: 1:08-cv-01566, Filed May 19, 2008, pp. 1-5.
U.S. Appl. No. 12/187,210, filed Aug. 6, 2008.
File History for U.S. Appl. No. 11/075,842, filed Mar. 8, 2005.
U.S. Appl. No. 11/075,828, filed Mar. 8, 2005.
File History for U.S. Appl. No. 11/075,836, filed Mar. 8, 2005.
U.S. Appl. No. 12/171,843, Inventor: Haines, filed Jul. 11, 2008.
U.S. Appl. No. 11/825,857, Inventor: Haines, filed Jul. 9, 2007.
U.S. Appl. No. 11/036,584, Inventor: Haines, filed Jan. 14, 2005.
File History for U.S. Appl. No. 11/075,840, filed Mar. 8, 2005.
U.S. Appl. No. 11/075,552, Inventor: Haines, filed Mar. 8, 2005.
File History for U.S. Appl. No. 08/300,379, filed Sep. 2, 1994.
File History for U.S. Appl. No. 08/342,143, filed Nov. 18, 1994.
File History for U.S. Appl. No. 08/479,363, filed Jun. 7, 1995.
File History for U.S. Appl. No. 08/603,582, filed Feb. 20, 1996.
File History for U.S. Appl. No. 08/649,465, filed May 17, 1996.
File History for U.S. Appl. No. 08/892,286, filed Jul. 14, 1997.
File History for U.S. Appl. No. 09/156,161, filed Sep. 17, 1997.
File History for U.S. Appl. No. 09/261,528, filed Mar. 3, 1999.
File History for U.S. Appl. No. 09/799,325, filed Mar. 5, 2001.
File History for U.S. Appl. No. 10/756,817, filed Jan. 13, 2004.
File History for U.S. Appl. No. 10/967,673, filed Oct. 22, 2004.
File History for U.S. Appl. No. 10/958,203, filed Oct. 4, 2004.
File History for U.S. Appl. No. 10/977,365, filed Oct. 29, 2004.
File History for U.S. Appl. No. 11/049,634, filed Feb. 5, 2005.
File History for U.S. Appl. No. 11/074,599, filed Mar. 8, 2005.
File History for U.S. Appl. No. 11/075,553, filed Mar. 8, 2005.
File History for U.S. Appl. No. 11/933,298, filed Oct. 31, 2007.

Freeman Samuelson, *Total Knee System*, published by Biomet, Inc., 1994 ("Biomet Brochure") (Attached as Exhibit F).
Freeman, Mark II *Total Knee Replacement System*, published 1985 (Attached as Exhibit G).
Protek F/S Modular Total Knee Replacement System, pp. 1-57, published by Protek in Jan. 1991 (Attached as Exhibit H).
Image File Wrapper for U.S. Patent No. 5,611,802, Inventor: Samuelson et al., Issued Mar. 18, 1997 (Attached as Exhibit L).
Image File Wrapper for U.S. Patent No. 5,630,820, Inventor: Todd, Issued May 20, 1997 (Attached as Exhibit M).
*Low Contact Stress Meniscal Bearing Unicompartmental Knee Replacement: Long-Term Evaluation of Cemented and Cementless Results*, Journal of Orthopaedic Rheumatology (presented at the 57th Annual American Academy of Orthopaedic Surgeons Meetings, New Orleans, LA, Feb. 11, 1990), Bates No. DEP00004096-DEP00004107.
N.J. Unicompartmental Knee, Dated Sep. 15, 1989, Bates No. DEP00004108-DEP00004116.
Buechel, Frederick F., *NJ LCS Unicompartmental Knee System with Porocoat*, dated Oct. 24, 1994, Bates No. DEP000004117-DEP00004130.
Buechel, Frederick F. *NJ LCS Unicompartmental Knee System with Porocoat*, 1994, Bates No. DEP00004131-DEP00004141.
Buechel, Frederick F. *NJ LCS Unicompartmental Knee System with Porocoat*, 1994, Bates No. DEP00004142-DEP00004152.
Engh, et al., *The AMK Total Knee System, Design Rationale and Surgical Procedure*, dated 1989, Bates No. DEP00004153-DEP00004201.
*Advertising Proteck Mark II PCR Total Knee Replacement System*, Journal of Bone and Joint Surgery, 1987, Bates No. DEP00004202-DEP00004230.
Protek, *Parts Brochure for Mark II Protek*, 1987, Bates No. DEP00004231-DEP00004235.
Chapman, Michael W., *Operative Orthopaedics*, vol. 1, Published by J.B. Lipponcott Co., Philadelphia, dated 1988, Bates No. DEP00004236-DEP00004247.
American Academy of Orthopaedic Surgeons, *Flyer from 57th Annual American Academy of Orthopaedic Surgeons Meeting*, Feb. 13, 1990, Bates No. DEP00004248-DEP00004251.
Crossett et al., *AMK Congruency Instrument System, Surgical Technique*, dated 1997, Bates No. DEP00004252-DEP00004267.
Engh et al., *AMK Surgical Technique*, Bates No. DEP00004268-DEP00004298, dated 1989.
Engh et al., *AMK Surgical Technique*, Bates No. DEP00004299-DEP0004329, dated 1989.
Crenshaw, A.H., *Campbell's Operative Orthopaedics*, 4th Edition, vol. 1, Bates No. DEP00004330-DEP00004333, dated 1963.
Biomet, *Oxford Brochure: Consistent Instrumentation*, Bates No. DEP00004334-DEP00004336, undated, Aug. 2, 2002.
Howmedica, *Duraconcept, Design Concepts of the Duracon Total Knee System*, Bates No. DEP00004337-DEP00004337, dated 1993.
Freeman et al., *Total Knee System*, Bates No. DEP00004350-DEP00004361, Published prior to Jun. 7, 1994.
Freeman et al., *F/S Modular Total Knee Replacement System-SICOT*, 90 Edition, Bates No. DEP00004362-DEP00004373, dated 1990.
Buechel, Frederick F., *Howmedica Product Catalog*, Bates No. DEP00004374-DEP00004375, dated 1994.
Massarella, Antony, *Interax Bulletin*, No. 6, *Tibial Intramedullary Alignment Surgical Technique*, Bates No. DEP00004387-DEP00004390, dated Feb. 23, 1994.
Desjardins et al., *Interax Operative Technique*, Bates No. DEP00004391-DEP00004411, dated 1994.
Desjardins et al., *Interax Total Knee Operative Technique: Monogram Total Knee Instruments*, Bates No. DEP00004412-DEP00004432, dated 1993.
Howmedica, *Interax Tibial IM*, Bates No. DEP00004433-DEP00004433, dated 1994.
Depuy, *LCS Uni PMA Data from FDA Website*, Bates No. DEP00004434- DEP00004434, dated 1991.
Briard et al., *LCS Uni Unicompartmental Knee System with Porocoat*, Bates No. DEP00004452-DEP00004462, dated 1991.
Freeman et al., *Mark II Total Knee Replacement System*, Bates No. DEP00004463-DEP00004492, dated 1985.

Buechel, Frederick F., *NJ LCS Unicompartmental Knee System with Porocoat*, Bates No. DEP00004493-DEP00004503, dated 1994.

Chapman, Michael W. *Operative Orthopaedics*, vol. 3, 2$^{nd}$ Edition, Published by J.B. Lipponcott Co., Bates No. DEP00004504-DEP00004508, dated 1993.

Biomet, *Oxford Meniscal Knee Phase II Unicompartmental Replacement*, Bates No. DEP00004509-DEP00004515, Published prior to Jun. 7, 1994.

Scott et al., *P.F.C. Sigma Unicompartmental Knee System*, Bates No. DEP00004531-DEP00004539, dated 1998.

Freeman et al., *F/S Modular Total Knee Replacement System*, Bates No. DEP00004540-DEP00004596, dated 1990.

Photos of Miller-Galante Zimmer Instruments, Bates No. DEP00004597- DEP00004598, undated, Jun. 3, 1997.

Photos of Interax Knee Instruments, Bates No. DEP00004666-DEP00004671, undated, Apr. 4, 2001.

Broughton et al., *Unicompartmental Replacement and High Tibial Osteotomy for Osteoarthritis of the Knee*, Journal of Bone and Joint Surgery, vol. 68-B, No. 3, May 1, 1986, pp. 447-452, Bates No. DEP00004752-DEP00004763.

Scott et al., *Uncondylar Unicompartmental Replacement for Osteoarthrisit of the Knee*, Journal of Bone and Joint Surgery, vol. 63-A, No. 4, Apr. 1, 1981, Bates No. DEP00004764-DEP00004775.

Thornhill, Thomas S., *Unicompartmental Knee Arthroplasty Clinical Orthopaedics and Related Research*, No. 205, Apr. 1, 1986, pp. 121-131, Bates No. DEP00004776-DEP00004791.

Forst et al., *A Special jg for Tibial Resection for the Implantation of GSB-Knee-Prostheses in Problematic cases*, pp. 162-166, dated Jun. 1, 1984, Bates No. DEP00004838-DEP00004842.

Ingillis et al., *Revision Total Knee Replacement Techniques in Orthopedics*, dated Apr. 1, 1990, Bates No. DEP00005583-DEP00005592.

Appendix A, 31 pages, Chart regarding Patent No. 7,344,541, undated, Oct. 15, 2010.

Appendix B, 66 pages, undated, Oct. 15, 2010.

Appendix C, 799 pages, undated, Oct. 15, 2010.

Request for Inter Partes Reexamination of U.S. Patent No. 7,344,541, Issued Mar. 18, 2008, 889 pages.

*Hudson Surgical Design*, Inc. vs. *Depuy Orthopaedics, Inc.*, Defendant Depuy Orthopaedics, Inc.'s Local Patent Rule 2.3 Initial Non-Infringement, Invalidity, and Unenforceability Contentions, Civil Action No. 1.-CV-02103, Dated Sep. 27, 2010, 13 pages.

U.S. Appl. No. 12/757,778, filed Apr. 9, 2010, Inventor: Haines.

U.S. Appl. No. 12/023,112, filed Jan. 31, 2008, Inventor: Jason Otto.

USPTO Correspondence entitled Order Granting/Denying Request for Inter Partes Reexamination, U.S. Appl. No. 95/001,469, Patent Number Under Reexamination: 7,344,541, dated Nov. 10, 2010, 15 pages.

U.S. Appl. No. 95/001,469, Patent Under Reexamination: 7,344,541, filed Oct. 15, 2010.

Demand for Arbitration, *Smith & Nephew, Inc.* vs. *Hudson Surgical Design, Inc.*, 21 pages, dated Aug. 16, 2011.

\* cited by examiner

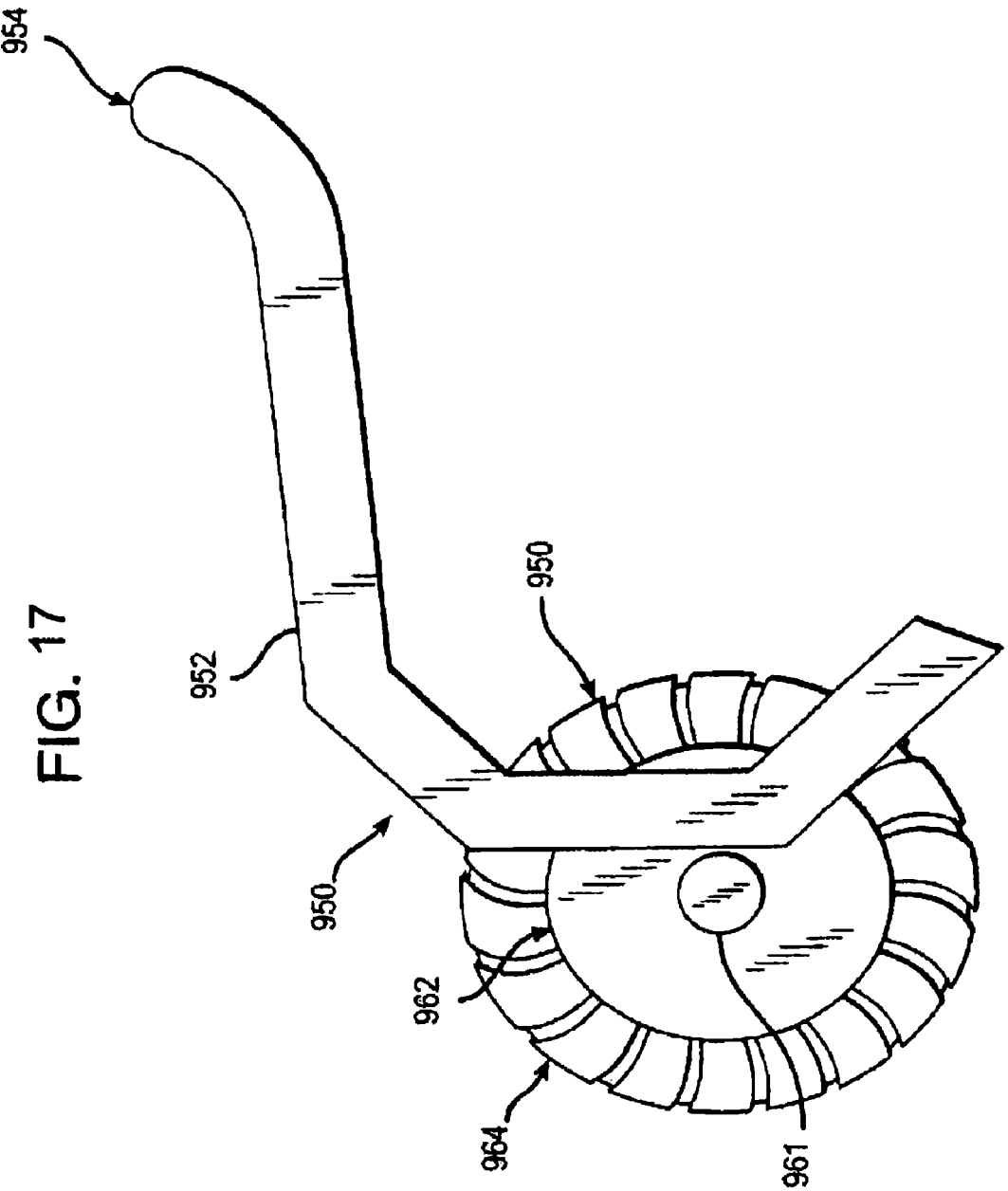

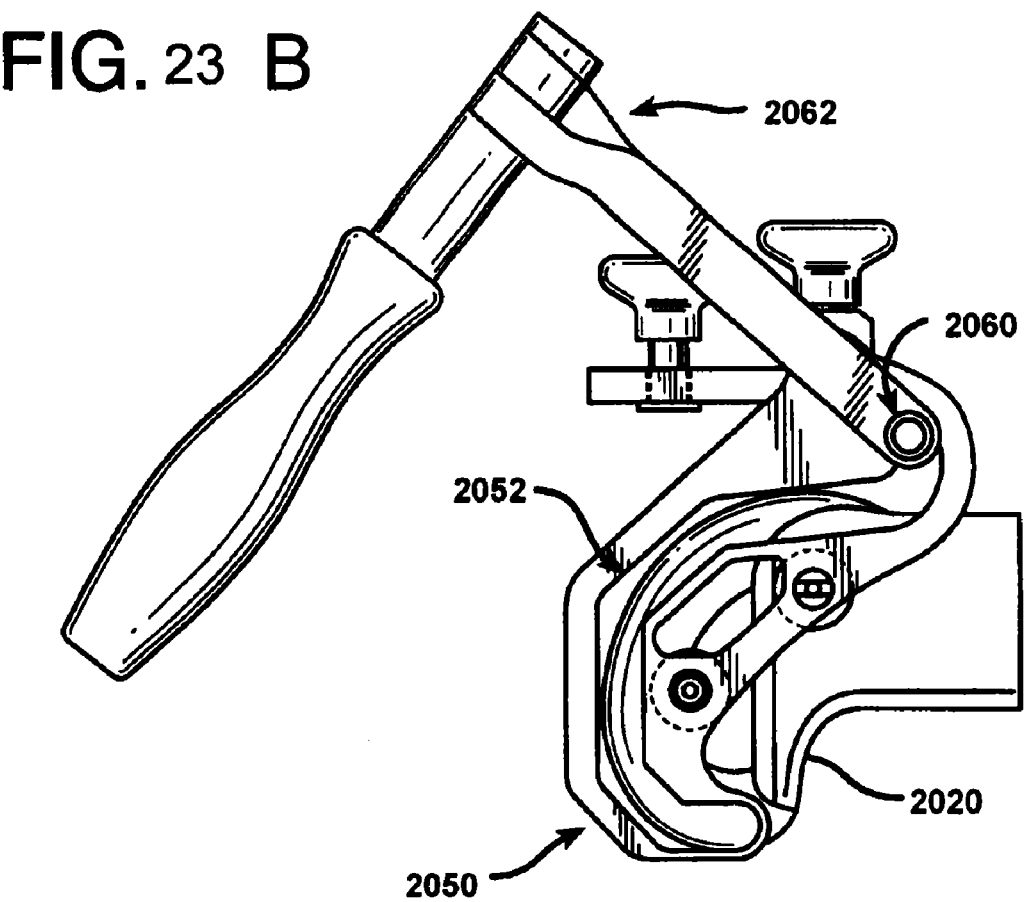

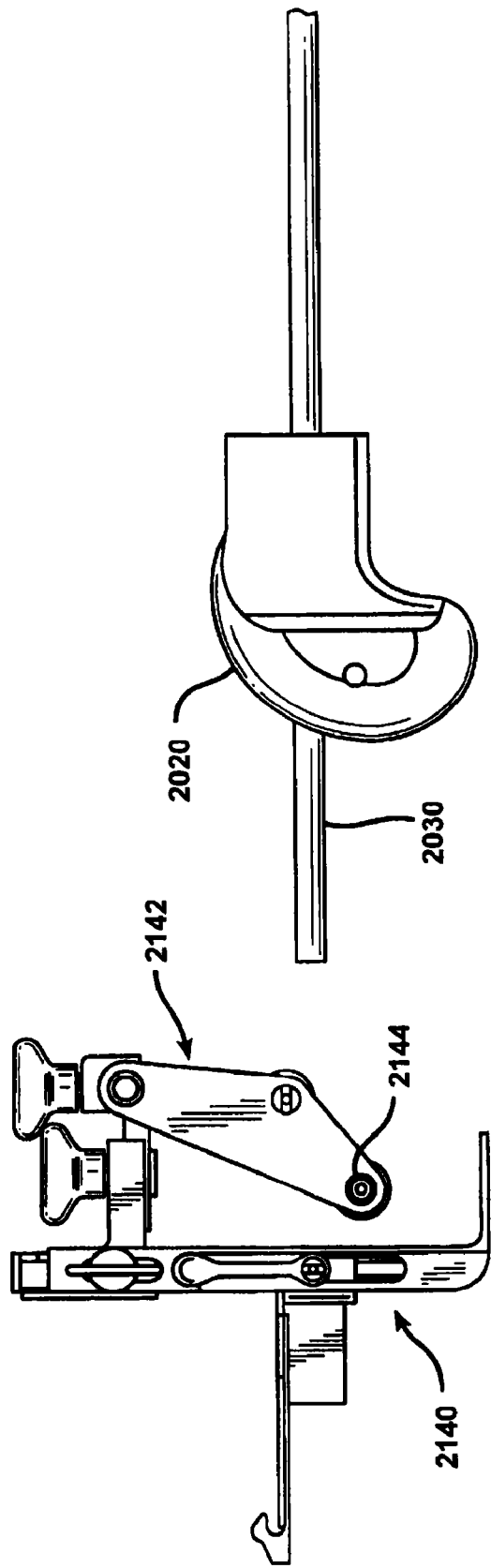

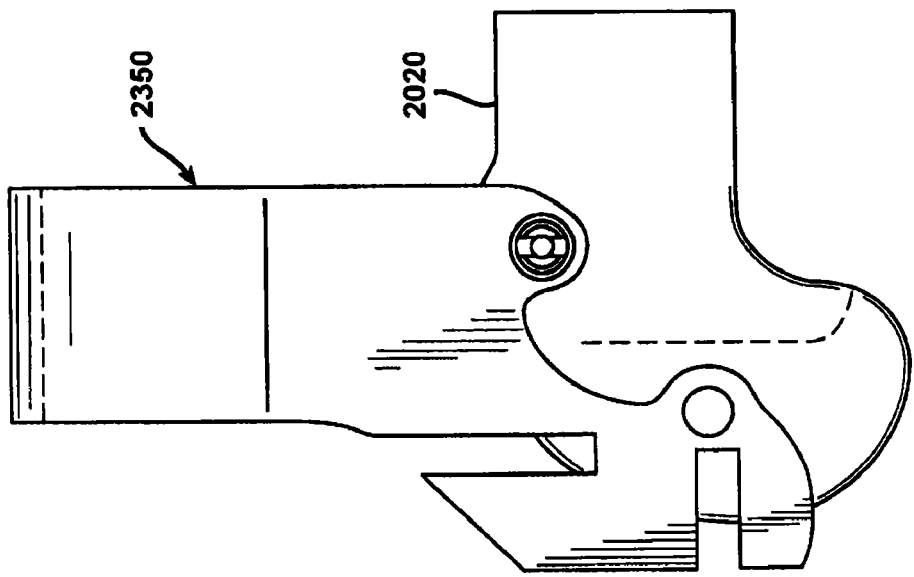
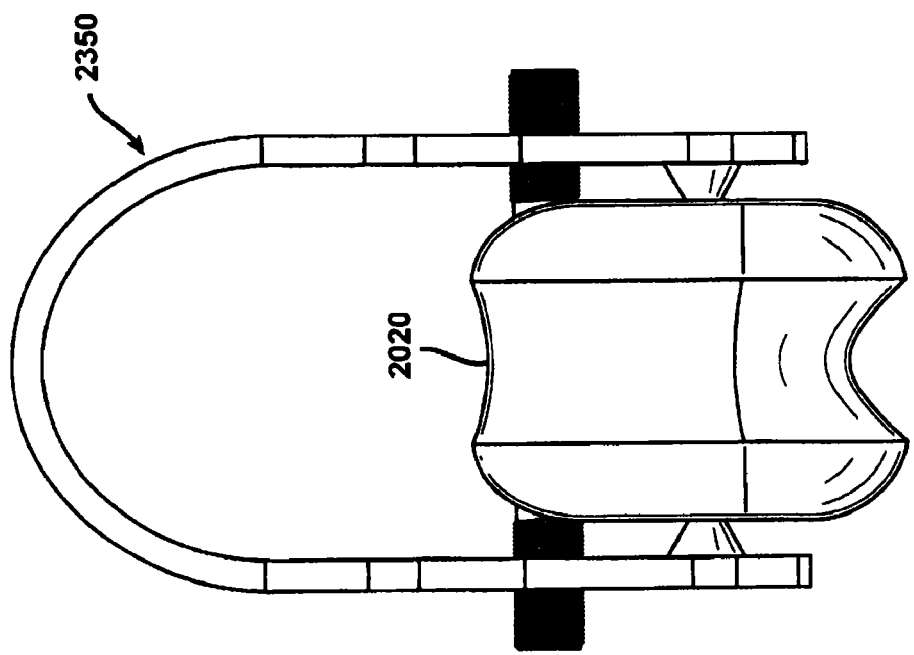

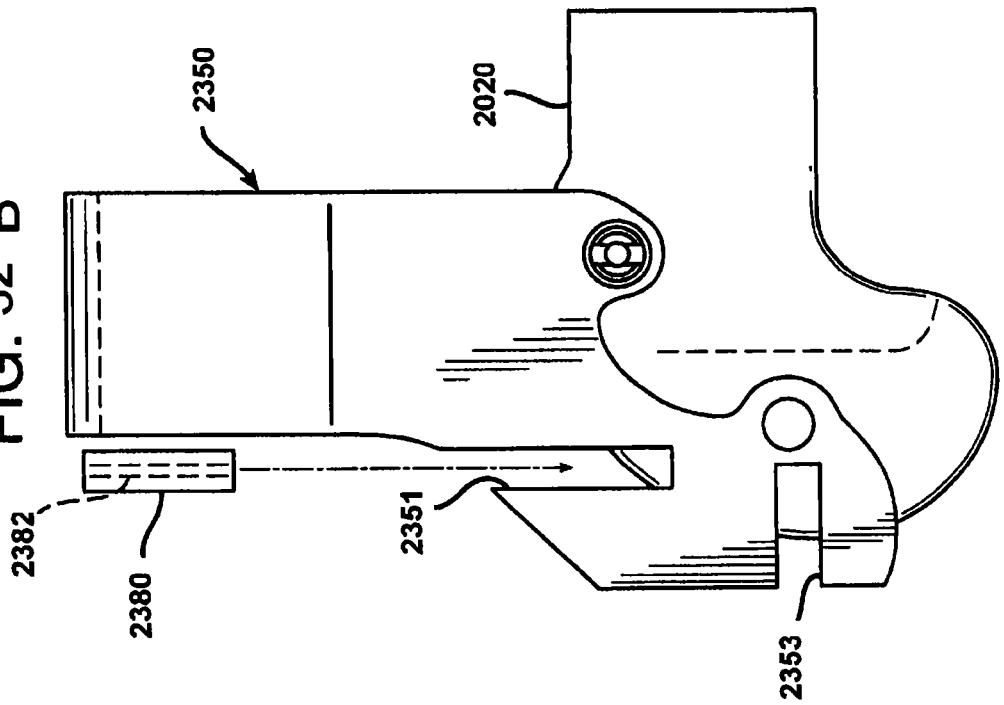
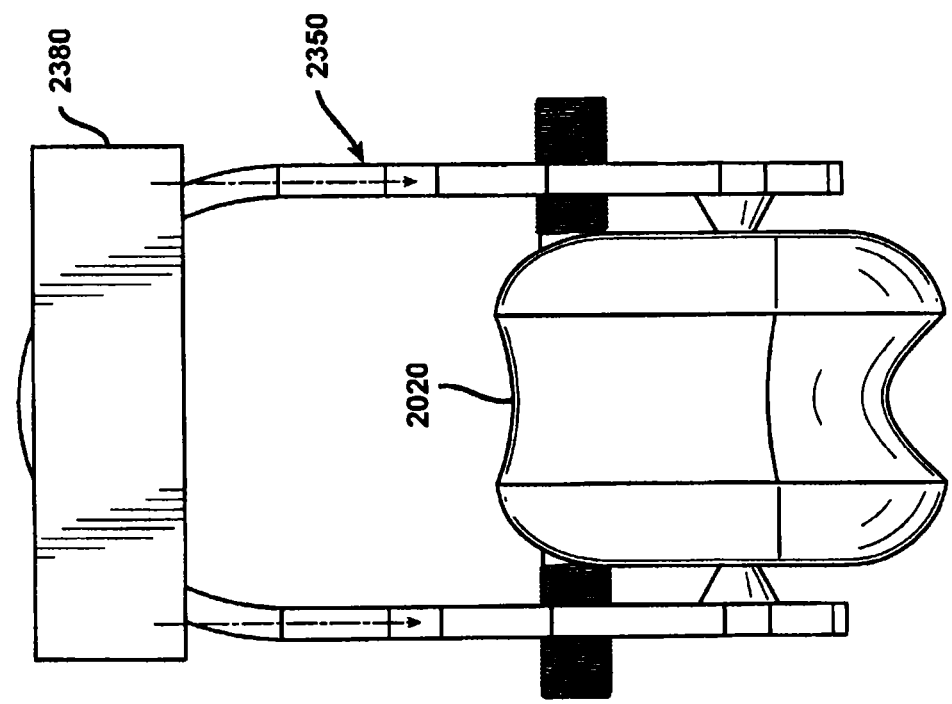

FEMORAL PROSTHETIC IMPLANT

PRIORITY APPLICATIONS

This application is a continuation U.S. application Ser. No. 11/933,298, filed Oct. 31, 2007, which is a continuation of U.S. application Ser. No. 10/756,817, filed Jan. 13, 2004, now U.S. Pat. No. 7,344,541, which is a continuation of U.S. application Ser. No. 09/799,325 filed Mar. 5, 2001, now U.S. Pat. No. 6,695,848. The entire disclosures of these priority applications are expressly incorporated herein by reference.

RELATED APPLICATIONS AND PATENTS

This application is related to U.S. application Ser. Nos. 10/958,203 and 10/967,673, all of which are assigned to the assignee of the present application and the entire disclosure of each of which is expressly incorporated herein by reference. This application is also related to U.S. Pat. Nos. 6,197,064, 5,879,354, 5,810,827, 5,755,803, 5,643,272, 5,597,379, and 5,514,139, all of which are assigned to the assignee of the present application and the entire disclosures of each of which are expressly incorporated herein by reference.

BACKGROUND OF THE INVENTION

1. Field of the Invention

This invention generally relates to methods and apparatus for knee arthroplasty, including implants, guides, tools and techniques for the femur and/or tibia.

2. Related Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating sawblade based resection systems has been the standard in total knee replacement for over 30 years. Due to their use of this sub-optimal cutting tool, the instrumentation systems all possess certain limitations and liabilities.

Perhaps the most critical factor in the clinical success of TKA is the accuracy of the implant's placement. This can be described by the degrees of freedom associated with each implant; for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of ⅛ or 3/16 inch diameter pin or drill placement in the anterior or distal faces of the femur for placement of cutting guides. In the case of posterior referencing systems, the distal resection cutting guide is positioned by drilling two long drill bits into the anterior cortex. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking," inherent in the use of multiple alignment guides and cutting guides. Another error inherent in these systems further adding to mal-alignment is deflection of the oscillating sawblade during the cutting process. The use of an oscillating sawblade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA for more than 30 years, orthopedic salespeople still report incidences where poor cuts result in significant gaps in the fit between the implant and the bone.

It is an often repeated rule of thumb for orthopedic surgeons that a "Well placed, but poorly designed implant will perform well clinically, while a poorly placed, well designed implant will perform poorly clinically." One of the primary goals of the invention described herein is to eliminate errors of this kind to create more reproducible, consistently excellent clinical results in a manner that requires minimal manual skill on the part of the surgeon.

None of the previous efforts of others disclose all of the benefits and advantages of the present invention, nor do the previous efforts of others teach or suggest all the elements of the present invention.

OBJECTS AND SUMMARY OF THE INVENTION

Many of the specific applications of the method and apparatus of the present invention described herein apply to total knee replacement, a surgical procedure wherein planar surfaces and/or curvilinear surfaces must be created in or on bone to allow for proper attachment or implantation of prosthetic devices. However, it should be noted that it is within the scope of the present invention to apply the methods and apparatus herein described to the removal of any kind of material from bones in any other application where it is necessary, desirable or useful to remove material from bones.

The apparatus of the present invention comprises a number of components including a positioning apparatus, a pattern apparatus and a cutting apparatus.

The pattern apparatus is oriented and located by the use of the positioning apparatus which references the geometry of a bone to be resected and/or other anatomic landmarks. When used to resect a distal femur, the positioning apparatus also references the long axis of the femur. Once the positioning apparatus has been properly located, aligned, and initially fixed in place, the pattern apparatus may be attached thereto, and then adjusted according to the preferences of the surgeon utilizing the apparatus, and then the pattern apparatus can be rigidly fixed to a bone to be resected. This ensures the pattern apparatus is properly located and oriented prior to the use of the cutting apparatus to remove material from the bone.

More specifically, when the method and apparatus of the present invention are used in connection with resecting a distal femur, the positioning apparatus is located and aligned utilizing the intramedullary canal of the femur, (thereby approximating the long axis of the femur), the distal surfaces of the femoral condyles, the anterior surface of the distal femur, and the posterior surfaces of the femoral condyles, which are referenced to indicate the appropriate location and orientation of the pattern apparatus. Fixation means may be used to fix the positioning apparatus, as well as the pattern apparatus to the distal femur. Means may be present in the positioning apparatus and/or pattern device for allowing the following additional adjustments in the location and orientation of the pattern device:
1. internal and external rotational adjustment;
2. varus and valgus angular adjustment;
3. anterior and posterior location adjustments;
4. proximal and distal location adjustment; and
5. flexion and extension angular adjustment.

Cannulated screws, fixation nails or other fixation means may then be used to firmly fix the pattern apparatus to the distal femur. The positioning apparatus may then be disconnected from the pattern apparatus and removed from the distal femur. Thus, the location and orientation of the pattern apparatus is established.

The pattern device possesses slot-like features, or a cutting path, having geometry that matches or relates to the desired geometry of the cut. When used in connection with resecting a knee, the cutting path resembles the interior profile of the distal femoral prosthesis. The cutting path guides the cutting apparatus to precisely and accurately remove material from the distal femur. Thus, the distal femur is thereby properly prepared to accept a properly aligned and located distal prosthesis.

In preparing a patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

The apparatus of the present invention comprises a number of components including an ankle clamp, an alignment rod, a fixation head, cutting guide clamps having an integral attachment mechanism, and a milling bit.

The method of present invention includes the steps of attaching the ankle clamp about the ankle, interconnecting the distal end of the alignment rod with the ankle clamp, interconnecting the fixation head with the proximal end of the alignment rod, partially attaching the fixation head to the proximal tibia, aligning the alignment rod, completely attaching the fixation head to the proximal tibia, interconnecting the cutting guide clamps with the alignment rod, positioning the cutting guide clamps about the proximal tibia, securing the cutting guide clamps to the tibia at a proper location, removing the fixation head, and cutting the proximal tibia with the milling bit.

The implant of the present invention has an outer bearing surface and an inner attachment surface. The outer bearing surface functions as a joint contact surface for the reconstructed bone. The inner attachment surface contacts a bone and is attached thereto. The inner attachment surface of the implant is curvilinear from an anterior to a posterior area of the femur, as is conventionally known, and is also curvilinear from a medial to a lateral area of the femur to approximate the shape of natural femur. The resection of the femur for accommodating the implant can be properly performed by a milling device employing one or more curvilinear milling bits.

There are numerous advantages associated with the curvilinear implant of the present invention. First, it will allow for a very thin implant cross-section and therefore necessitate the removal of the least amount of viable osseous tissue. Accordingly, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs.

This curvilinear implant of the present invention could also result in a less expensive femoral implant because of the reduced amount of material needed for the implant, as well as an improved, more natural, and even stronger knee replacement. The cross-section of the implant could be varied to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces.

The resected surfaces of a femur or other bone to accept the implant of the present invention could be prepared by the apparatus and method for resection shown and described in the prior related applications set forth herein, the entire disclosures of which are expressly incorporated herein by reference.

The apparatus of the present invention comprises a number of components including a positioning and drill guide, a cutting guide and a cutting apparatus. The drill guide is used to create holes in the medial and lateral sides of the femur that correspond to the fixation features of the cutting guide. The cutting guide is oriented and located by inserting fixation nubs connected to the cutting guide into the medial and lateral holes in the femur. The cutting guide can then be further affixed to the femur. The cutting apparatus can then be used with the cutting guide to resect the femur. A conventional cutting block used with a conventional oscillating saw can also be positioned and interconnected with a femur in a similar manner using the drill guide of the present invention to create medial and lateral holes. A cutting guide can then be attached to the holes. A conventional cutting block can be interconnected with the cutting guide for attachment of the block to the femur. This invention can also be used in connection with a cortical milling system, i.e., a cutting system for providing a curvilinear cutting path and curvilinear cutting profile. Likewise, a tibial cutting guide can similarly be positioned on a tibia with a drill guide.

It is a primary object of the present invention to provide an apparatus for properly resecting the distal human femur.

It is also an object of this invention to provide an apparatus for properly orienting a resection of the distal human femur.

It is an additional object of the resection apparatus of the present invention to properly locate the resection apparatus with respect to the distal human femur.

It is even another object of the resection apparatus of the present invention to properly orient the resection apparatus with respect to the distal human femur.

It is another object of the resection apparatus of the present invention to provide a guide device for establishing the location and orientation of the resection apparatus with respect to the distal human femur.

It is still a further object of the resection apparatus of the present invention to lessen the chances of fatty embolisms.

It is even a further object of this invention is to provide a resection apparatus capable of forming some or all of the resected surfaces of the distal human femur.

It is another object of the resection apparatus of the present invention to provide an apparatus which is simple in design and precise and accurate in operation.

It is also an intention of the resection apparatus of the present invention to provide a guide device for determining the location of the long axis of the femur while lessening the chances of fatty embolism.

It is also an object of the resection apparatus of the present invention to provide a device to physically remove material from the distal femur in a pattern dictated by the pattern device.

It is even another object of the resection apparatus of the present invention to provide a circular cutting blade for removing bone from the distal human femur to resection the distal human femur.

It is also an object of the present invention to provide a method for easily and accurately resecting a distal human femur.

These objects and others are met by the resection method and apparatus of the present invention.

It is a primary object of the present invention to provide methods and apparatus for femoral and tibial resection.

It is another object of the present invention to provide a method and apparatus for properly, accurately and quickly resecting a bone.

It is also an object of this invention to provide a method and apparatus for properly orienting and locating a resection of a bone.

It is a further object of the present invention to provide a method and apparatus to properly locate and orient the resection apparatus with respect to a bone.

It is another object of the present invention to provide methods and apparatus for femoral and tibial resection which are simple in design and precise and accurate in operation.

It is an additional object of the present invention to provide a method and apparatus to physically remove material from a bone in a pattern dictated by a pattern device and/or the geometry of a cutting device.

It is a further object of the present invention to provide methods and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is a further object of the present invention to provide methods and apparatus for femoral and tibial resection wherein the apparatus can be located on a bone to be cut in a quick, safe and accurate manner.

It is a primary object of the present invention to provide a method and apparatus for properly resecting the proximal human tibia in connection with knee replacement surgery.

It is also an object of the present invention to provide a method and apparatus for resecting the proximal human tibia which minimizes the skill necessary to complete the procedure.

It is another object of the present invention to provide a method and apparatus for resecting the proximal human tibia which properly orients the resection of the proximal tibia.

It is even another object of the present invention to provide a method and apparatus for resecting the proximal human tibia which is easy to use.

It is yet another object of the present invention to provide a method and apparatus for resecting the proximal human tibia which orients the resection in accordance with what is desired in the art.

It is still yet another object of the present invention to provide a method and apparatus for resecting the proximal human tibia which minimizes the amount of bone cut.

It is a further object of the present invention to provide a method and apparatus for resecting the proximal human tibia which allows one to visually inspect the location of the cut prior to making the cut.

It is even a further object of the present invention to provide a method and apparatus for resecting the proximal human tibia which is simple in design and precise and accurate in operation.

It is yet a further object of the present invention to provide a method and apparatus for resecting the proximal human tibia which physically removes material from the proximal tibia along a surface dictated by a guide device.

It is still a further object of the present invention to provide a method and apparatus for resecting the proximal human tibia which employs a milling bit for removing material from the proximal tibia.

It is also an object of the present invention to provide a method and apparatus for resecting the proximal human tibia which includes a component which is operated, and looks and functions, like pliers or clamps.

It is even another object of the present invention to provide an alternate embodiment of the method and apparatus for resecting the proximal human tibia which includes a component that resembles a U-shaped device for placing about the tibia.

It is even a further object of the present invention to provide an alternate embodiment of the method and apparatus for resecting the proximal human tibia which includes a component that resembles an adjustable, square, U-shaped device for placing about the tibia.

These objects and others are met and accomplished by the method and apparatus of the present invention for resecting the proximal tibia.

It is a primary object of the present invention to provide a method and apparatus for removing material from bones.

It is another object of the present invention to provide a method and apparatus for properly resecting bone.

It is also an object of this invention to provide a method and apparatus for properly orienting a resection of a bone.

It is a further object of the present invention to provide a method and apparatus to properly orient the resection apparatus with respect to a bone.

It is an additional object of the present invention to provide a method and apparatus for properly locating a bone resection.

It is a further object of the present invention to provide a method and apparatus to properly locate the resection apparatus with respect to a bone.

It is even another object of the resection apparatus of the present invention to provide a guide device and method of use thereof for establishing the location and orientation of the resection apparatus with respect to a bone.

It is an additional object of the present invention to provide a method and apparatus for making a curvilinear bone resection.

It is still a further object of the resection apparatus of the present invention to lessen the chances of fatty embolisms.

It is even further object of this invention to provide a method and apparatus capable of forming or re-forming some or all of the surfaces or resected surfaces of a bone.

It is another object of the present invention to provide a method and apparatus which is simple in design and precise and accurate in operation.

It is also an intention of the present invention to provide a method and apparatus for determining the location of the long axis of a bone while lessening the chances of fatty embolisms.

It is also an object of the present invention to provide a method and apparatus to physically remove material from a bone in a pattern.

It is an additional object of the present invention to provide a method and apparatus to physically remove material from a bone in a pattern dictated by a pattern device and/or the geometry of a cutting device.

It is even another object of the resection apparatus of the present invention to provide a cylindrical or semi-cylindrical cutting device and method of use thereof for removing material from a bone.

It is also an object of the present invention to provide a method and apparatus for easily and accurately resecting a bone.

It is also an object of the present invention to provide a method and apparatus for resecting a bone which minimizes the manual skill necessary to complete the procedure.

It is even another object of the present invention to provide a method and apparatus for resecting a bone which is easy to use.

It is still yet another object of the present invention to provide a method and apparatus for resecting a bone which minimizes the amount of bone removed.

It is a further object of the present invention to provide a method and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is even another object of the present invention to provide a method and apparatus for removing material from a bone such that both the cutting path and cutting profile are predominantly curvilinear.

It is a primary object of the present invention to provide an apparatus to properly replace damaged bony tissues.

It is also an object of this invention to provide an apparatus to properly replace damaged bony tissues in joint replacement surgery.

It is also an object of the present invention to provide an implant for the attachment to a distal femur in the context of knee replacement surgery.

It is an additional object of the present invention to provide a method and apparatus for making a curvilinear implant.

It is another object of the present invention to provide an implant having a reduced thickness to reduce the amount of material required to make the implant.

It is even another object of the present invention to provide an implant having curvilinear fixation surfaces for increasing the strength of the implant.

It is another object of the present invention to provide an implant having a fixation surface that is anterior-posterior curvilinear and mediolateral curvilinear.

It is another object of the present invention to provide an implant that has a fixation surface that is shaped to resemble a natural distal femur.

It is also an object of the present invention to provide an implant apparatus for allowing proper patellofemoral articulation.

It is a further object of the present invention to provide for minimal stress shielding of living bone through reduction of flexural rigidity.

It is an additional object of the present invention to provide an implant apparatus having internal fixation surfaces which allow for minimal bony material removal.

It is another object of the present invention to provide an implant apparatus with internal fixation surfaces that minimize stress risers.

It is another object of the present invention to provide an implant apparatus having internal fixation surfaces for precise fixation to curvilinear body resections.

It is another object of the present invention to provide an implant apparatus having internal fixation surfaces for precise apposition to curvilinear body resections.

It is another object of the present invention to provide an implant apparatus having internal fixation surfaces for curvilinear interior fixation geometries closely resembling the geometry of the external or articular geometry of the implant apparatus.

It is also an object of this invention to provide a method and apparatus for properly locating and orienting a prosthetic implant with respect to a bone.

It is another object of the present invention to provide an implant which is simple in design and precise and accurate in operation.

It is also an object of the present invention to provide an implant which minimizes the manual skill necessary to complete the procedure.

It is still yet another object of the present invention to provide an implant which minimizes the amount of bone removed.

It is even another object of the present invention to provide a method and apparatus for removing material from a bone such that both the cutting path and cutting profile are predominantly curvilinear.

It is a primary object of the present invention to provide an apparatus for properly resecting the distal human femur.

It is also an object of this invention to provide an apparatus for properly orienting the resections of the distal human femur.

It is also an object of the present invention to provide an alignment guide apparatus for properly orienting and locating some or all of the distal femoral resections necessary in human total knee arthroplasty.

It is an object of the alignment guide apparatus of the present invention to provide a means for directly or indirectly establishing the proper orientation cutting guide devices for performing distal femoral resections.

It is even an additional objective of the alignment guide apparatus of the present invention to provide a means for directly establishing the proper location of cutting guide devices used to perform distal femoral resections.

It is also an object of the present invention to provide an extension block for determining the gap between a resected proximal tibia and a resected or unresected distal-most surface of the human femur in extension and to allow for appropriate ligament balancing.

It is an additional object of the present invention to provide an extension block for adjusting and balancing the gap between a resected proximal tibia and an unresected or partially resected distal femur.

It is another object of the alignment guide apparatus to provide an alignment device which references the resected surface of the proximal tibia to indicate the proper location and orientation of the device(s) used to guide the cutting devices used to perform the distal femoral resections.

It is another object of this invention to provide an apparatus which is simple in the design and precise and accurate in operation.

These objects and others are met by the femoral resection alignment method and apparatus of the present invention. This apparatus comprises a number of components including a guide body component, an extension block component, a rotating arm component, an extension rod component, and a tibial referencing component. The guide body component contacts the distal-most surface of the femur. Its location is based off of the posterior femoral condyles and the surface of the distal-most femoral resection or the unresected distal-most femoral surface. The rotating arm component is interconnected with the guide body and may rotate with respect thereto, thus allowing for the direct or indirect adjustment of the rotating alignment of cutting guides for resecting the distal femur. In one embodiment, the rotating arm component carries arms with drill screw apertures which direct placement of drill holes in the femur which are used to attach a cutting guide to the femur. In another embodiment the rotating arm component extends above the femur and receives a femoral milling device as shown in U.S. patent application Ser. No. 08/300,379. The rotating arm component is attached to the extension rod component which extends to the tibial referencing component which references the location and orientation of the proximal resected surface of the tibia. Thus the rotating alignment of the distal femoral prosthesis is established with respect to the orientation of the resected proximal tibial surface.

The rotational alignment of the rotating arm component is approximately perpendicular the rotational alignment of the extension rod component in both Anterior/Posterior and Mediolateral planes. The extension rod component contains a means for adjusting the distance between the tibial referencing component and the rotating arm component. The rotating arm component is able to rotate with respect to the guide body which is firmly fixed to the distal femur. The extension rod is firmly fixed in the tibial referencing component which rests on the resected tibial surface. The adjustment of the distance between the tibial referencing component and the rotating arm component distracts the femur from the tibia until distraction is restricted by the collateral ligaments and other soft tissues present in the knee joint. Thus the location and orientation of the distal femoral prosthesis is properly determined with respect to the proximal tibial resection and the soft tissue of the knee joint.

The rotational alignment of the drill holes in the resected distal femur should be parallel to the resected proximal tibia when equal ligament tension is attained through the distraction of the femur from the tibia.

It is a primary object of the present invention to provide methods and apparatus for femoral and tibial resection.

It is another object of the present invention to provide a method and apparatus for properly, accurately and quickly resecting a bone.

It is also an object of this invention to provide a method and apparatus for properly orienting and locating a resection of a bone.

It is a further object of the present invention to provide a method and apparatus to properly locate and orient the resection apparatus with respect to a bone.

It is another object of the present invention to provide methods and apparatus for femoral and tibial resection which are simple in design and precise and accurate in operation.

It is an additional object of the present invention to provide a method and apparatus to physically remove material from a bone in a pattern dictated by a pattern device and/or the geometry of a cutting device.

It is a further object of the present invention to provide methods and apparatus for resecting a bone which allows one to visually inspect the location of the cut or cuts prior to making the cut or cuts.

It is yet a further object of the present invention to provide a method and apparatus for resecting a bone which physically removes material from the bone along a surface dictated by a guide device.

It is still a further object of the present invention to provide a method and apparatus for resecting a bone which employs a milling bit or form cutter for removing material from the bone.

It is a further object of the present invention to provide methods and apparatus for femoral and tibial resection wherein the apparatus can be located on a bone to be cut in a quick, safe and accurate manner.

These objects and others are met by the methods and apparatus for femoral and tibial resection of the present invention. The apparatus of the present invention comprises a number of components including a positioning and drill guide, a cutting guide and a cutting apparatus. The drill guide is used to create holes in the medial and lateral sides of the femur that correspond to the fixation features of the cutting guide. The cutting guide is oriented and located by inserting fixation nubs connected to the cutting guide into the medial and lateral holes in the femur. The cutting guide can then be further affixed to the femur. The cutting apparatus can then be used with the cutting guide to resect the femur. A conventional cutting block used with a conventional oscillating saw can also be positioned and interconnected with a femur in a similar manner using the drill guide of the present invention to create medial and lateral holes. A cutting guide can then be attached to the holes. A conventional cutting block can be interconnected with the cutting guide for attachment of the block to the femur. This invention can also be used in connection with a cortical milling system, i.e. a cutting system for providing a curvilinear cutting path and curvilinear cutting profile. Likewise, a tibial cutting guide can similarly be positioned on a tibia with a drill guide.

BRIEF DESCRIPTION OF THE DRAWINGS

Other important objects and features of the invention will be apparent from the following detailed description of the invention taken in connection with the accompanying drawings in which:

FIG. 17 is a side plan view of the curvilinear milling bit and resection guide shown in FIG. 3.

FIGS. 31A and 31B show front and side views of a cutting guide for positioning a cutting block for use with an oscillating saw for resecting a femur.

FIGS. 32A and 32B show front and side views of a distal cutting guide for use with the cutting guide shown in FIG. 32.

MILLING MEANS

In a preferred embodiment of the invention, a cylindrical milling bit is used for following the cutting path described in the pattern plates for resecting a bone. Importantly, it is within the scope of the present invention to use a flat reciprocating bit, much like a hacksaw, for following the cutting paths described in the pattern plates for resecting a bone.

Further, it may be desirable to make all or some of the cuts using a cylindrical milling bit or a flat reciprocating bit having a smooth center section without cutting means. An advantage of a cutting tool without cutting means along a center portion thereof is the protection of posterior cruciate ligament during resection of the femur. Accordingly, one cutting tool could be used to make the anterior cut, the anterior chamfer, the distal cut and the posterior chamfer, while another cutting tool, with a smooth center portion, could be used to make the posterior cut to avoid any chance of jeopardizing the posterior cruciate ligament.

Additionally, the milling bits herein described can be used with or without a guide handle as will hereinafter be described. Further, it should be pointed out that it is within the scope of the present invention to fabricate the milling bit or other cutting tool from metal as heretofore known, or to alternatively fabricate the milling bit or other cutting tool from a ceramic material. An advantage of a ceramic milling bit or cutting tool is that such resists wear and, accordingly would be a non-disposable component of the present invention which would help to reduce the cost of the system of the present invention.

Three Dimensional Shaping

Figure 1A:
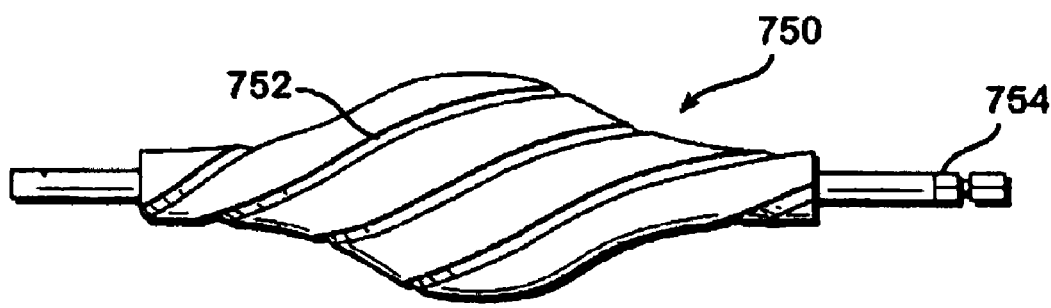
FIGS. 1A and B are front plan views of an embodiment of the cutting apparatus of the present invention for cutting a bone a in curvilinear cross-sectional plane.

Initially, it should be noted that the term cutting profile the profile geometry of a mediolateral section taken normal to the cutting path through the bony surfaces created by cutting the bone. As shown in FIG. 1, in an alternate embodiment of the present invention, a milling apparatus having a three-dimensional profile, or a form cutter, can be used to shape a bone in three-dimensions. The curved profile milling bit 750, like the milling bits used in the previous embodiments of the present invention, includes cutting teeth 752 along the length thereof and spindles 754 at the ends thereof. This milling bit 730 can follow a pattern described by pattern plates and can be guided with a handle as will be hereinafter described.

Figure 3:
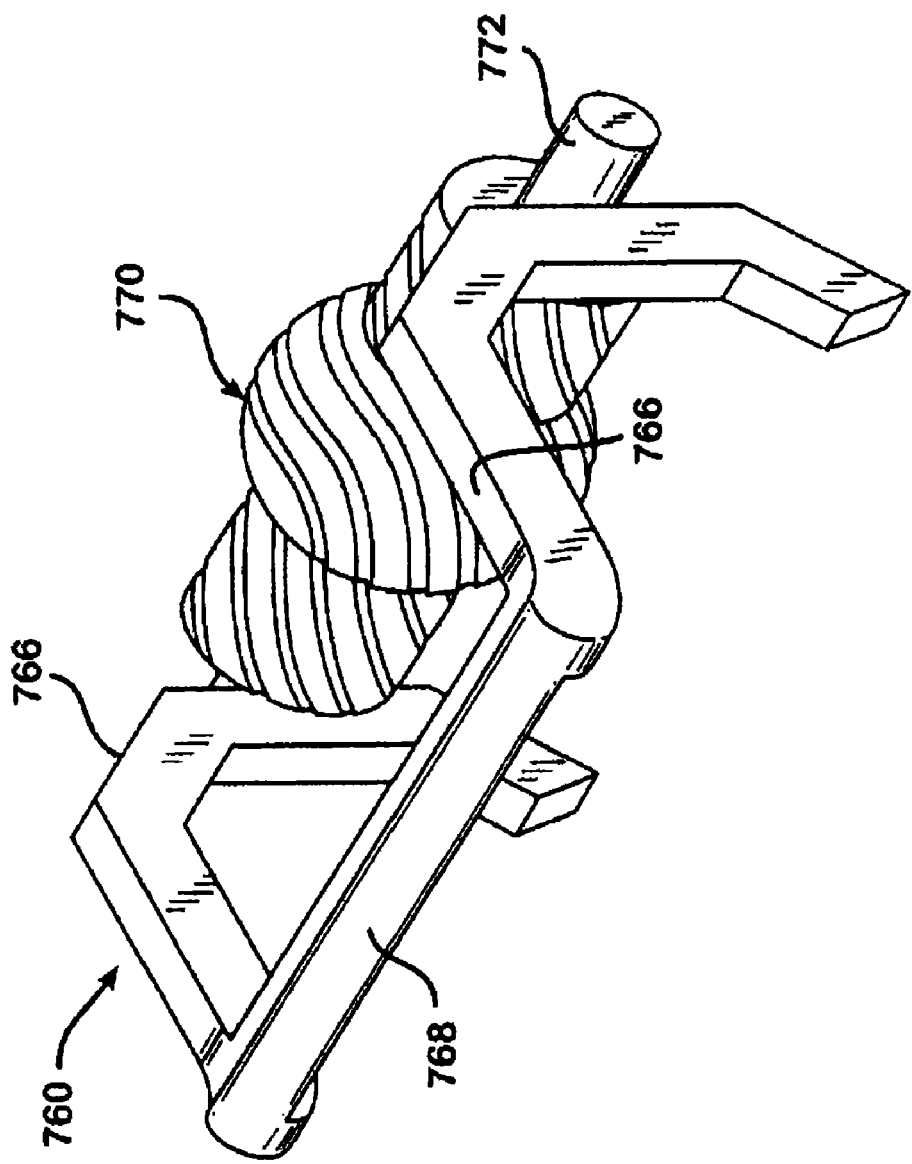
FIG. 3 is a perspective view of an embodiment of a pattern apparatus, having a milling bit engaged therewith.

Importantly, by using a milling bit having a curved profile, one can cut a femur to resemble the natural shape of the femur, i.e., the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof, as shown in FIG. 1, or alternatively, could have one or more bulges discretely formed along the length thereof as shown in FIG. 3.

Guide Handle

Figure 2:
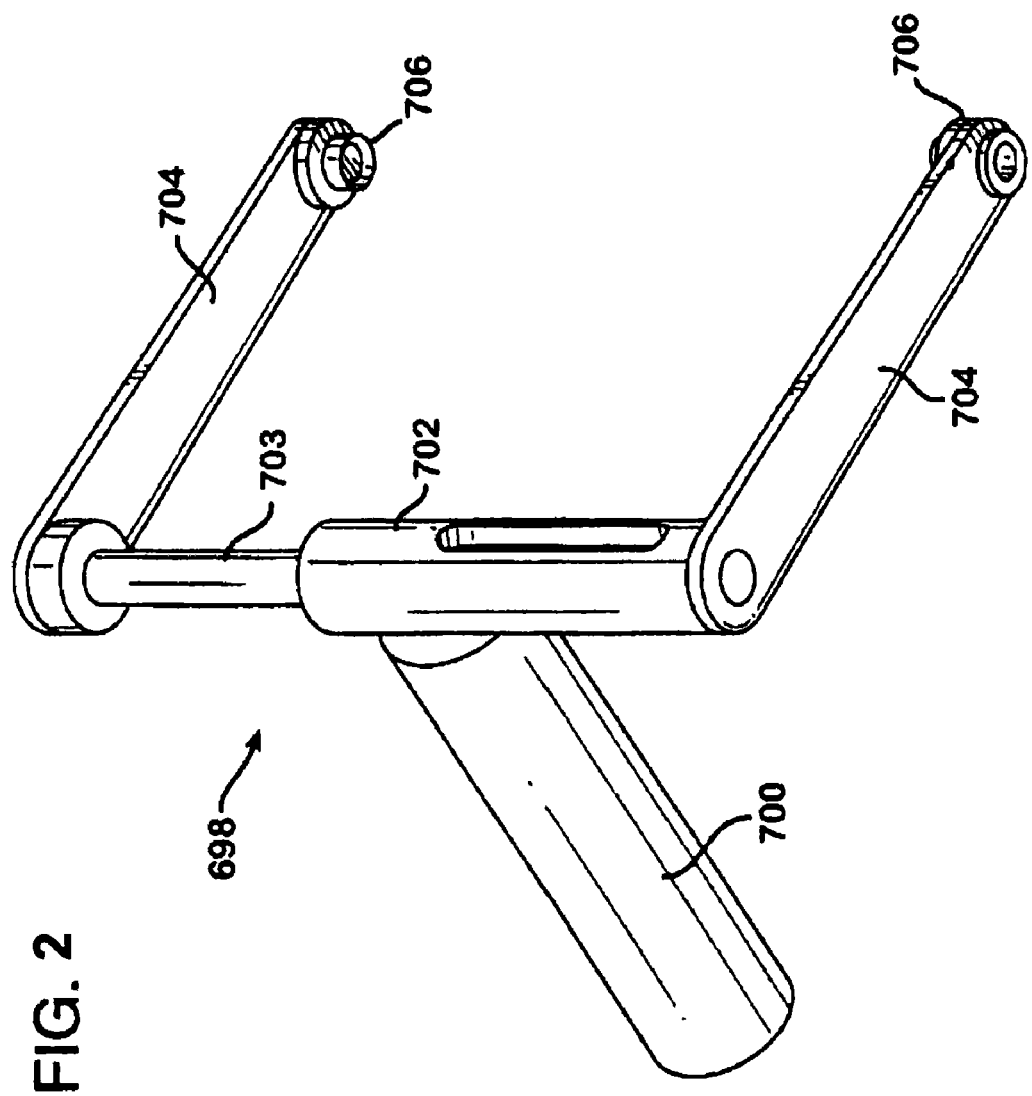
FIG. 2 is a perspective view of a handle for guiding a milling bit along a cutting path.

As shown in FIG. 2, a guide handle, generally indicated at 698 may be used to guide the milling bit along the cutting path of the pattern plate. The guide handle 698 comprises a grip portion 700 which is grasped by the user for manipulating the guide handle 698 and accordingly, the milling bit. The grip portion 700 is interconnected with a crossbar member 702 which includes a extension member 703 telescopically interconnected therewith. The crossbar member 702 and the extension member 703 may be positioned perpendicular with respect to grip portion 700. The extension member 703 is telescopically movable in and out of crossbar member 702. Means may be provided for locking the relative position of the extension with respect to the crossbar. Also, it should be noted that the grip portion may rigidly or pivotally be interconnected with the crossbar as desired.

Extending from outer ends of the crossbar 702 and the extension member 703 are sidebars 704 in facing and parallel relationship. The sidebars 704 have two ends, the first of which are interconnected with the crossbar and the extension member, and the second of which are configured to receive and capture spindles or bushings of a milling bit in spindle bushings 706. The spindle bushings are positioned in a facing relation and could include captured bushings. The captured bushings receive the spindles of a milling bit. The captured bushings are sized to be received by the cutting path in the pattern plates and co-act therewith to guide a milling bit therealong. Accordingly, after the pattern plate or plates are attached to a bone, the milling bit is placed into the cutting path. Next a milling handle 698 is positioned such the spindle bushings are aligned with the spindles of the milling bit. Next, the extension is actuated to retract into the crossbar to move the spindle bushings onto the spindles of the milling bit where they are captured. Next, the spindle bushings are positioned within the cutting path of a pattern plate or plates. If necessary, the extension and crossbar can be locked down to lock the entire apparatus. Next, the milling bit is actuated and the grip portion of the handle is grasped and manipulated to move the milling bit along the cutting path to cut a bone.

Distally Positioned Pattern Plate

Figure 4:
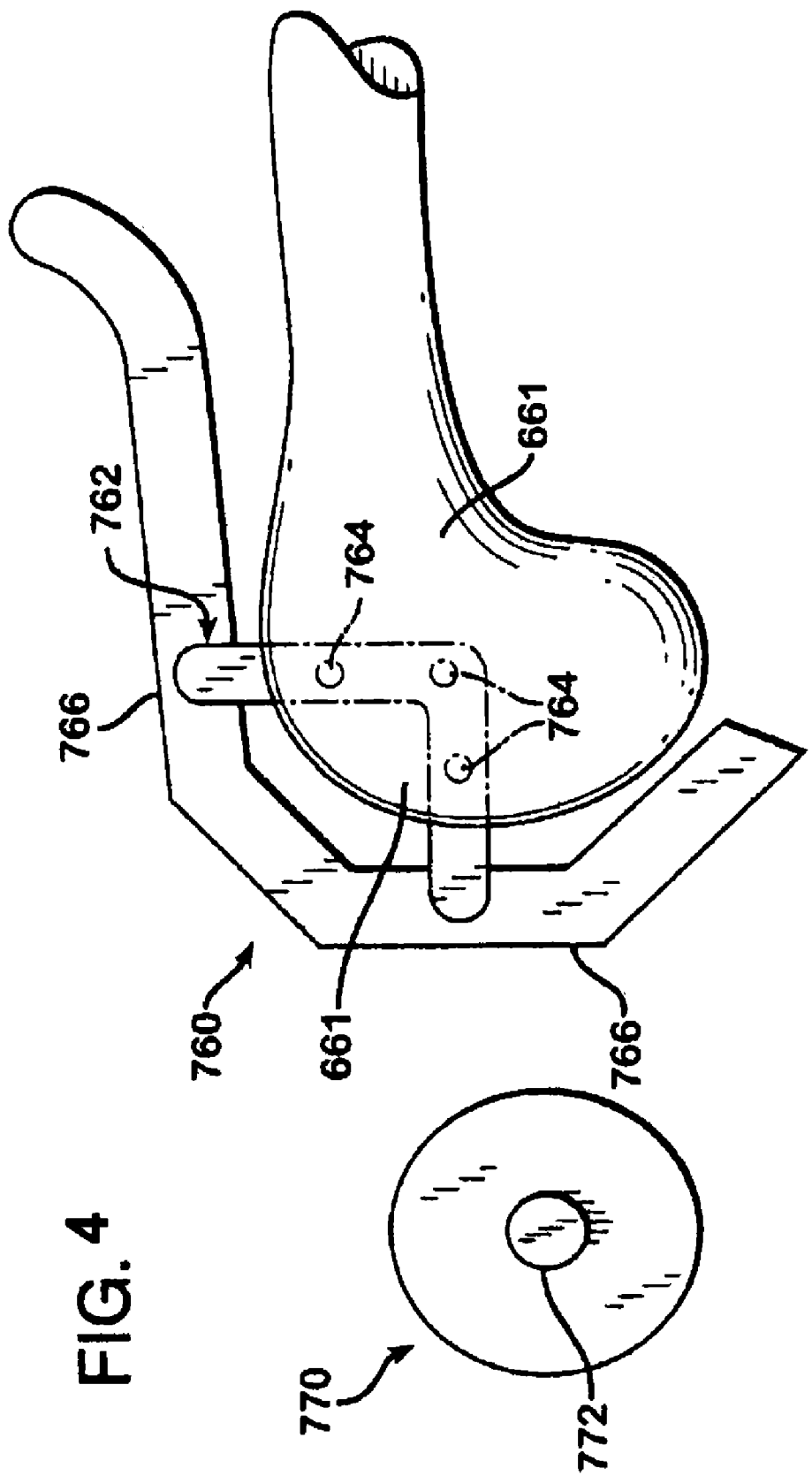
FIG. 4 is a side plan view of the pattern apparatus shown in FIG. 3 with the milling bit disengaged from the pattern apparatus.
Figure 5:
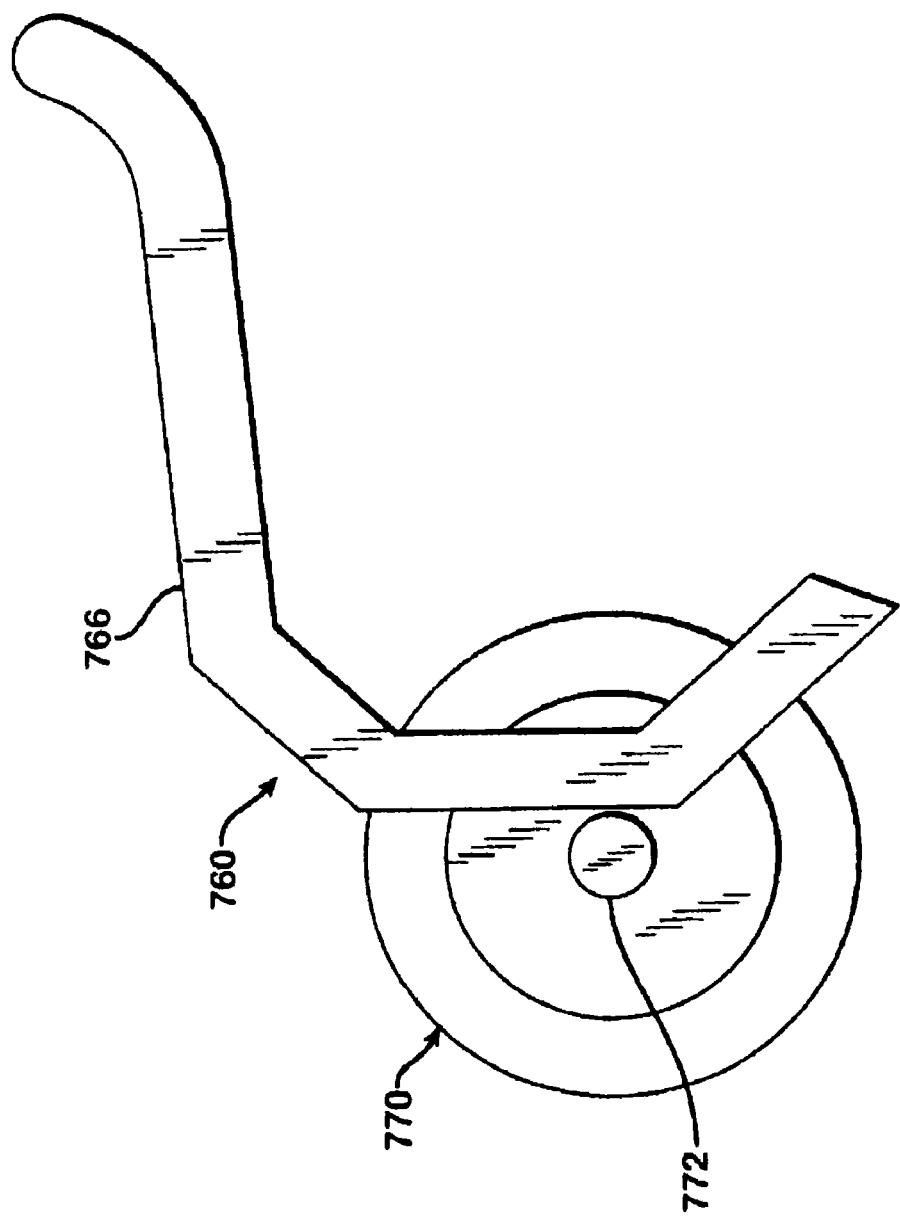
FIG. 5 is another side plan view of the pattern apparatus shown in FIG. 4 showing the milling bit engaged with the pattern apparatus.

As shown in FIGS. 3-5, in an alternate embodiment of the present invention for resecting a femur, the plates could take the form of a rail assembly, generally indicated at 760, positioned distally of the distal femur 661. The plates could be affixed to the femur by fixation arms 762, attached at one or more points to the rail assembly 760, and including fixation apertures 764 for receiving fixation screws or other fixation means for attaching the fixation arms 762, and hence the rail assembly 760, to a distal femur 661. The rail assembly 760 includes one or more guide rails 766 which match the shape of the desired resection, though the rails may be larger or smaller depending on the dimensions of the milling apparatus used and the positioning of the assembly 760 with respect to the femur. In the case that the assembly 760 includes two guide rails 766, as shown, an end rail 768 may be used to interconnect such guide rails 766. The end rail 768 could be replaced by a connection means similar to the crossbar apparatus 440, hereinbefore described. The rail assembly may be positioned on the distal femur in accordance with the teachings contained herein, or in any other manner known in the art. After alignment, according to any means disclosed herein or known or developed, and after fixation of the assembly to a femur, a milling bit 770 may be used to follow the guide rails 766 to resect the femur 661, the guide spindles 772, or bushings (not shown), of the milling bit 770, contacting and riding the guide rails 766. Importantly, the rail assembly 760 is attached to a femur and used in much the same way as the pattern plates previously described with the exception that the rail assembly can be positioned substantially distal of the femur, thereby potentially requiring less exposure and possibly resulting in less interference for placement thereof. The rail assembly 760 could further include an upper retaining rail for forming a slot or cutting path for capturing the milling bit therein. Additionally, it should be noted that any milling bit described herein could be used with rail assembly 760 including a curved profile milling bit.

Curvilinear Implants

Figure 6:
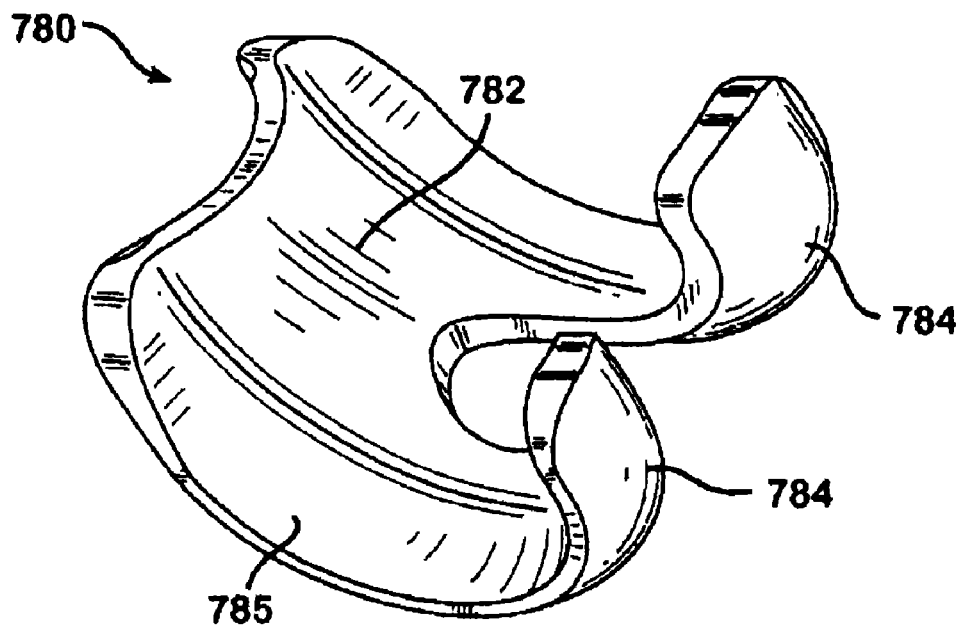
FIG. 6 is a perspective view of a femoral implant having a curved implant bearing surface.
Figure 7:
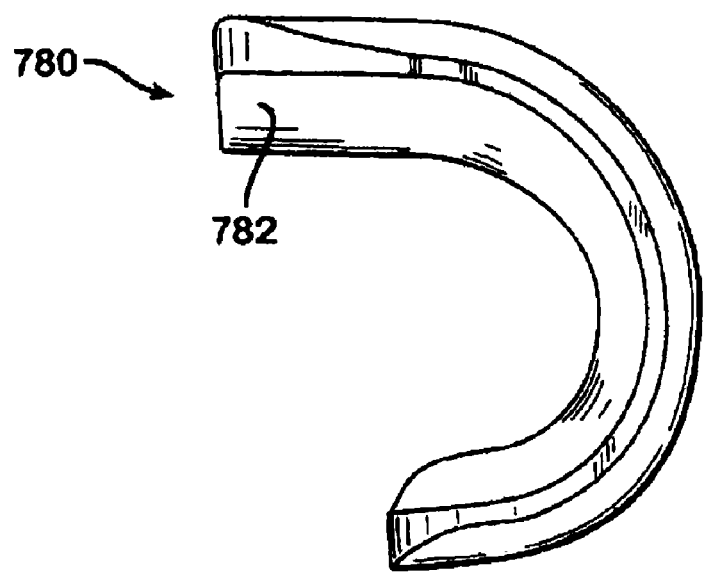
FIG. 7 is a side plan view of the femoral implant shown in FIG. 6.

As shown in FIGS. 6 and 7, an implant 780 may have curvilinear interior surfaces 782, as well as a more conventional curvilinear exterior surface. The particular example cited herein is a femoral implant used in total knee arthroplasty but the principles described herein may be applied to any application where foreign or indigenous material is affixed to an anatomic feature. The curvilinear bone surfaces necessary for proper fixation of such an implant may be generated through the use of the curvilinear milling or form cutter and the curvilinear cutting path means discussed herein. While it is possible to use multiple form cutters with differing geometries and, therefore, an implant with an internal geometry that varies along the cutting path from the anterior to the posterior of a femur, for the sake of intraoperative time savings a single form cutter is preferable.

The mediolateral cross-sectional internal geometry of such an implant, and therefore the necessary resected bony surfaces of the femur, are consistent about the cutting path in a single form cutter system. It should be noted that the implant may possess a notch between members 784 (posterior femoral implant condyles) in the areas approximately in between the distal and posterior femoral condylar areas to accommodate the posterior cruciate ligament and other factors. Because of the notch between the posterior femoral condyles it may not be necessary for the form cutter to cut any material in the notch. It may be desirable to provide outer flat surfaces 785 with an adjoining curvilinear surface 782 positioned therebetween. Other combinations of flat or curvilinear surfaces are also within the scope of the present invention.

Figure 15:
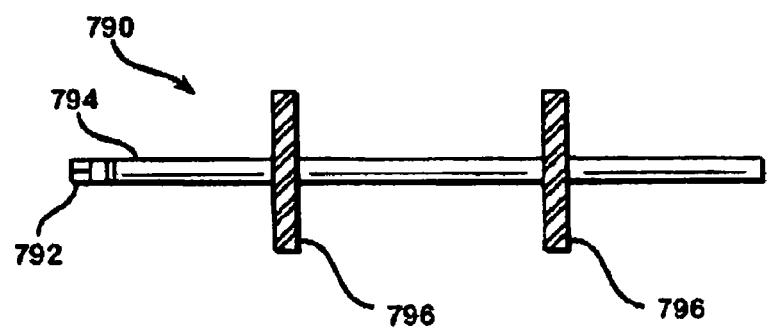
FIG. 15 is front plan view of another cutting apparatus for use in connection with the present invention.

Additionally, it may be advantageous to utilize a secondary form cutter as shown in FIG. 15 for use in creating a slot or slots in or near the distal area of the femur after it has been resected. Such a secondary cutter 790 would include engagement means 792 for engagement with driving means, and a shaft 794 carrying cutters 796 for cutting slots into the femur through one or more of the resected surfaces thereof. Through the inclusion of an additional or adjunct cutting path in the pattern means, it would be advantageous to utilize the form cutter to create the aforementioned slots to accommodate the fixation fins which may be molded as an integral part of the interior surface of the implant. These fins would provide mediolateral fixation stability in addition to that provided by the trochlear groove geometry of the implant. Further, the fins also provide for additional surface area for bony contact and ingrowth to increase implant fixation both in cemented and cementless total knee arthroplasty.

There are numerous advantages to the femoral component herein described. Foremost, it will allow for the thinnest implant cross-section possible (perhaps 3 mm to 6 mm in thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint. In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. Conversely, the curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e., when a cast is placed on a person's arm the muscles in that arm gradually weaken for lack of use.

Additionally, the curvilinear implant design may allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant will not only allow for the superior surface properties of ceramic, but also avoid the excessively thick cross-sections currently required for the use of the material.

This could result in a less expensive femoral implant because of the reduced amount of material needed for the implant, as well as an improved, more natural, and even stronger knee replacement. It may be desirable to vary the cross-section of the implant 780 to assist in seating the implant and to increase the strength and fit of the implant. The implants of the present invention having curvilinear implant surfaces could be fabricated of metal, plastic, or ceramic or any other material. Further, the thickness of the implants and the material required to fabricate the implant could be reduced as the implants are adapted to increasingly curvilinear surfaces. Also, it should be pointed out the such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Patella Shaping

Figure 10:
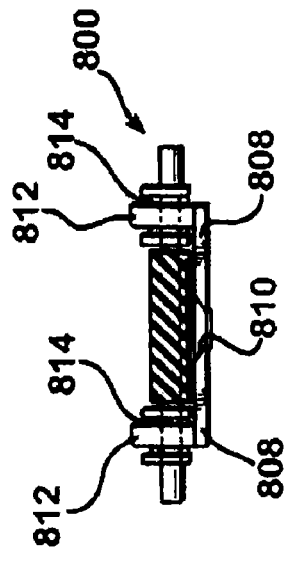
FIG. 10 is a front plan view of the patella resection apparatus shown in FIG. 8.
Figure 8:
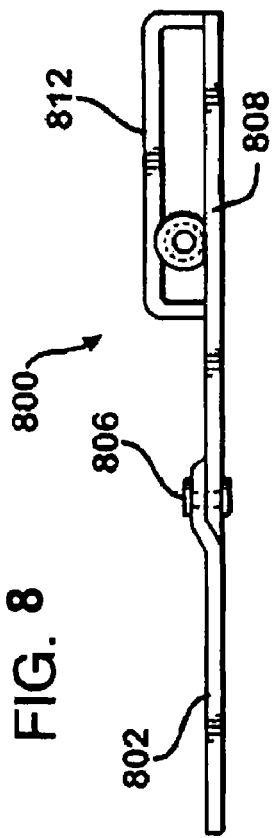
FIG. 8 is a side plan view of another embodiment of the pattern apparatus and positioning apparatus of the present invention for resecting a patella.
Figure 9:
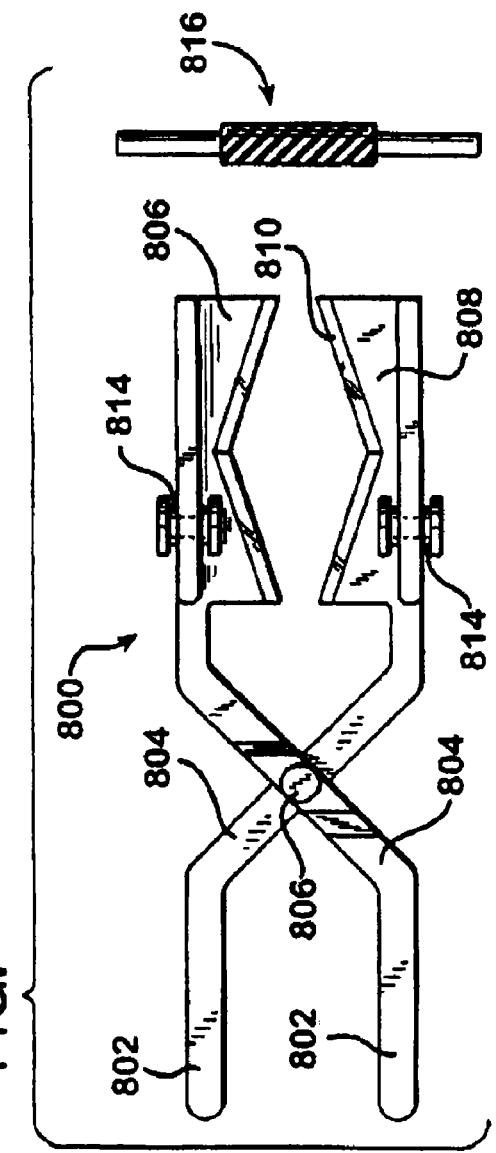
FIG. 9 is a top plan view of the patella resection apparatus shown in FIG. 8.

The apparatus for preparing a patella, as shown in FIGS. 8-10, comprises a plier-like patella resection apparatus generally indicated at 800. The patella resection apparatus 800 includes grip handles 802 for manipulating the apparatus, cross-over members 804 pivotally interconnected with each other by pin 806, and patella clamp members 808 extending from the cross-over members in parallel and facing relation. The patella clamp members 808 have beveled edges 810 for contacting and supporting a patella along the outer edges thereof. Guide member structures 812 are mounted on each of the patella clamp members 808 to form a retainer for a cutting means to follow a cutting path defined by the upper surface of the clamp members. Bushings 814 are captured within the retainer and the cutting path for receiving a cutting means 816 and guiding the cutting means 816 along the cutting path.

In preparing the patella, the pattern device may be an integral part of the positioning apparatus which is oriented and located by referencing the geometry of the patella itself as well as the structures of the patellofemoral mechanism to determine the location and orientation of a predominantly planar resection. The cutting device may then be employed to perform the resection of the patella by traversing the path dictated by the pattern device, thus dictating the final location and orientation of the patella prosthesis.

Bone Substitution and Shaping

Figure 11:
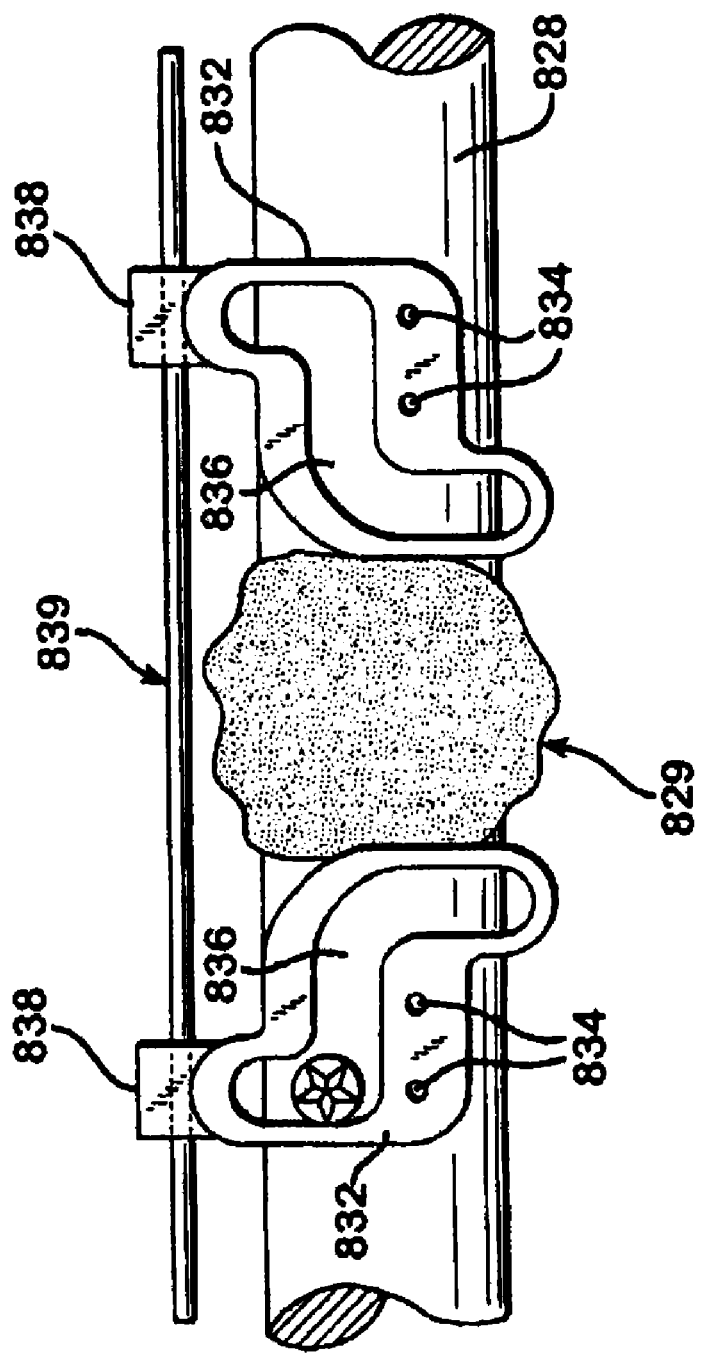
FIG. 11 is a perspective view of another embodiment of the pattern apparatus of the present invention for cutting a bone.

Referring now to FIG. 11, another embodiment of the pattern apparatus of the present invention for cutting bone is shown. This embodiment of the invention includes pattern plates 832 having cutting paths 836 described therein. The pattern plates 832 may be positioned on a bone 828 having a tumor or other pathology 829 associated therewith. The pattern plates 832 may be interconnected by crossbars 838 with opposing pattern plates (not shown) positioned on the opposite side of the bone 828. Further, each set of pattern plates 832 could be interconnected by means of positioning rod 839 extending between the crossbars 838 to maintain the relative location and orientation between the sets of pattern plates 832. The pattern plates can be positioned along the bone in accordance with what is known in the art, disclosed herein or hereafter developed. After the pattern plates are properly positioned, they can be affixed to the bone 828 with fixation means extending through fixation apertures 834. After the pattern plates are properly located and affixed to the bone, cutting can commence by traversing a cutting means along the cutting paths 836 of the pattern plates 832. By this step, the tumor or other pathology 829 can be cut from the bone 828 and a bone graft or other surgical procedure can be implemented to repair and/or replace the bone that has been cut. The benefits of cutting a bone with the pattern plates of the present invention include providing smooth and even cuts to the bone to facilitate fixation of bone grafts or other means for repairing and/or replacing bone. Further, the same pattern plates can be used to cut another identical sized and shaped bone for grafting to the first bone to replace the cut away bone.

Alternate Positioning and Alignment Guide

Figure 12:
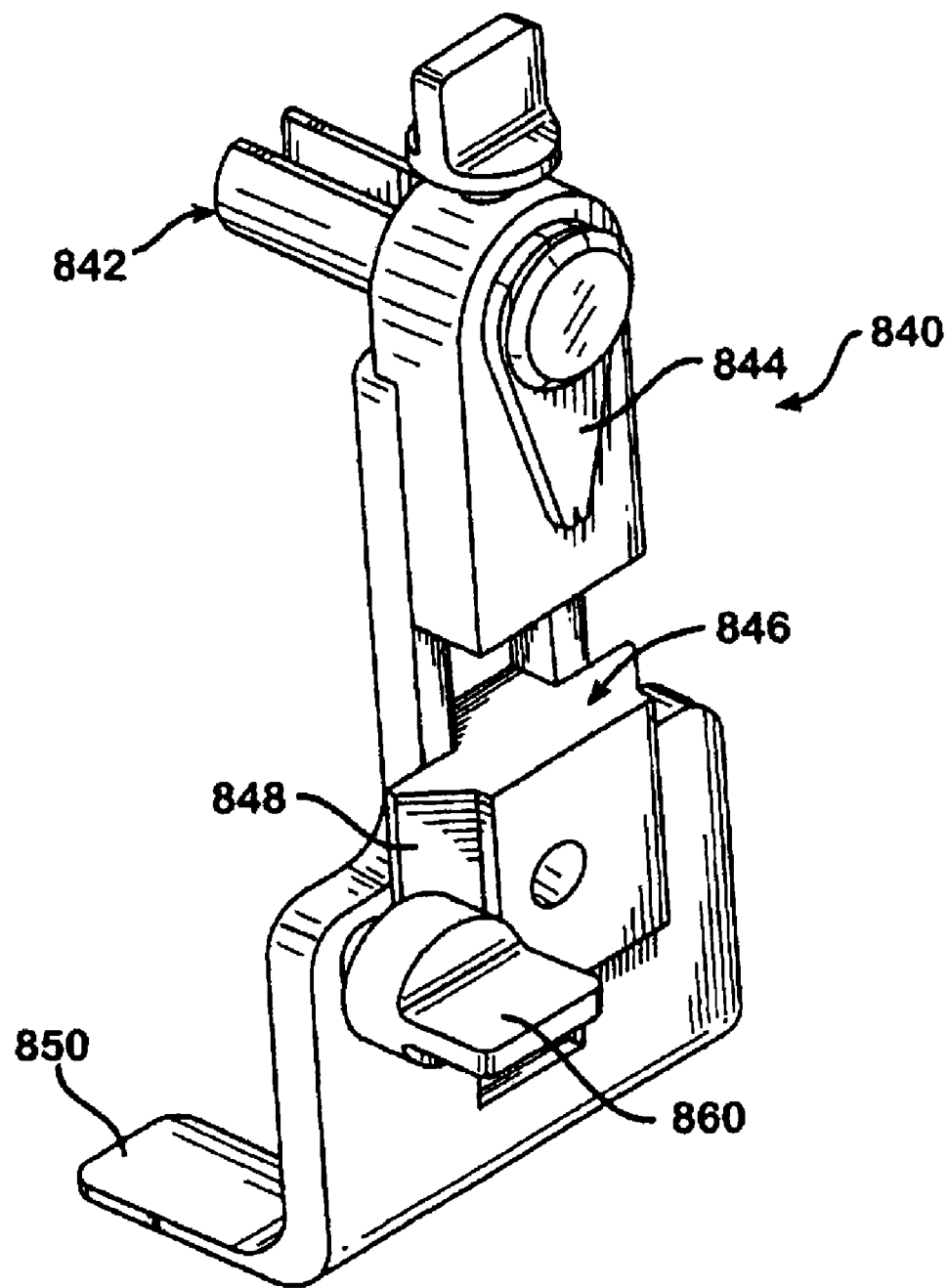
FIG. 12 is a perspective view of an embodiment of an alignment apparatus.

An alternate positioning and alignment guide is generally indicated at 840 in FIG. 12. The positioning body 840 comprises a crossbar linkage 842 and an alignment indicator 844 at an upper end thereof for interconnecting with a crossbar to align pattern plates interconnected with such crossbar. The positioning body 840 also includes an alignment block 846 for interconnecting with an intramedullary rod. The alignment block 846 is vertically movable along the positioning body 840 and can be locked into a desired position by means of lock screw 860 which bears against a flange 848 of the alignment block 846. The positioning body 840 further includes skids 850 for contacting the posterior surface of the distal femoral condyles for referencing same.

Unicondylar and/or Single Pattern Plate Support

Figure 13:
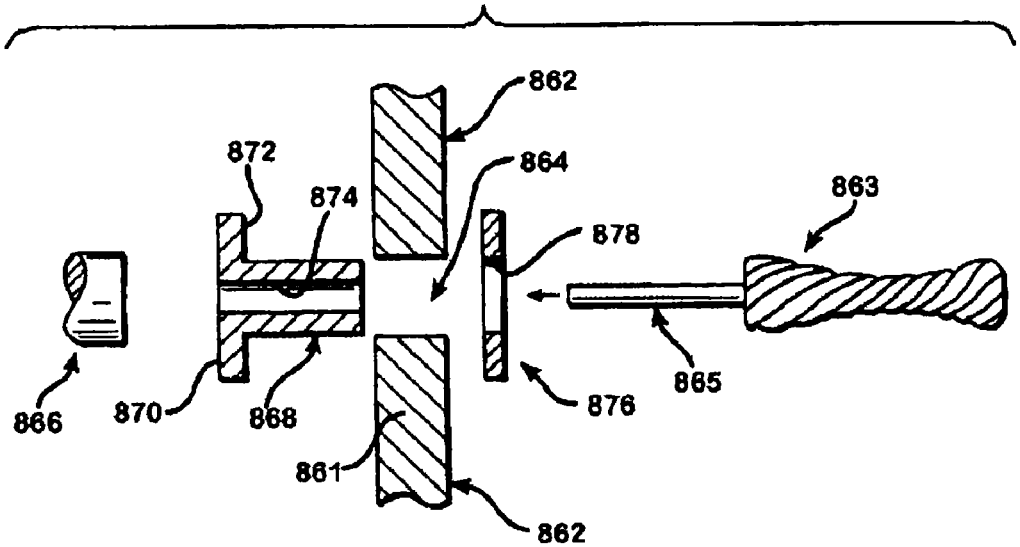
FIG. 13 is a partially exploded side plan view of another embodiment of the pattern apparatus of the present invention for cutting a bone.
Figure 14:
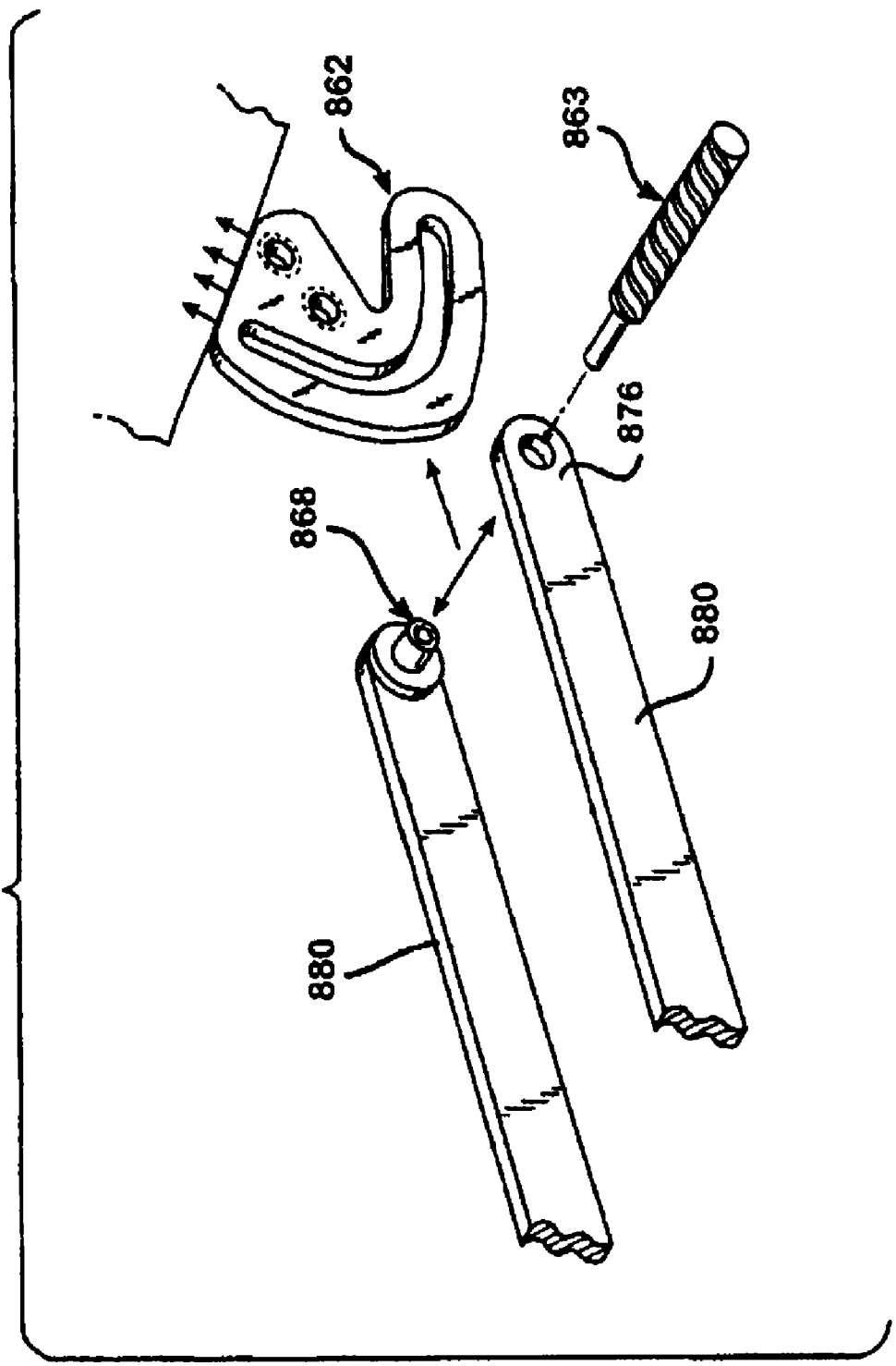
FIG. 14 is a partially exploded perspective view of the interconnection of a handle with milling bit for use in connection with pattern plate shown in FIG. 13.

As shown in FIGS. 13 and 14, one pattern plate of the present invention can be used by itself to guide a cutting means along a cutting path to cut a bone. Such an application is particularly useful for unicondylar resecting of a femur. Use of a single pattern plate 862 is facilitated by bushing 868 having an outer flange 870 with a bearing surface 872 and an internal bore 874 sized to receive a spindle 865 of a cutting tool therein. The bushing 868 is sized to fit into the cutting path 864 of the pattern plate 862, the bearing surface 872 of the flange 870 contacting the side of the pattern plate 862. Washer 876 includes a central bore 878 sized to receive the far end of the bushing 868 extending past the pattern plate 862, the washer bearing against the side of the pattern plate 862 opposite the side that the bearing surface 872 of the flange 870 of the bushing 868 bears against. Thus, the washer and the bushing co-act to form a stable link with a pattern plate. As shown in FIG. 14, this link can be fortified by means of bearing arms 880 interconnected with the bushing and the washer, or formed integrally as part thereof, which by pressure means are forced together to retain the bushing within the cutting path of the pattern plate. After the bushing is captured within the cutting path, the spindle of the cutting means can be inserted through the bushing and interconnected with means 866 for driving the cutting means. Alternatively, it should be pointed out that when using a single pattern plate to cut a bone, it may be desirable to support the cutting means at the pattern plate and also at the other end thereof. One could effect such desired support at the other end of the cutting means by a brace or other linkage interconnecting the other end of the cutting means with a secondary support or anchor means positioned on the opposite side of the bone or at another location.

Revisions

Conventional revisions require removal of the old implant and the referencing of uncertain landmarks. Revisions, by means of the present invention, allow for reference of the implant while it is still on the bone. One can obtain varus/valgus referencing, distal resection depth, posterior resection depth and rotational alignment by referencing the geometry of the implant with the alignment guide. An extramedullary alignment rod can be used to facilitate flexion/extension alignment. The fixation screws can then be advanced to touch the bone and mark their location by passing standard drill bits or pins through the cannulations in the fixation screws and into the bone. Then, the pattern and guide device are removed, the old implant removed, and the pattern device repositioned by means of the marked location of the fixation screws and then fixed into place. Accordingly, the cuts for the new implant, and thus the new implant itself, are located and orientated based off of the old implant. This results in increased precision and awareness of the final implant location and orientation as well as potential intraoperative time savings.

The particular example of the present invention discussed herein relates to a prosthetic implant for attachment to a femur in the context of total knee arthroplasty, i.e., a femoral implant. However, it should be pointed out that the principles described herein may be applied to any other applications where foreign or indigenous material is affixed to any other anatomic feature.

Figure 16:
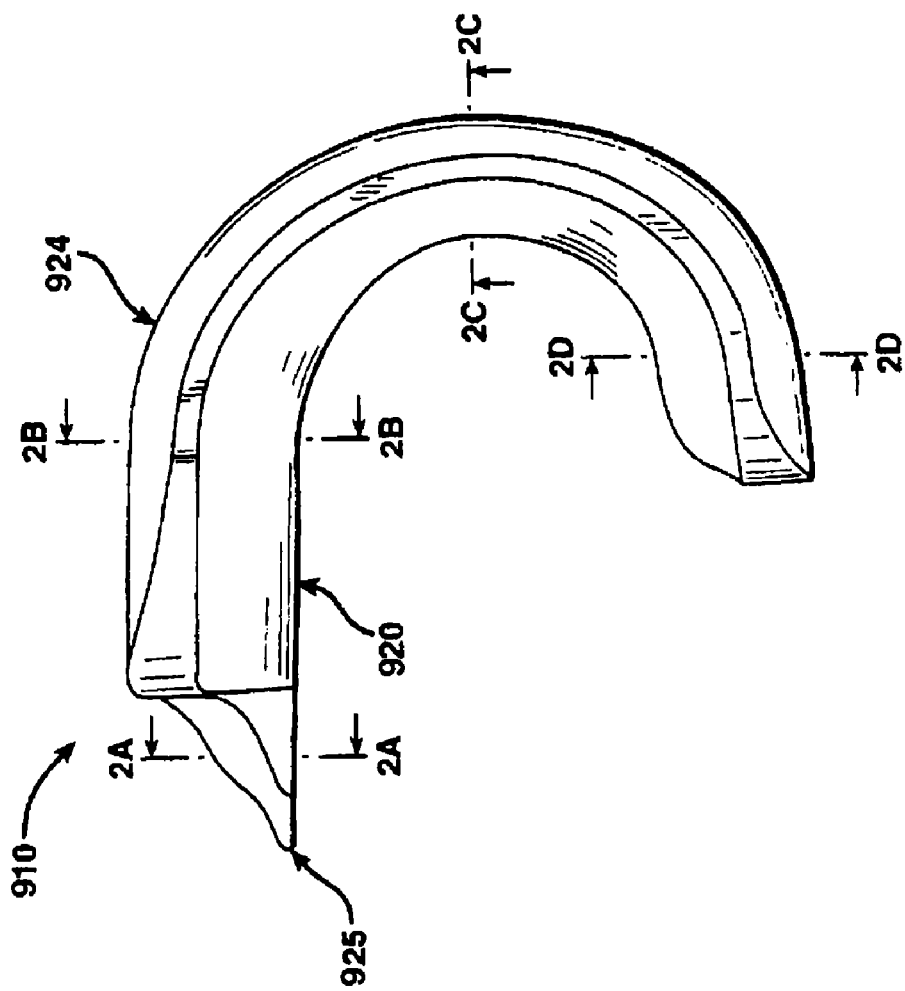
FIG. 16 is a side plan view of the femoral implant shown in FIG. 6, FIGS. 16A, 16B, 16C and 16D being sectional views taken along lines A-A, B-B, C-C and D-D of FIG. 16, respectively.
Figure 16A:
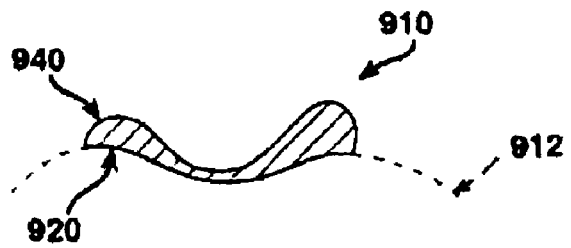
Figure 16B:
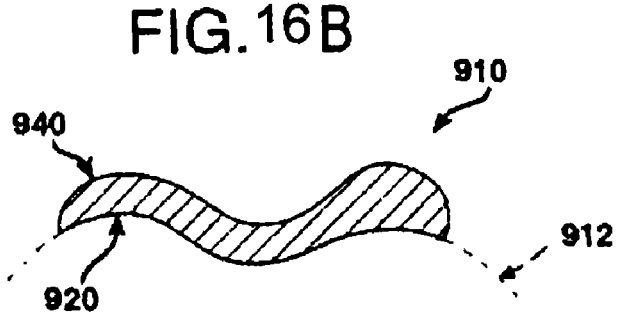
Figure 16C:
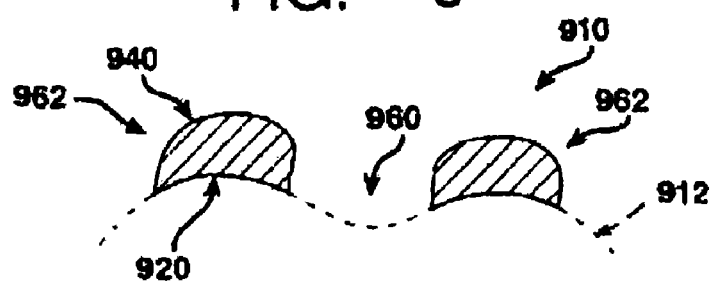
Figure 16D:
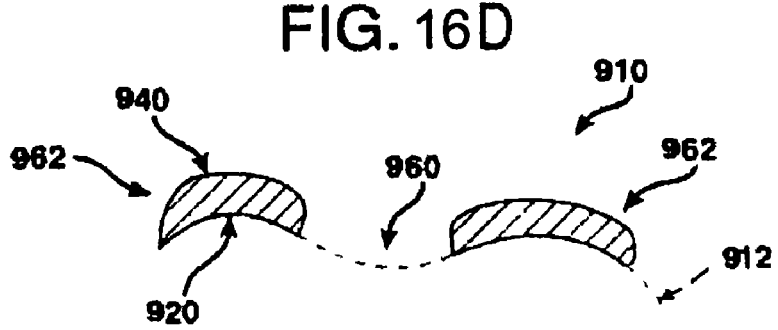

As shown generally in FIGS. 6 and 16, the implant apparatus of the present invention, generally indicated at 910, comprises curvilinear interior fixation surface 920 as well as curvilinear exterior bearing surface 940. Importantly, the implant of the present invention includes curvilinear surfaces extending from an anterior to a posterior area of the femur and/or implant, as is conventionally known, as well as curvilinear surfaces extending from a medial to a lateral area of the femur and/or implant to approximate the shape of natural femur. In other words, the fixation path (i.e., corresponding to the cutting path along which the milling bit rides to resect the femur; indicated by arrow A in FIG. 6) as well as the fixation profile (as one proceeds along the cutting profile orthogonally to the cutting path; indicated by arrow B in FIG. 6) are both predominantly curvilinear. As such, the cutting profile (arrow B) of the interior fixation surface 920 could include a curved or flat area 922 and another curved or flat area 924 therebetween. Preferably, the outer areas 922 are flat or relatively flat and the inner area 924 is curved to approximate the shape of a natural distal femur 912. It should be pointed out that the outer areas 922 could be curved, and the inner area 924 could also be curved, but embodying differing radii of curvature. Additionally, it should be pointed out that the geometry of the internal fixation surface 920 of the implant 910 could be varied as desired. As such, any combination of flat surfaces and curvilinear surfaces could be used. As shown in FIG. 16, and in more detail in FIGS. 16A, 16B, 16C and 16D, the cross-sectional thickness and mediolateral width of the implant of the present invention could vary along the implant 910. This variance results from merging a cutting tool to cut a bone, i.e., the implant 910 closely resembles in size and shape the material removed from the bone. Accordingly, the cut starts as a point 925 and grows in depth and width.

The curvilinear bone surfaces necessary for proper fixation of such an implant 910 may be generated through the use of the curvilinear milling bit or form cutter and the curvilinear cutting path means discussed in the previous related applications set forth herein, the entire disclosures of which are expressly incorporated herein by reference. Basically, the milling bit has a profile resulting in form cutter configuration which is concentric about its longitudinal axis to effect a curvilinear cutting profile for receiving the implant of the present invention. One embodiment of such a form cutter is shown in FIGS. 3 and 17. While it is possible to use multiple form cutters with differing geometries and therefore an implant 910 with an internal geometry that varies along the cutting path from the anterior to the posterior of a femur, for the sake of intraoperative time savings, a single anatomically optimal form cutter is preferable.

The form cutter shown in FIGS. 3 and 17 comprises a cutting guide 950 having cutting paths 952 interconnected by member 954. A milling bit 960 having cylindrical milling areas 962 at the ends, and a curved milling area 964 at the center could be used. Of course, the milling areas carry cutting teeth. Spindles 961 interconnected at each end of the milling bit 960 could engage and ride the cutting path 952 of the cutting guide 950. The milling bit 960 is then guided along the cutting path 952 by means of a handle. Importantly, the shape of the milling bit 960 could be varied as desired to create a resection having a desired cutting path as well as a desired cutting profile.

The mediolateral cross-sectional internal geometry of such an implant 910, and therefore the necessary resected bony surfaces of the femur, are consistent about the cutting path in a single form cutter system. It should be noted that the implant 910 may possess a notch 970 between members 972 (posterior femoral implant condyles) in the areas approximately between the distal and posterior femoral condylar areas to accommodate the posterior cruciate ligament, as well as for other reasons. Because of the notch 970 between the posterior femoral condyles, the form cutter may not cut any material in the notch 970.

Additionally, it may be advantageous to utilize a secondary form cutter as shown in FIG. 15 for use in creating a slot or slots in or near the distal area of the femur before or after it has been resected. Such a secondary cutter 790 would include engagement means 792 for engagement with driving means, and a shaft 794 carrying one or more cutters 796 for cutting slots into the femur through one or more of the resected surfaces thereof.

Figure 18:
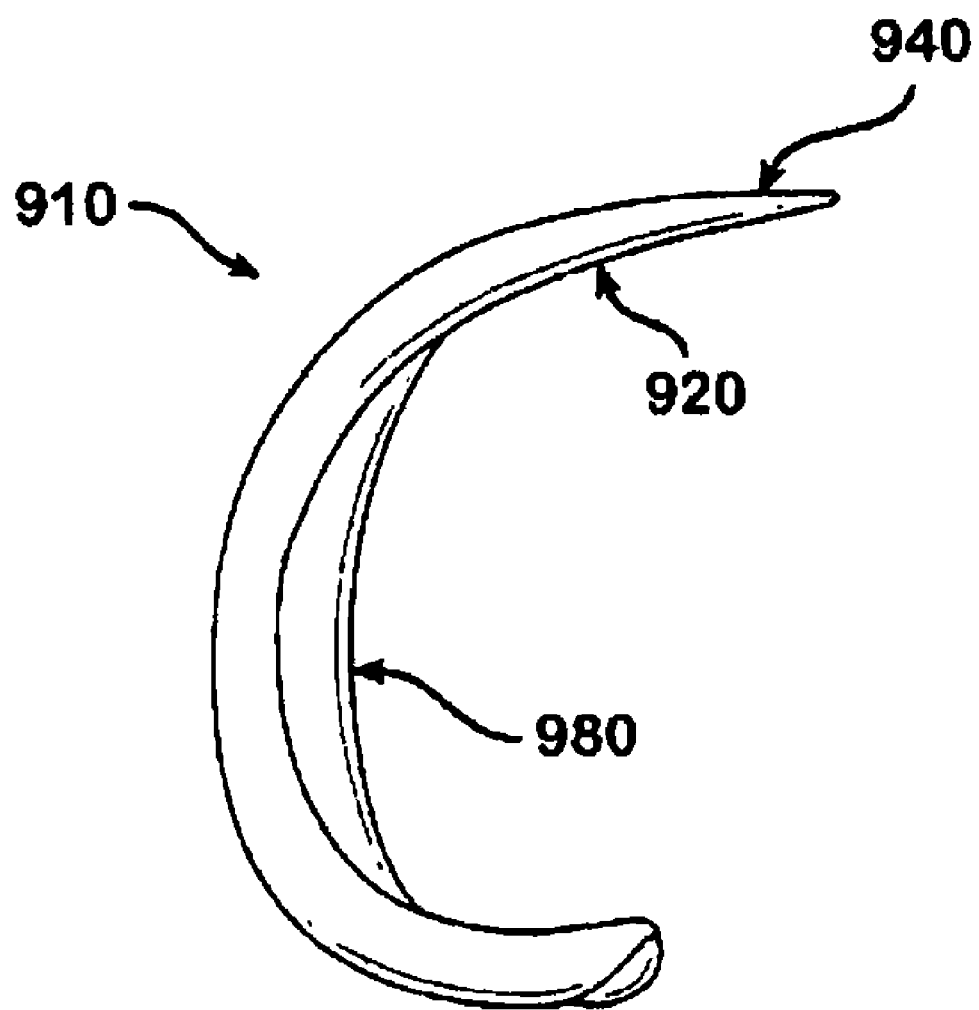
FIG. 18 is a side plan view of another embodiment of the femoral implant shown in FIG. 6.
Figure 19:
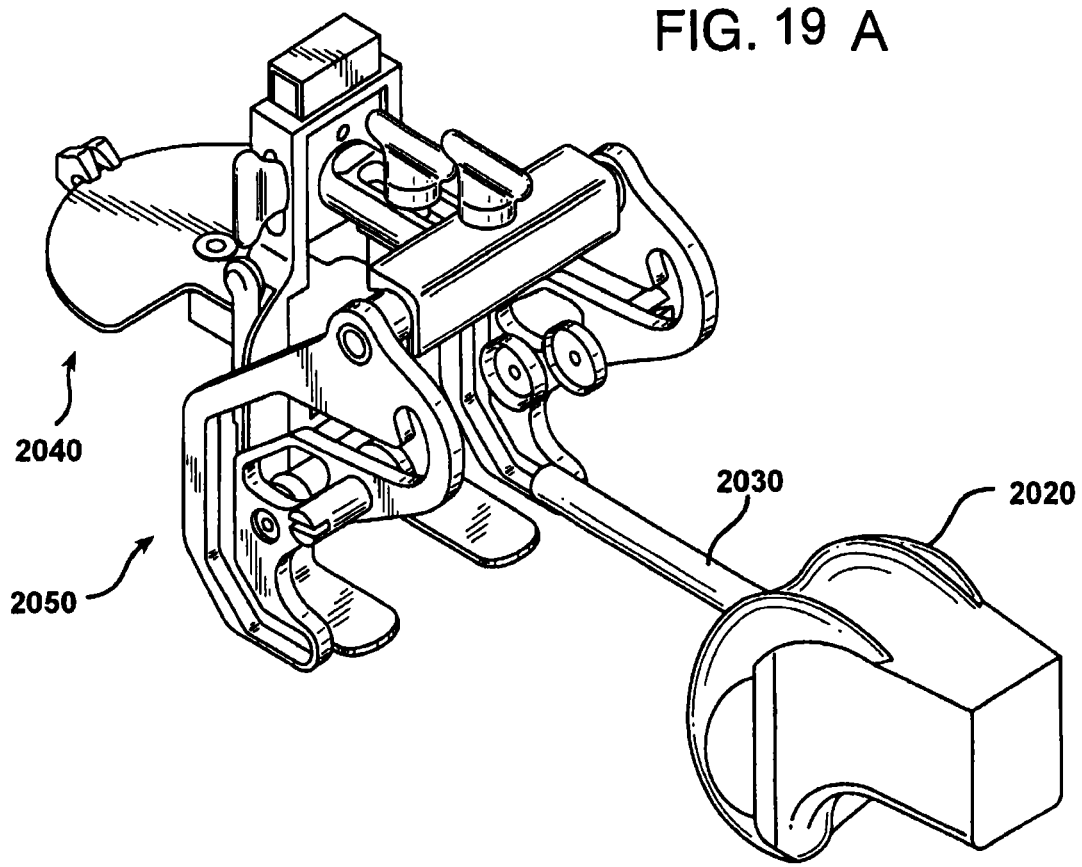
FIG. 19A is a perspective view of an embodiment of a femoral resection apparatus having cutting guides.
FIG. 19B is a side view thereof.
Figure 19:
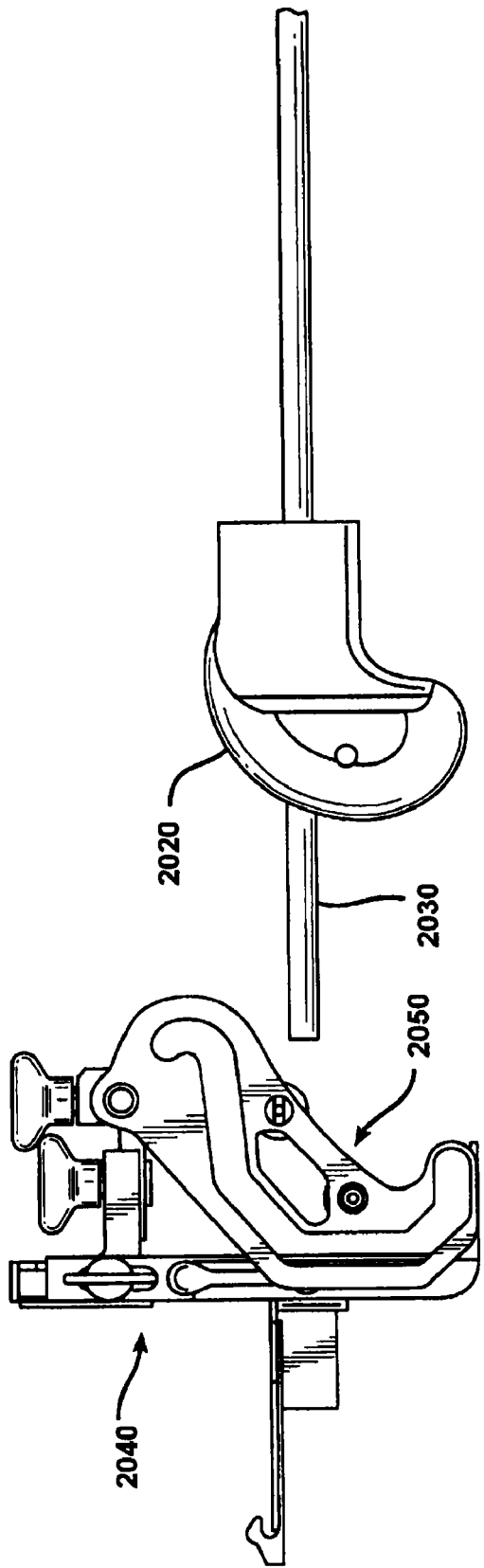
Figure 20:
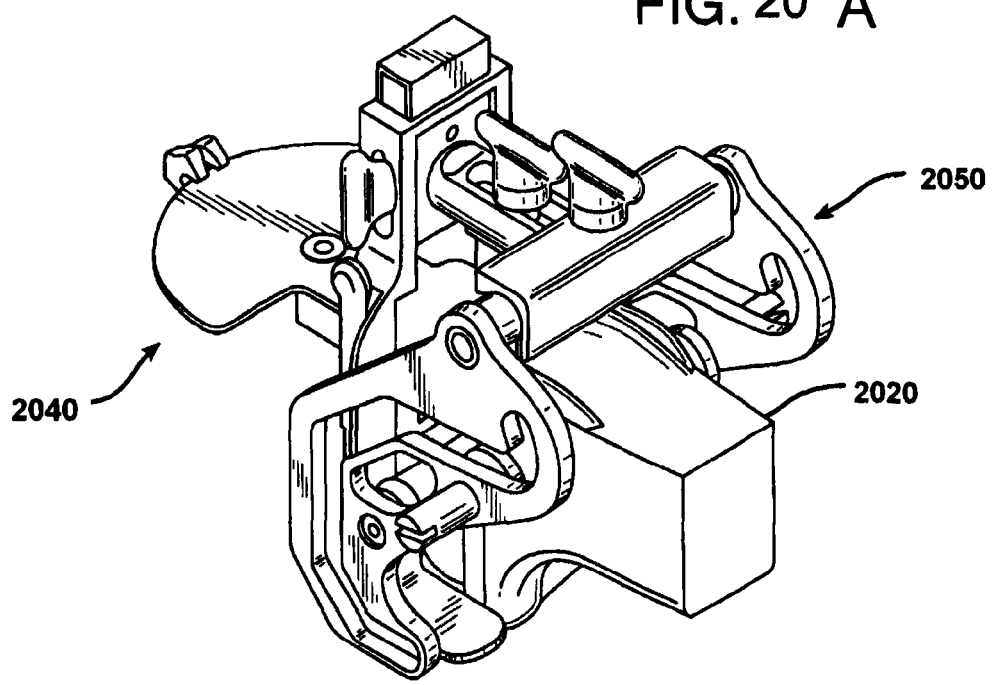
FIG. 20A is a perspective view of the apparatus shown in FIG. 19 affixed to a femur to be resected.
FIG. 20B is a side view thereof.
Figure 20:
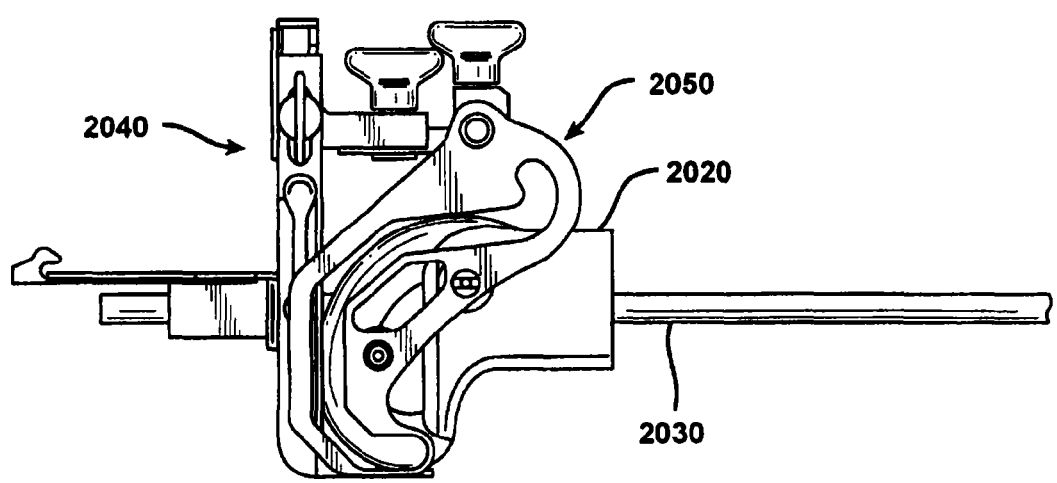
Figure 21:
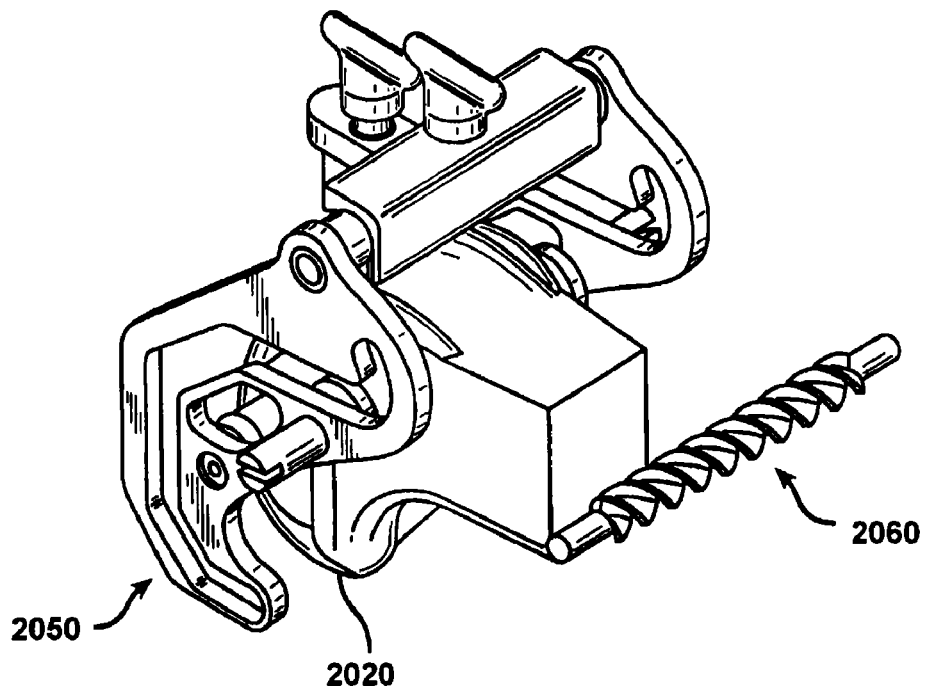
FIG. 21A is perspective view of the cutting guide portion of the femoral resection apparatus shown in FIG. 19 affixed to a femur to be resected, along with a cutting tool.
FIG. 21B is a side view thereof.
Figure 21:
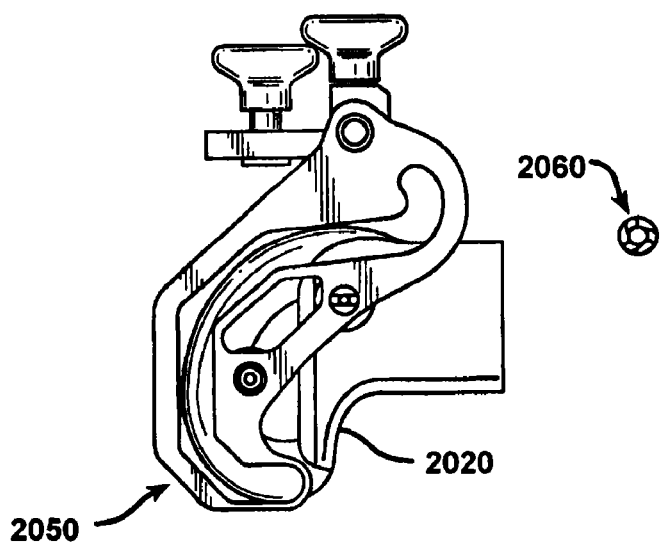

Through the inclusion of an additional or adjunct cutting path in the pattern means, it would be advantageous to utilize the form cutter to create the aforementioned slots in the distal femur to accommodate the fixation fins which may be molded as an integral part of the interior surface of the implant 910. An implant with fixation fins is shown in FIG. 18 and the fins extend in both an anterior to posterior direction and a distal to proximal direction. The fins 980 would provide mediolateral fixation stability in addition to that provided by the trochlear groove geometry of the implant 910. Further, the fins also provide for additional surface area for bony contact and ingrowth to increase implant fixation both in cemented and cementless total knee arthroplasty.

Figure 1B:
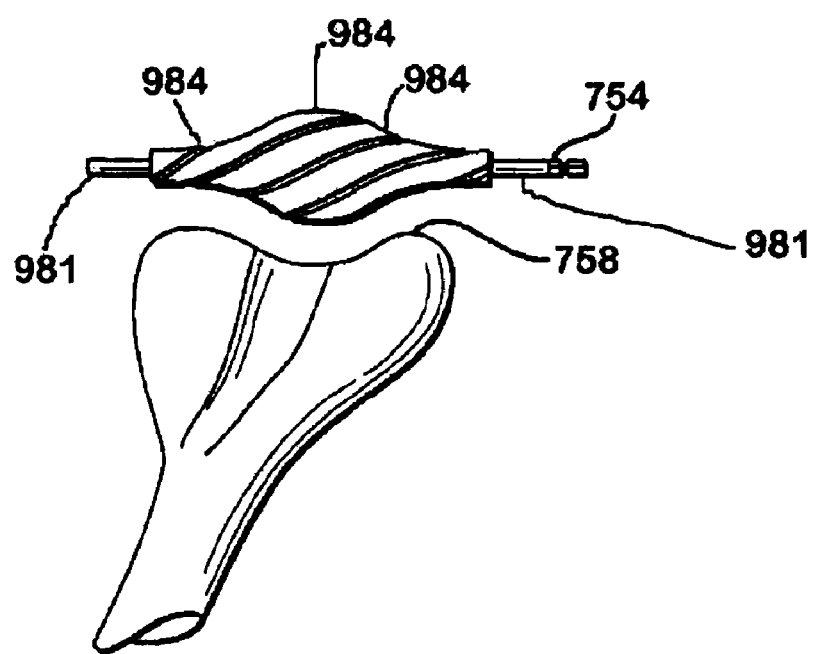

FIG. 1b shows another embodiment of a milling bit, generally indicated at 754 for creating a curvilinear cutting path and curvilinear cutting profile in femur 756. In this embodiment, the transition from a first cutting area 984 to a second cutting area 986 is continuous and smooth. This milling bit 754 also includes spindles 981 at the ends thereof for engagement with pattern means to guide the milling bit along a cutting path.

There are numerous advantages to the femoral component herein described. Foremost, it will allow for the thinnest implant cross-section possible (perhaps 3 mm to 6 mm in nominal thickness) and therefore necessitate the removal of the least amount of viable osseous tissue. This is especially critical in situations where the probability of revision surgery is high and the amount of viable bone available for revision implant fixation and apposition is a significant factor in the viability of the revision procedure. Since the form cutter configuration allows for similar amounts of tissue to be removed from the trochlear groove, the bony prominences surrounding the trochlear groove, the femoral condyles, and the other articular surfaces of the femur, the external geometry of the femoral implant can be optimized for patellofemoral articulation as well as tibiofemoral articulation. In essence, the kinematics of the artificial joint could be made to be as close as possible to that of a healthy, natural knee joint.

In addition, the curvilinear geometry of the implant dramatically decreases the stress risers inherent in conventional rectilinear femoral implants and allows for a thinner cross-sectional geometry while potentially increasing the resistance of the implant to mechanical failure under fatigue or impact loading. The implant could have a relatively consistent cross-sectional thickness throughout the implant, or it could be varied as desired.

The curvilinear geometry of the implant may also allow for an advantageous reduction in the flexural rigidity of the implant which may result in avoidance of the "stress-shielding" inherent in rigid implant designs. Stress shielding being a phenomenon that may occur when living bony tissue is prevented from experiencing the stresses necessary to stimulate its growth by the presence of a stiff implant. This phenomenon is analogous to the atrophy of muscle tissue when the muscle is not used, i.e., when a cast is placed on a person's arm the muscles in that arm gradually weaken for lack of use.

Further, the curvilinear implant of the present invention could allow for the use of a ceramic material in its construction. Since ceramics are generally relatively weak in tension, existing ceramic implant designs contain very thick cross-sections which require a great deal of bony material removal to allow for proper implantation. Utilization of ceramics in the curvilinear implant would not only allow for the superior surface properties of ceramic, but also avoid the excessively thick cross-sections currently required for the use of the material.

The curvilinear implant of the present invention could result in a less expensive femoral implant because of the reduced amount of material needed for the implant, as well as an improved, more natural, and even stronger knee replacement. It may desirable to vary the cross-section of the implant to assist in seating the implant, to increase the joint kinematics and to increase the strength and fit of the implant. The implant of the present invention could be fabricated of metal, plastic, or ceramic or any other material or combination thereof. Further, the thickness of the implants and the material required to fabricate the implant could be reduced as the implants are adapted to increasingly curvilinear surfaces. Also, it should be pointed out that such implants with curvilinear implant surfaces require less bone to be removed to obtain a fit between the implant and the bone. Finally, it should be noted that curvilinear milling bits hereinbefore described would work well for preparing a bone to receive an implant with curvilinear interior implant surface.

Importantly, by using a milling bit having a curved profile, one can cut a femur to resemble the natural shape of the femur, i.e., the resected femur would include condylar bulges and a central notch. This would reduce the amount of bony material that must be removed from the femur while maintaining the structural integrity of the femur. Of course, any prosthetic implant used for attachment to a femur resected by the curved profile milling bit would necessarily have an appropriately contoured inner fixation surface for mating with contoured surface of the femur. Additionally, it should be noted that the curved profile milling bit could have one or more curvilinear bulges along the length thereof, as shown in FIGS. 3 and 17, or alternatively, could have one or more bulges discretely formed along the length thereof.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

In the process of developing the basic instrumentation concept discussed in parent U.S. Pat. No. 5,514,139, it was necessary to attach the cutting guides to the femur in a very robust manner in order to prevent deflection or movement of the cutting guide during the cutting process. The concept utilized to avoid cutting guide movement involved a cannulated screw which applied opposable compression to the medial and lateral sides of the femur while a fixation nail was driven through the cannulae to complete fixation. In the earliest cadaveric evaluations of the instrumentation, it was noted that the fixation thus attained was robust enough to allow the 'patient' to be lifted from the table using the guide. Somewhat accidentally, it was also noted that the fixation of the guide to the bone in this manner also avoided any errors in cutting guide placement. Since the cannulated fixation screws were brought directly into contact with the bone surfaces, the moment arm the pins could be subjected too was minimized and thus prevented mal-alignment of the cutting guides. The teachings of the related parent applications are generally discussed herein with reference to FIGS. 19-23.

Figure 22:
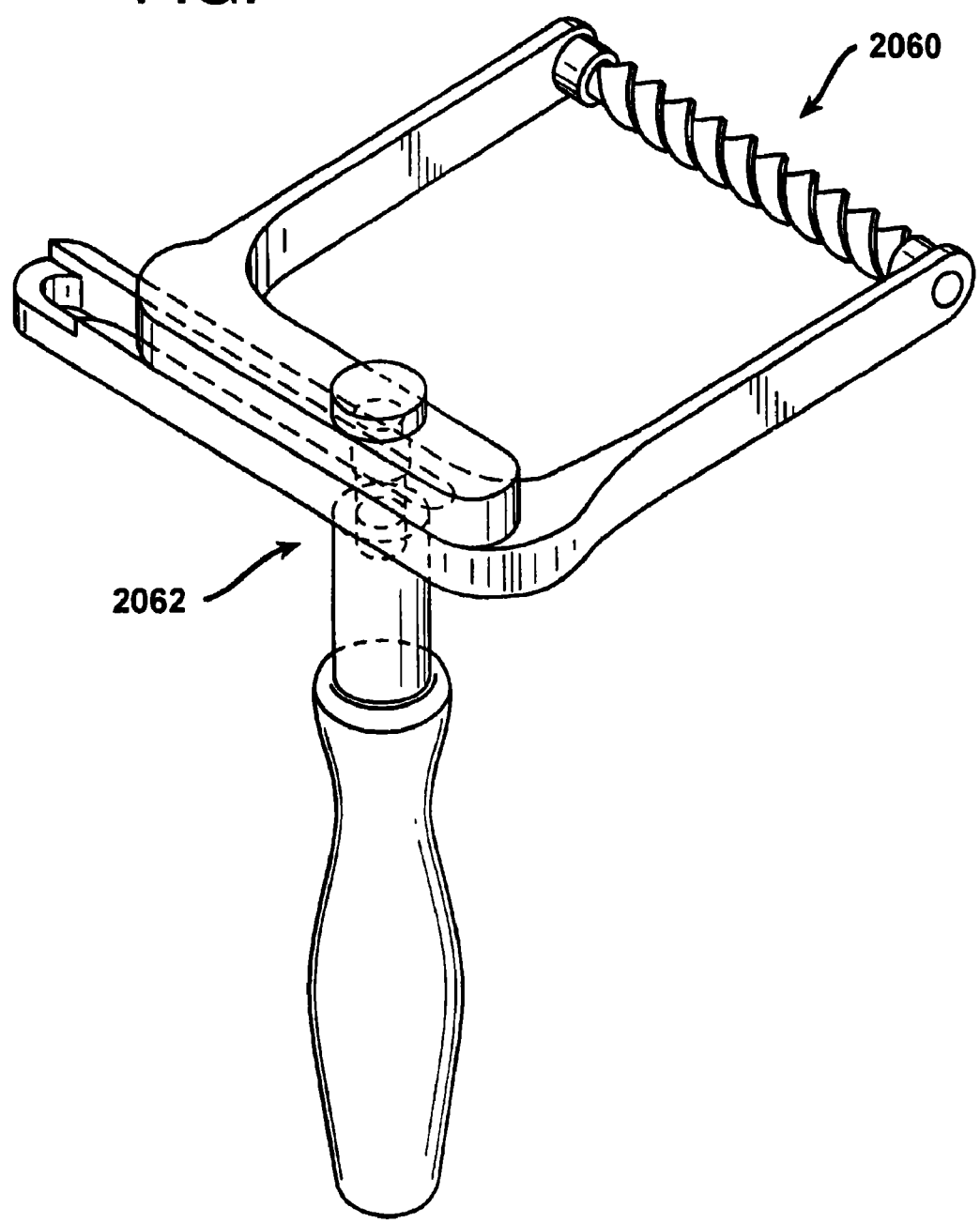
FIG. 22 is a perspective view of a cutting tool and guide handle for resecting a femur.
Figure 23:
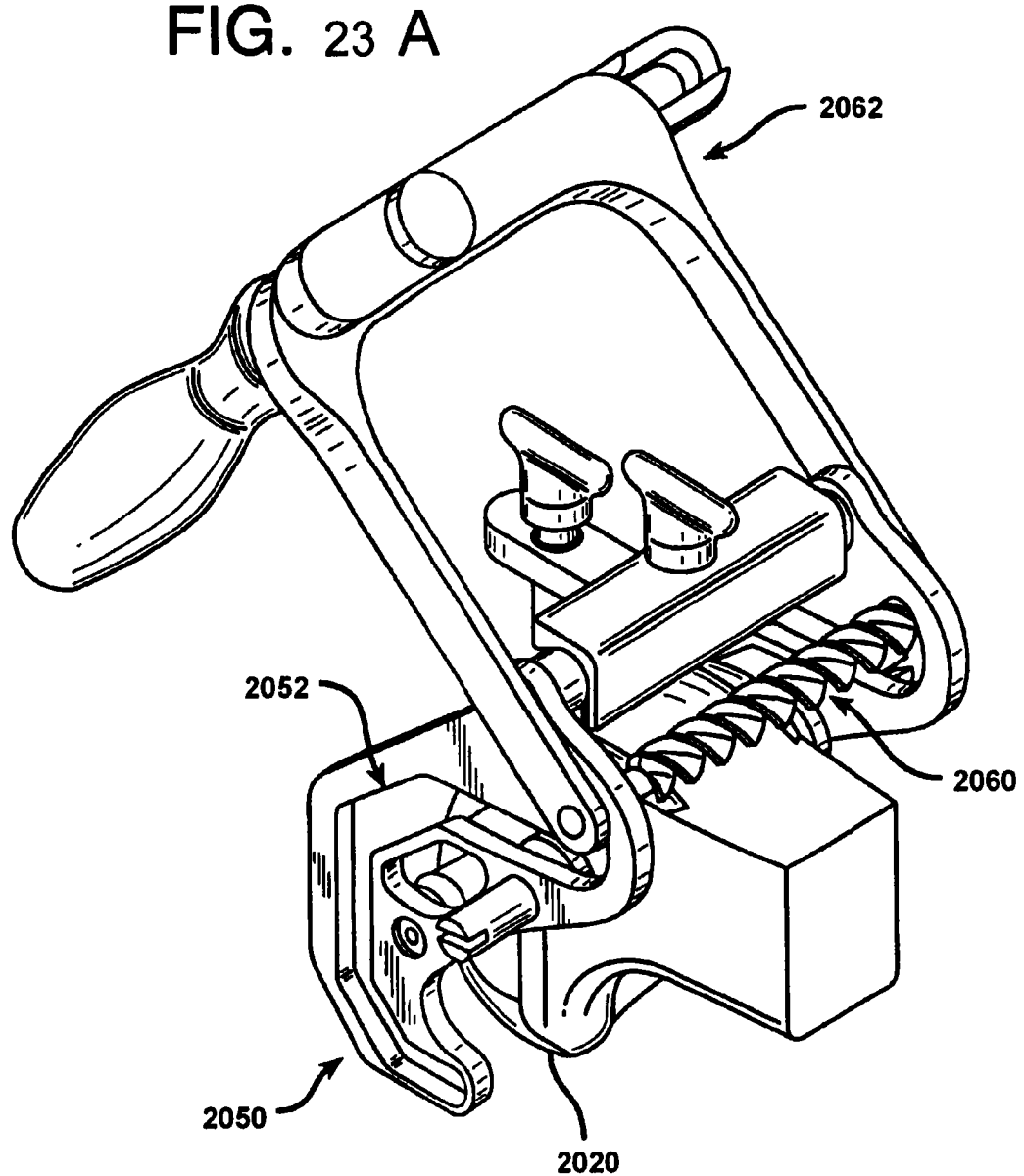
FIG. 23A is a perspective view of the cutting tool interconnected with the cutting guide shown in FIG. 22.
FIG. 23B is a side view thereof.

FIGS. 19A and 19B show the first step in this technique where the intramedullary rod 2030 is introduced into the IM canal of the femur 2020 while the alignment guide 2040 and cutting guide 2050 are assembled and then adjusted to the proper relative locations and orientations. FIGS. 20A and 20B show the cutting guide 2050 and the alignment guide 2040 positioned about the femur 2020. The cutting guide 2050 is then fixed to the femur 2020 using cannulated fixation screws and fixation nails. The alignment guide 2040 and intramedullary rod 2030 are then removed. FIGS. 21A and 21B show the cutting guide 2050 fixed to the distal femur 2020 (fixation nails not shown) and the milling tool 2060. FIG. 22 shows the milling tool 2060 and the milling handle 2062. FIGS. 23A and 23B show the milling tool 2060 and milling handle 2062 properly articulated with the cutting guide 2050 prior to initiating the cutting process. The cutting process includes attaching a driver (a DC or AC drill) to the milling tool 2060 and to manually direct the milling tool 2060 and milling handle 2062 through the cutting path 2052 of the cutting guide 2050.

This technique works well in cadaveric evaluations. Interestingly, there is an inability of the milling tool to cut the collateral ligaments or the posterior cruciate ligament, likely due to the amount of surface area of the milling tool in contact with the ligament. An oscillating sawblade brings finely pointed teeth, teeth whose leading tips are directed at 90 degrees to the ligament fibers, directly into contact with the ligaments, and thus a very small force is required for the very small surface area of the teeth to be forced through the ligament. Another way of stating this is that the local pressure induced by the teeth is very high even when motivated by very small forces due the extremely small surface area of contact between the teeth and the ligament. The milling tool, on the other hand, has teeth which are essentially smooth, and which have much larger areas in contact with the ligament, and are oriented tangentially to the fibers and body of the ligament so that even at the maximum force levels induced by manually pushing the milling handle and milling tool into a ligament (perhaps 25 to 50 lbs.), the ligaments are not cut.

It should be noted that conventional milling was used in evaluations. Conventional milling, in the case of this instrumentation, dictates that the milling bit rotates in the opposite of the direction from the cutting direction to maximize both control during cutting and the smoothness of the resulting surfaces. Climb milling, the opposite of conventional milling, is potentially problematic and may be avoided by utilizing a one way clutch between the milling tool and the drill driving the milling tool thus avoiding even accidental use of climb milling.

FIGS. 24-27 show a variation on the methods and apparatus of the parent applications which improves the accuracy and ease of use of the instruments. FIGS. 24A and 24B show the alignment guide 2140 connected to a drill guide 2142. The drill guide 2142 has hole locators 2144 for locating positioning hole(s) in the medial and lateral sides of the femur 2020 that correspond to the fixation features (nubs or cannulated screws) of the cutting guide, as will be described.

FIGS. 25A and 25B show the drill guide 2142 located about the sides of the distal femur 2020. At this point a drill is used to drill through the hole locators 2144 in the drill guide 2142 to create positioning hole(s) in the medial and lateral sides of the femur. It should be noted that it is possible to place only the distal-most positioning hole in the femur using the drill guide 2142, and then to rely on an extramedullary reference to determine the appropriate flexion-extension alignment for the anterior-most fixation point.

Figure 26:
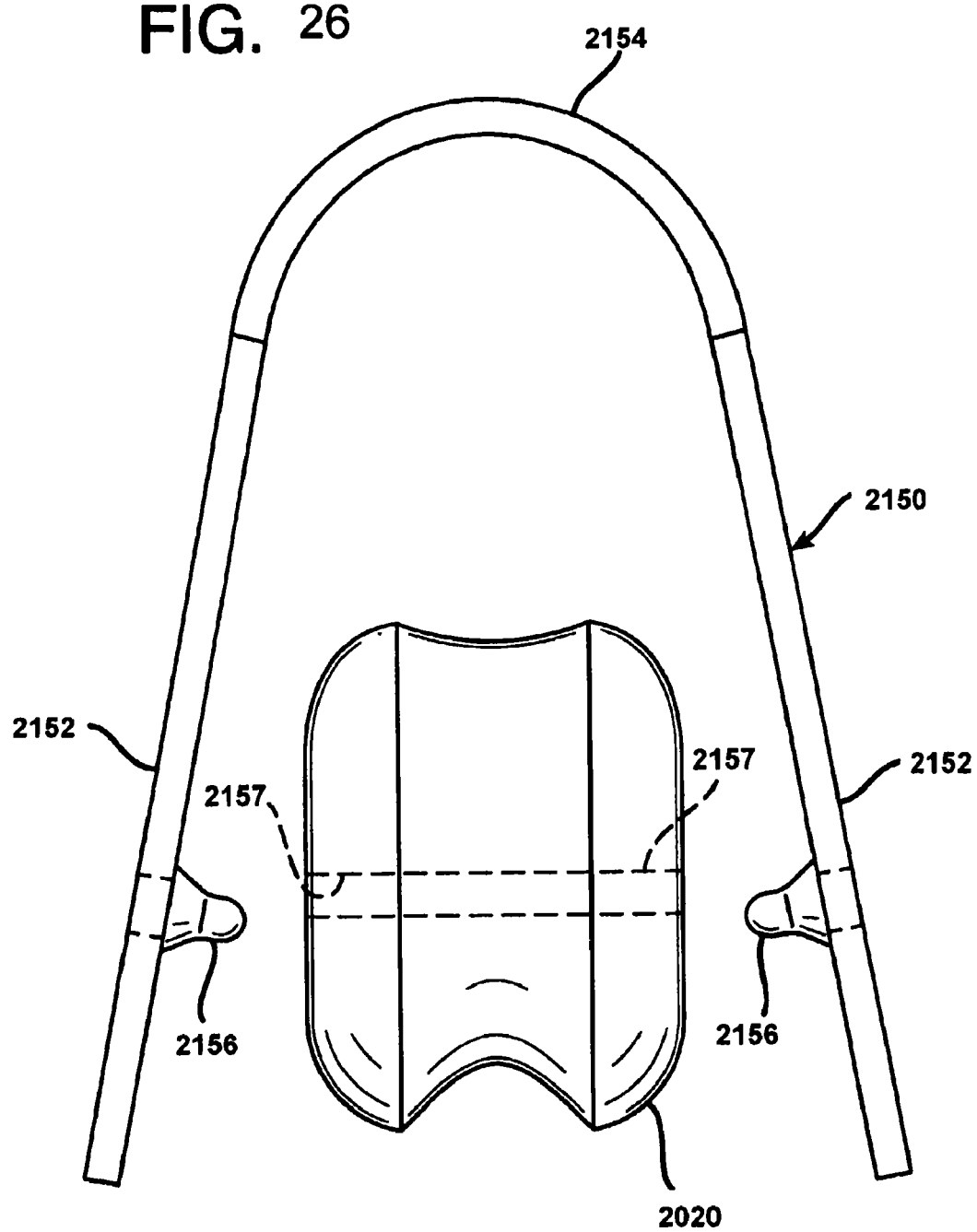
FIG. 26 is a front view of a cutting guide of the present invention positioned for attachment to a femur to be resected.
Figure 27:
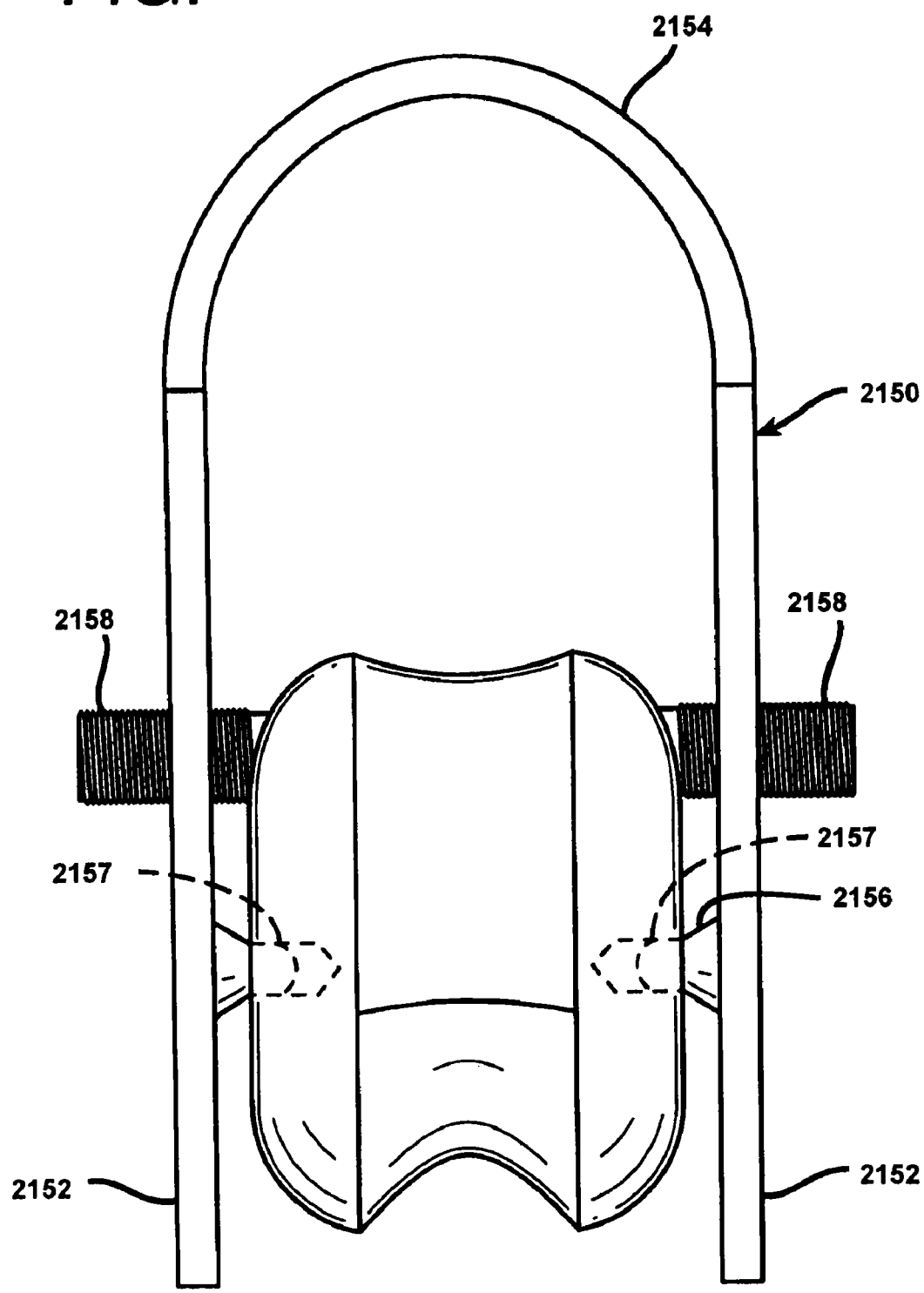
FIG. 27 is a front view of the cutting guide shown in FIG. 26 attached to a femur to be resected.

FIG. 26 shows the cutting guide 2150 of this embodiment, having side plates 2152 with a cutting path described therein, and an upper bridge 2154 interconnecting the cutting plates 2152. To position the cutting guide 2150 on a femur to be resected 2020, the side plates are spread apart to allow for the introduction of fixation nubs 2156 into the positioning holes 2157 created previously in femur 2120. FIG. 27 shows the fixation nubs 2156 engaged in the positioning holes 2157, and additionally, cannulated fixation screws 2158 fixed to the medial and lateral sides of the femur. The step of cutting the distal femur 2020 is essentially identical to the techniques shown in FIG. 23.

Figure 28:
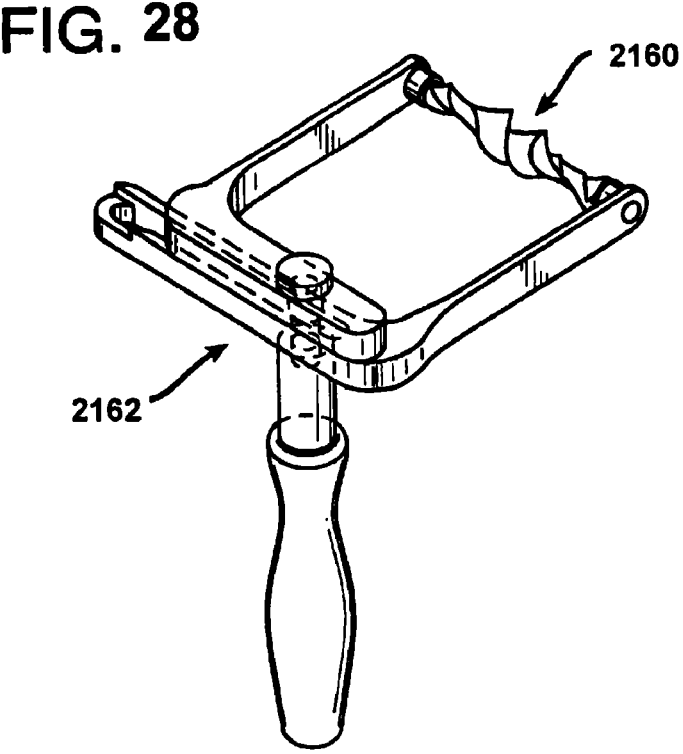
FIG. 28 is a perspective view of a cutting tool and handle wherein the cutting tool has a curvilinear profile.
Figure 29:
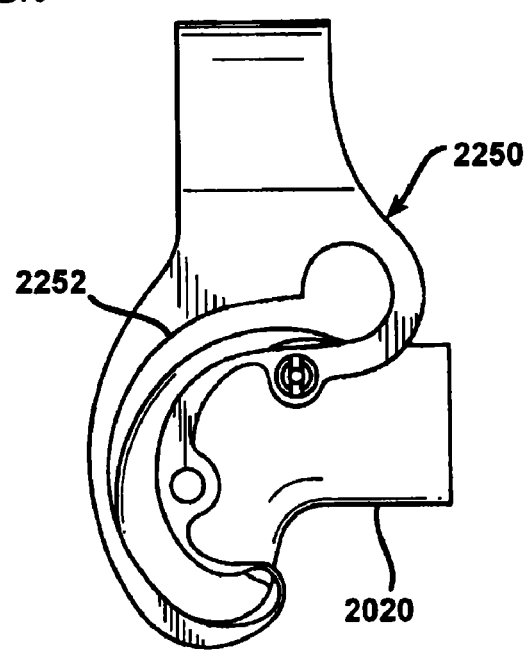
FIG. 29 is a side view of a cutting guide having a curved cutting path attached to a femur to be resected.
Figure 30:
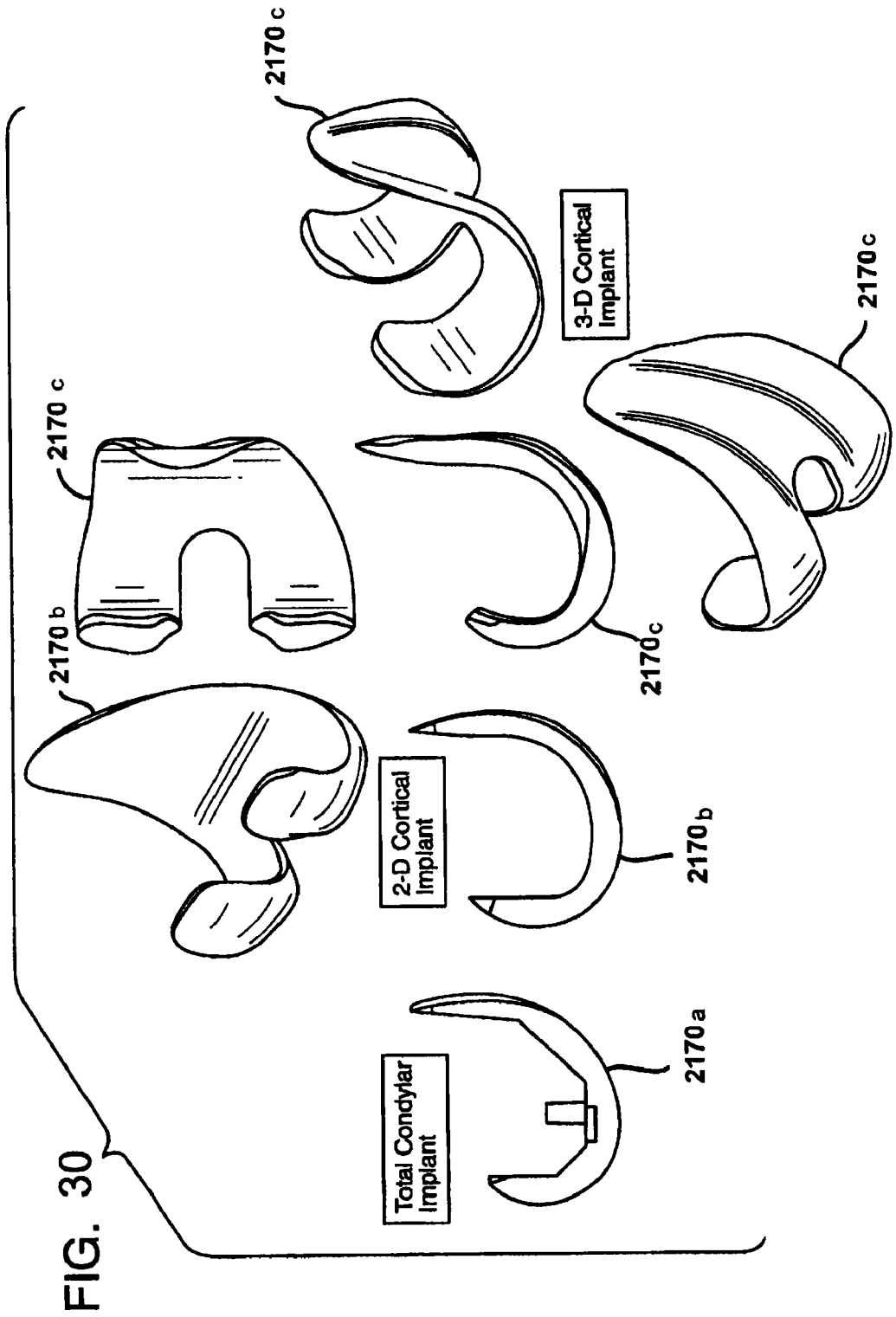
FIG. 30 shows a number of perspective and side views of implants having curved attachment faces, including a total condylar implant, a 2-D cortical implant and a 3-D cortical implant.

FIG. 28 shows a milling tool 2160 and handle 2162 wherein the cutting blade has a curvilinear profile instead of a linear profile. This allows for shaping the profile of the resection. FIG. 29 shows a cutting guide 2250 with a curved cutting path 2252, so that a curved cutting path can be used to resect the femur. Using the cutting guide 2250 with the curved cutting path 2252, together with the curvilinear profile milling tool 2160 shown in FIG. 28 allows for the resected femur 2020 to have a curved profile and a curved path. Shown in FIG. 30 are examples of a cortical femoral components 2170 with linear paths, with curved and linear paths, with curved paths, and with curved paths and curved profiles, including a total condylar implant 2170a, a 2-D cortical implant 2170b and a 3-D cortical implant 2170c. As can be seen in the figure, the anterior contact surface of the 3-D cortical implant has a mediolateral profile and cross-section normal to a mediolateral direction defining an anterior fixation path and at least a portion of the anterior fixation path can have a linear profile and no portion of the anterior fixation path converges proximally when viewed in a mediolateral direction, the posterior contact surface has a mediolateral profile and cross-section normal to the mediolateral direction defining a posterior fixation path, a profile of the anterodistal contact surface can be curved when viewed in a mediolateral direction, and the posterior fixation path of the posterior contact surface and the anterior fixation path of the anterior contact surface converge toward one another and intersect at a point proximal of the distal contact surface when viewed as projected on a plane defined normal to the mediolateral direction. As can also be seen in the figure, the anterior fixation path can be configured to diverge proximally away from the long axis of the femur and the posterior fixation path can be configured to converge proximally toward the long axis of the femur when viewed in the mediolateral direction.

Figure 33:
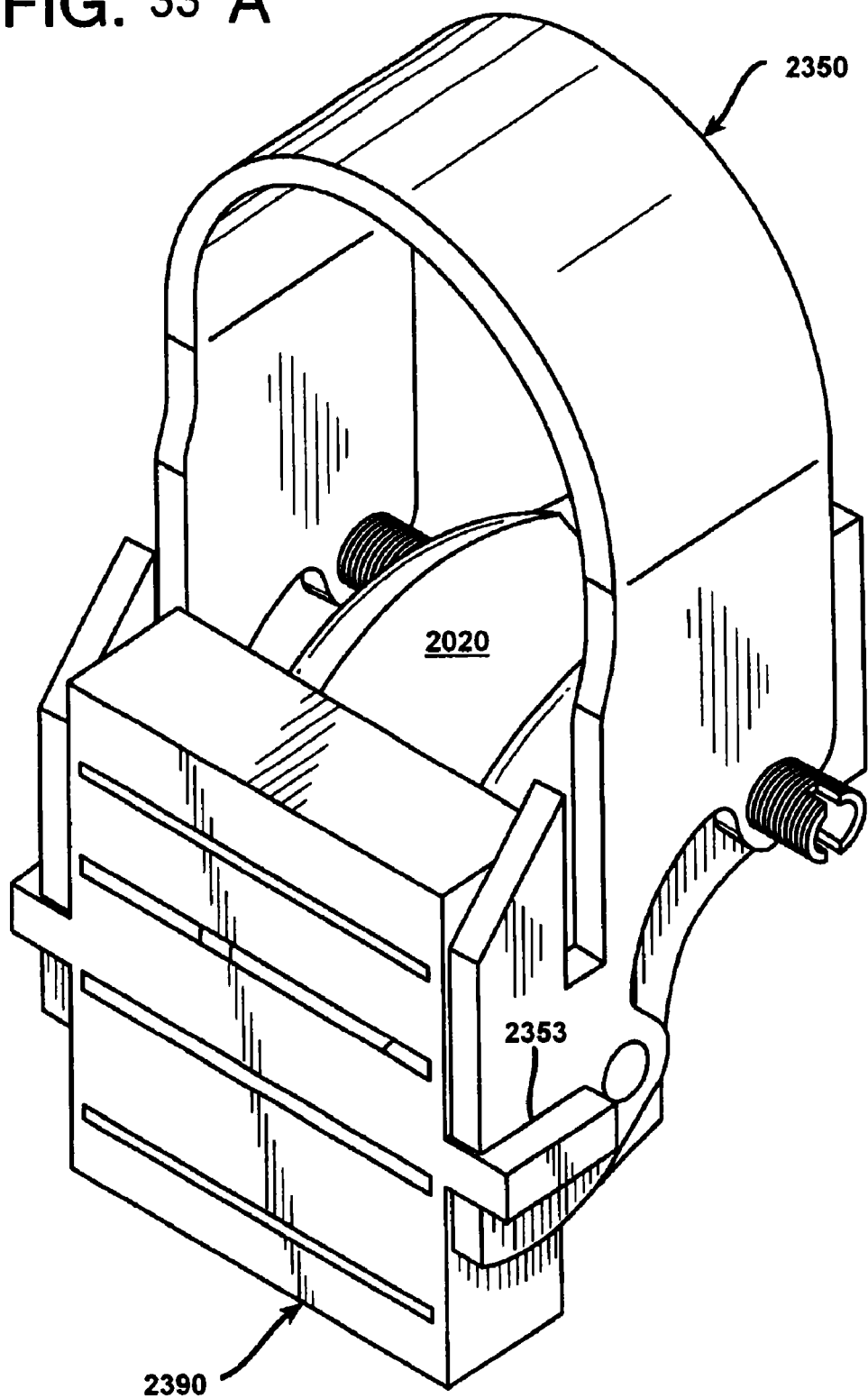
FIG. 33A is a perspective view of a cutting block interconnected with the cutting guide shown in FIG. 32, and FIGS. 33B and 33C are side and front views thereof.
Figure 33:
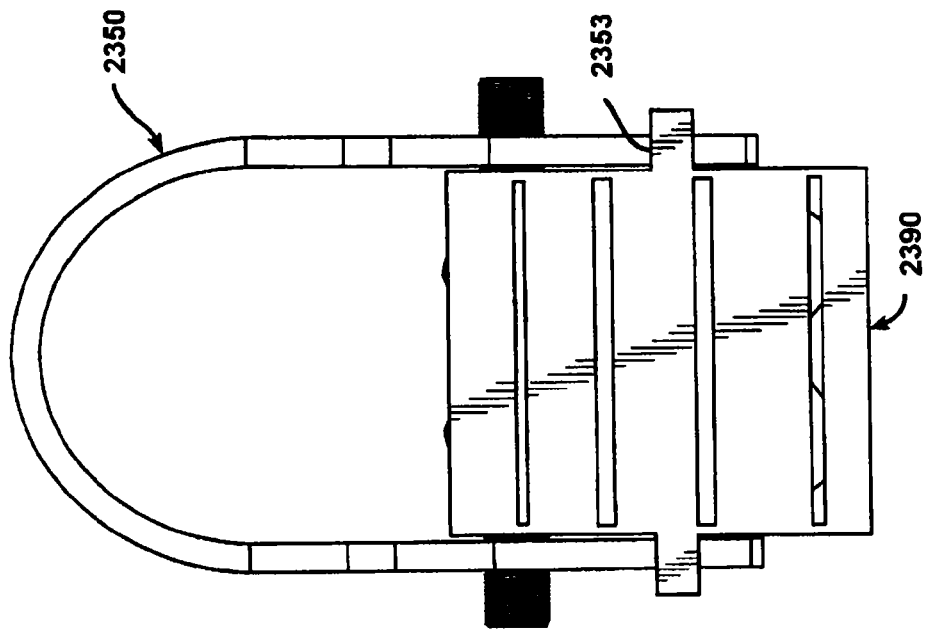
Figure 33:
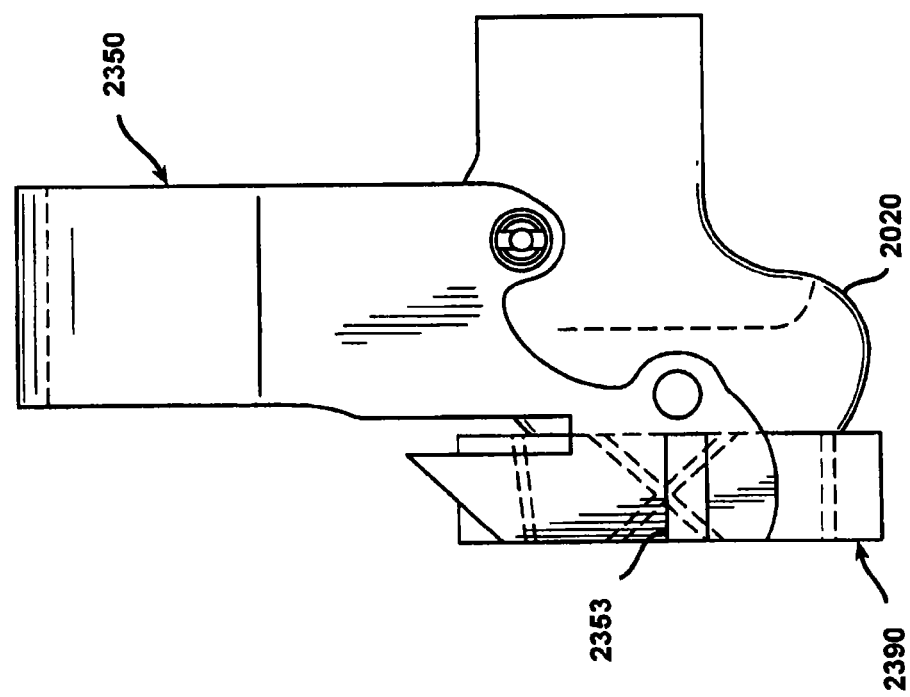

Referring now to FIGS. 31-33, it can be seen that similar techniques can be applied to the use of an oscillating sawblade and a conventional cutting block. FIGS. 31A and 31B show a modified cutting guide 2350 attached to the distal femur 2020 in a manner similar to the milling cutting guide 2150 shown in FIG. 27. FIGS. 32A and 32B show a distal resection cutting guide 2380 being attached to the cutting guide 2350 by positioning the distal resection cutting guide 2380 in slot 2351. An oscillating saw is inserted into the slot 2382 of the distal resection cutting guide 2380 and the distal resection is completed. As shown in FIGS. 33A, 33B and 33C, after the completion of the distal resection and removal of the distal resection cutting guide 2380, a 4 in 1 cutting guide block 2390 can be inserted into slot 2353 until it contacts the distal resection surface of the femur 2020. The remaining femoral resections could then be completed as is known in the art. This technique provides and advantage over other 5 in 1 oscillating sawblade techniques in two ways. First, the accuracy of cutting guide placement in significantly improved and second, the leading edges of the sawblade slots in the cutting guides may be brought into direct contact with the bone to be cut thus avoiding excessive cantilevering of the sawblade resulting in sub-optimal cuts.

Figure 24:
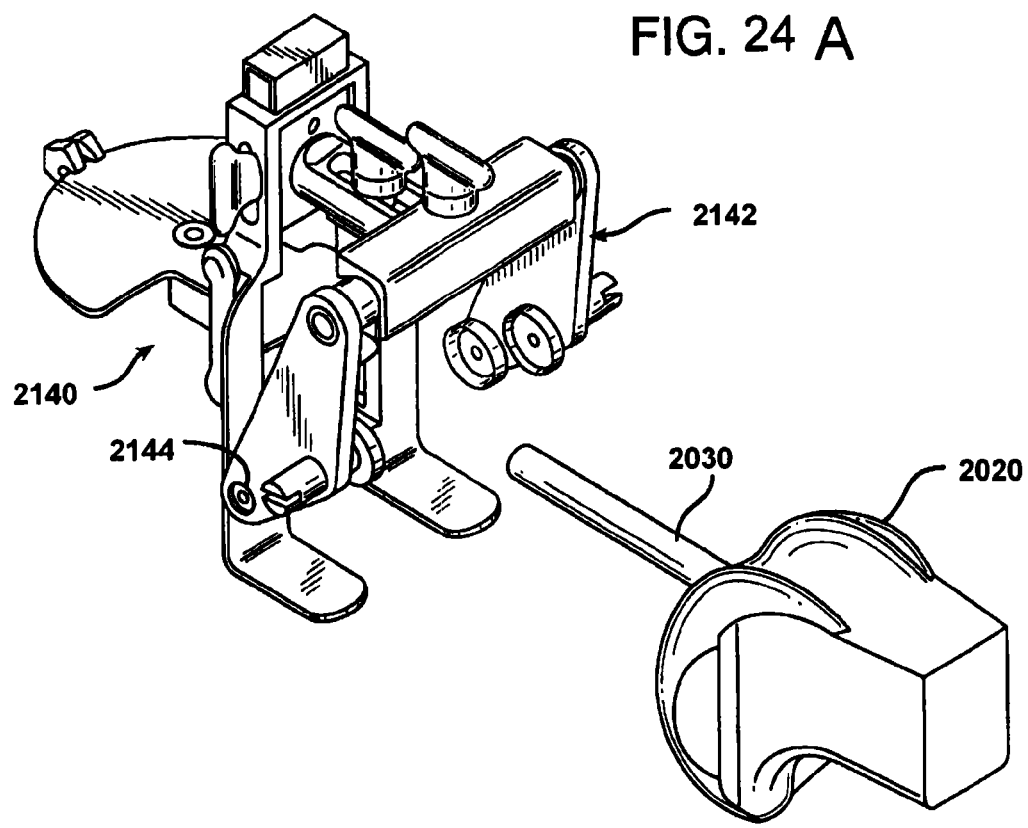
FIG. 24A is a perspective view of the positioning and drill guide apparatus of the present invention, along with a femur to be resected having a intramedullary rod inserted therein.
FIG. 24B is a side view thereof.
Figure 25:
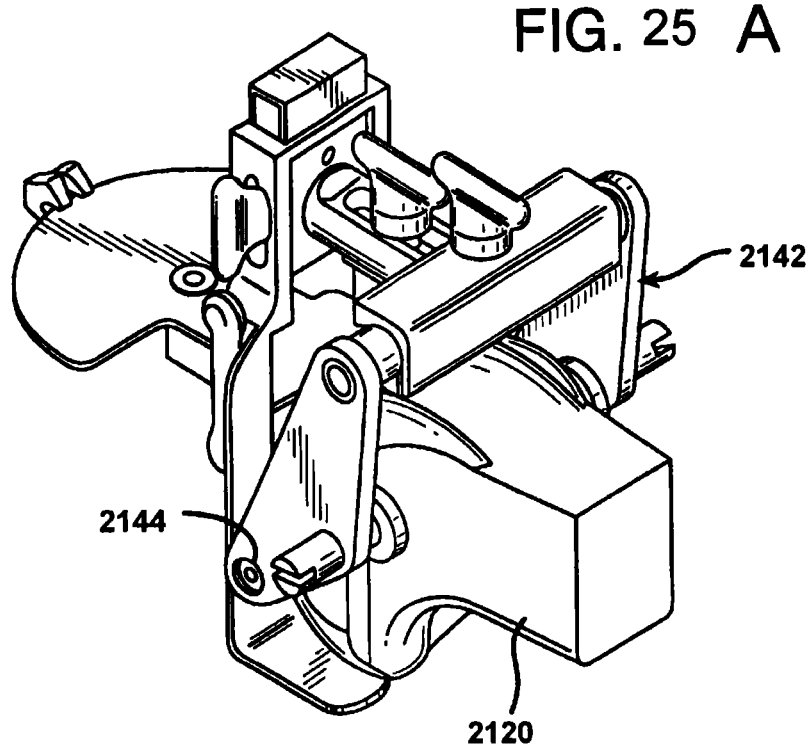
FIG. 25A is a perspective view of the positioning and drill guide apparatus shown in FIG. 24 positioned on a femur to be resected.
FIG. 25B is a side view thereof.
Figure 25:
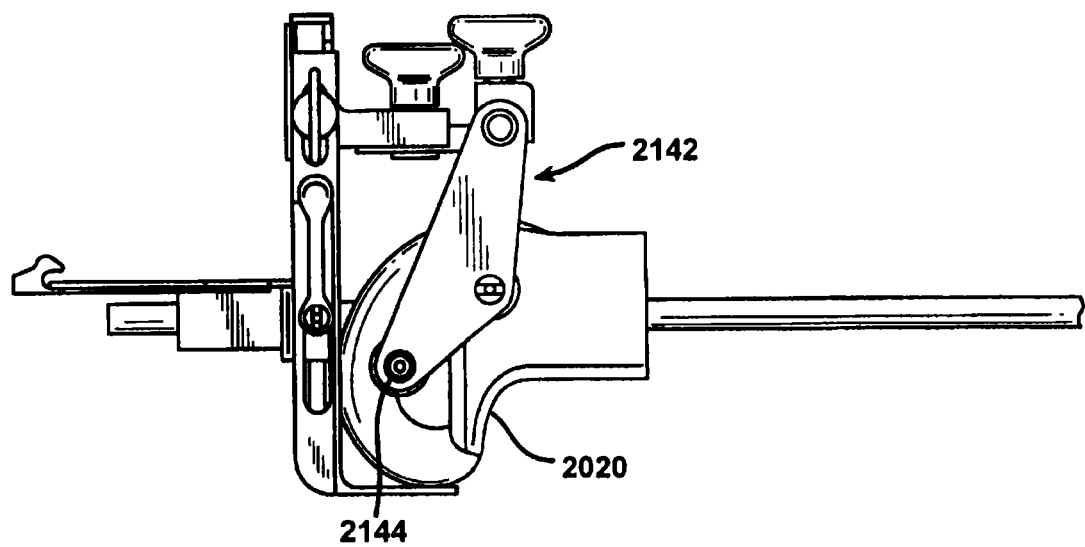
Figure 34:
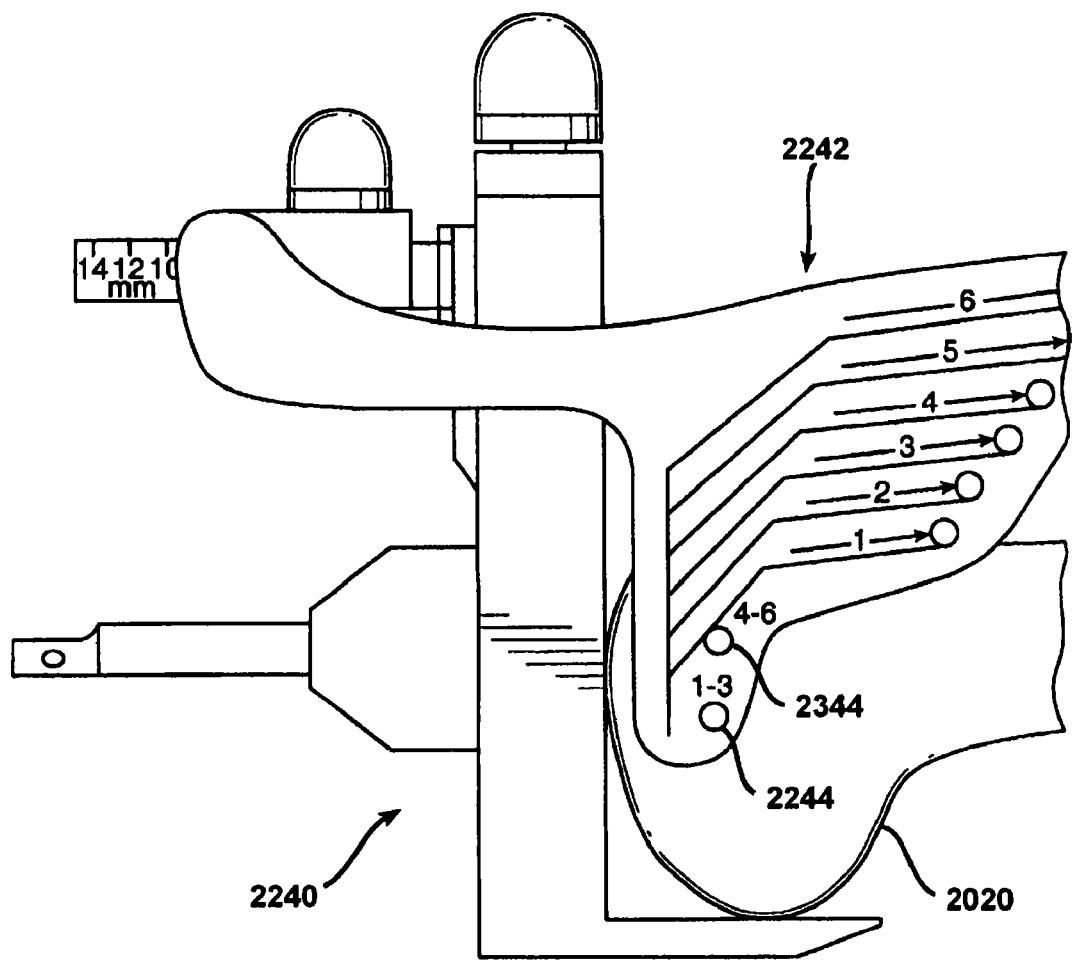
FIG. 34 is a side view of the positioning and drill guide apparatus shown in FIG. 34 showing size markings thereon.
Figure 35:
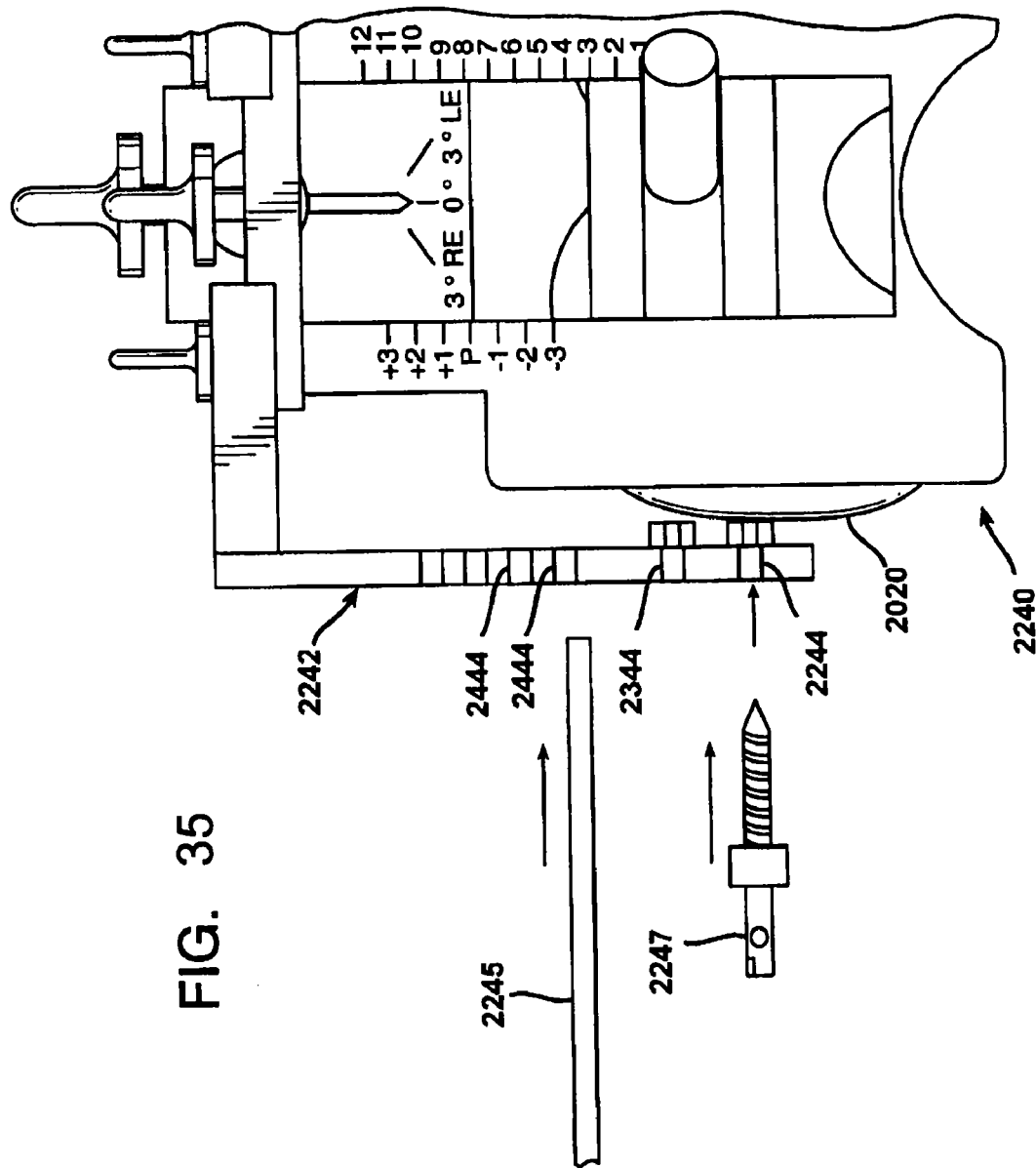
FIG. 35 is a back view thereof.

FIG. 34 is a close up side view of the alignment guide and drill guide shown in FIG. 24. The alignment guide 2240 interconnects with the drill guide 2242. The drill guide includes a plurality of drill hole locators 2244, 2344 and size markings. FIG. 35 is a back view of the alignment guide 2024 and drill guide 2242 shown in FIG. 34. Also shown in FIG. 35 are drill hole locators 2244, 2344, fixation drill 2247 and sizing rod 2245 for extending through sizing apertures 2444. The sizing rod 2245 can be placed from the medial side of the femur to the lateral side in the exact position of the anterior-most tip of the implant corresponding to the size intended for that hole. In this way, the drill holes for cutting guide placement are directly linked to the anterior size reference and the alignment guides reference of the posterior condyles thus minimizing any form of tolerance stacking and allowing for the easy implementation of simultaneous anterior and posterior referencing and adjustment.

Figure 36:
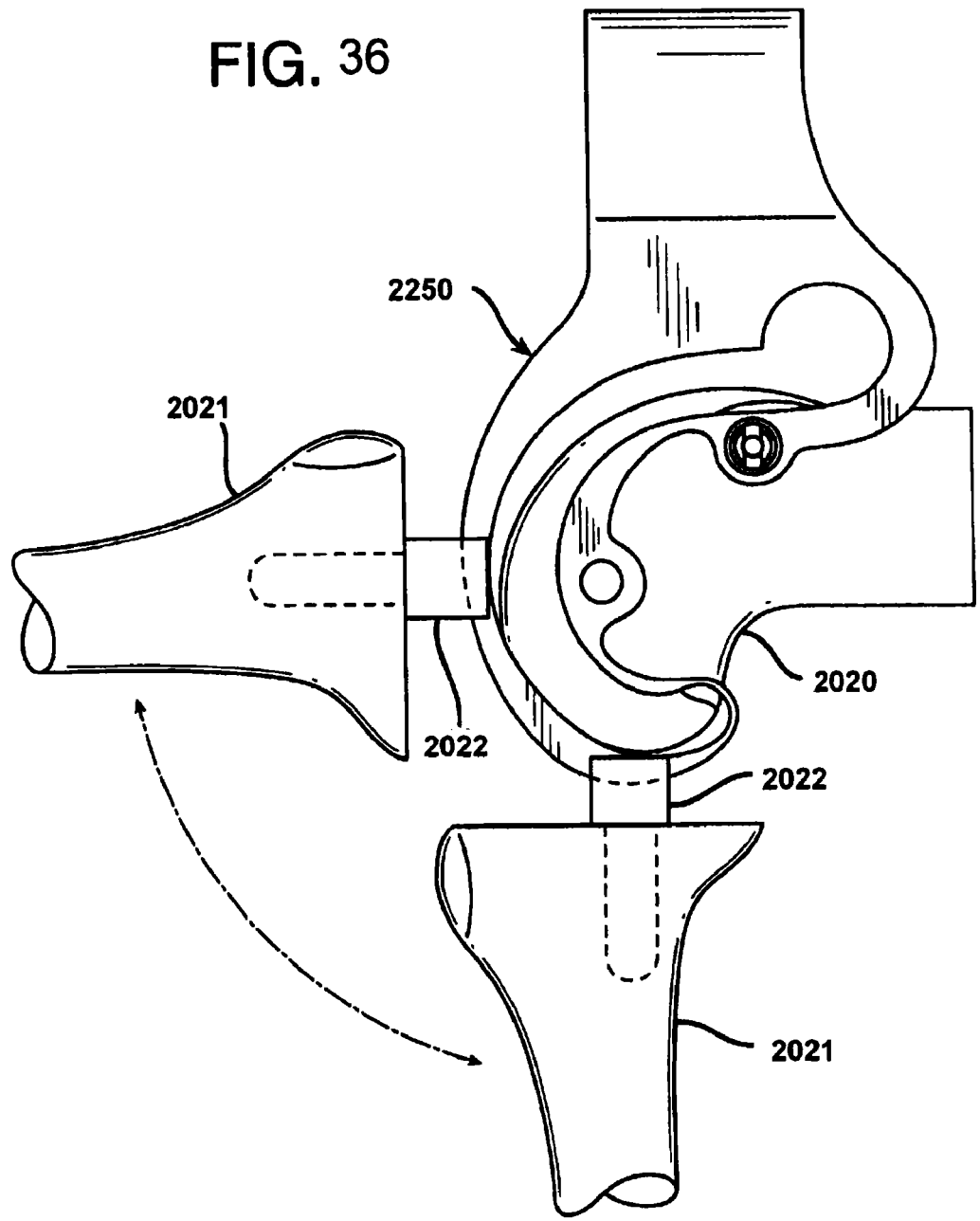
FIG. 36 is a side view of the cutting guide having a curved cutting path shown in FIG. 29 used in connection with ligament balancing.
Figure 37:
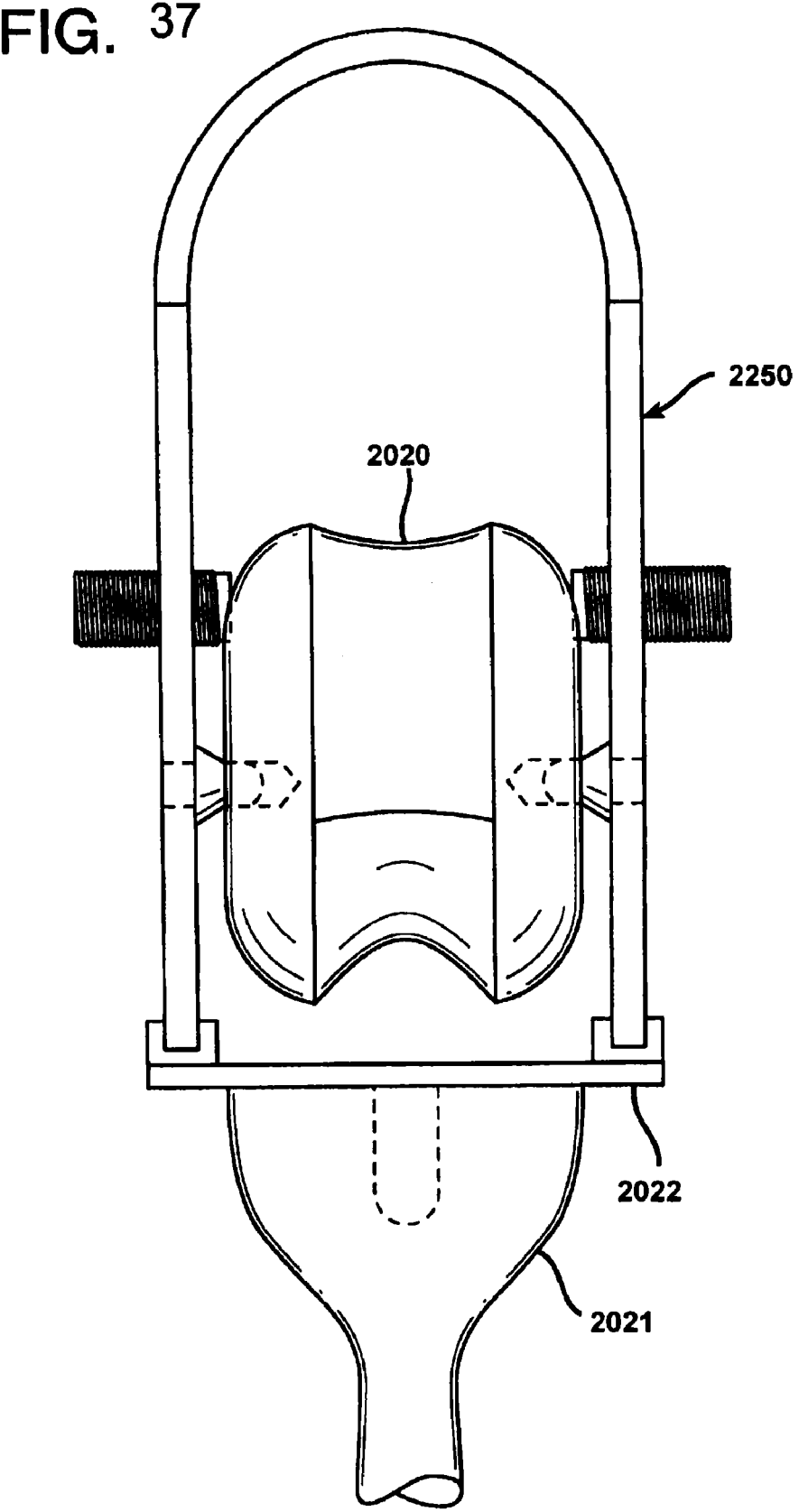
FIGS. 37 and 38 are front and perspective views thereof.
Figure 38:
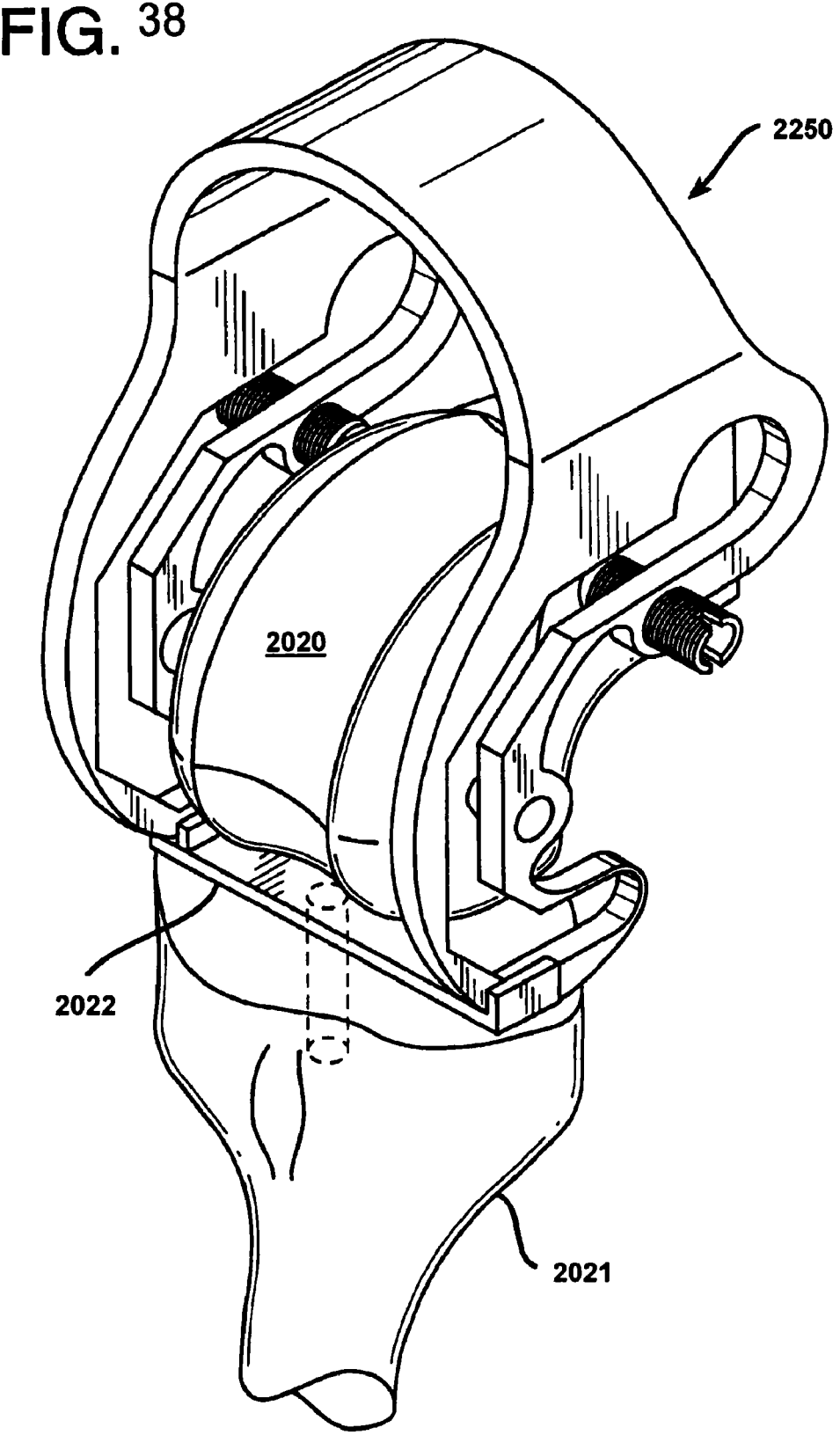

FIGS. 36-38 relate to method of ligament balancing using the cutting guide 2250 shown in FIG. 29. Soft tissue balancing for TKA is considered to be crucial in the use of mobile bearing designs. The re-popularization of this technique has spurred the development and commercialization of some very intricate instrumentation systems that are very prone to surgeon misuse due to their complexity. Another drawback of these systems is that they balance the tissues in flexion and extension, but do not allow continuous reference of the soft tissue balance throughout the range of motion similar to that achieved by trial reduction. By creating the edges of the cutting guide 2250 (or even a trailing guide including no cutting guide or cutting guide attachment features) in a profile or geometry that simulates the geometry of the implant and having that geometry act or articulate with a referencing means on the cut proximal tibia 2021 and reference bar 2022 attached thereto, an effective trial reduction of soft tissue balance may be attained prior to any femoral resection.

Figure 39:
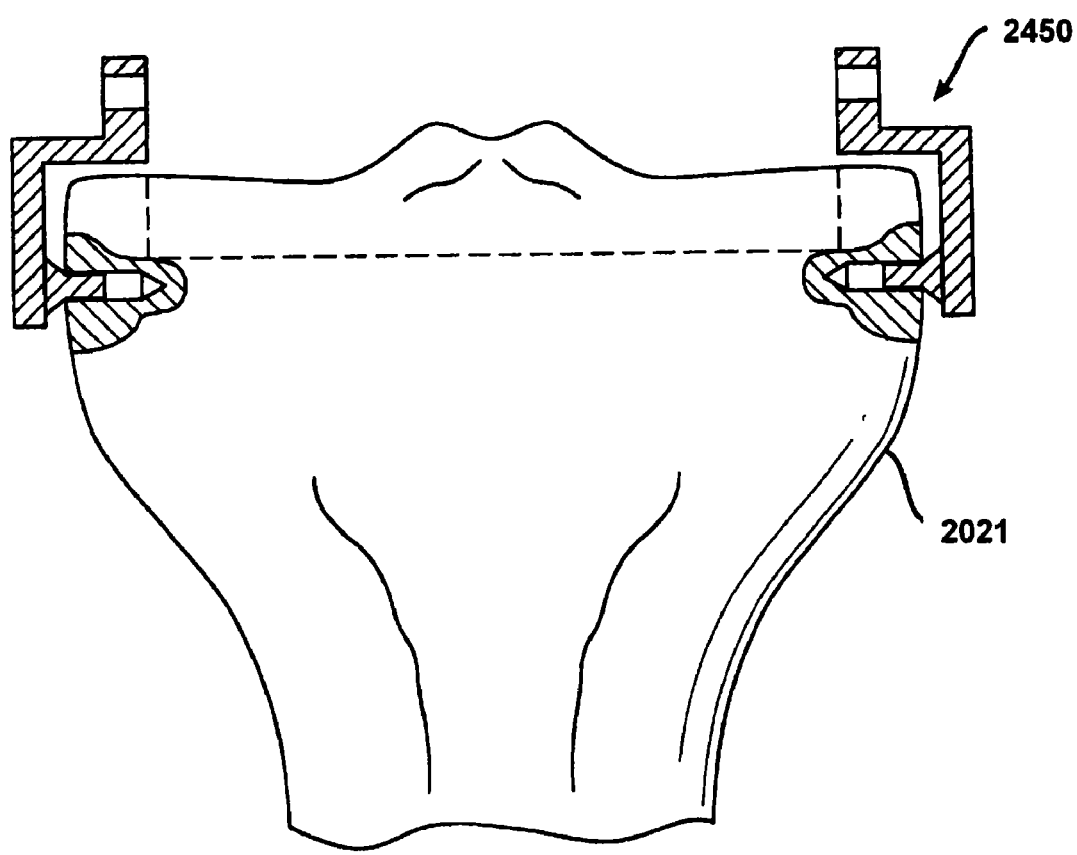
FIGS. 39 and 40 are front and side views of a cutting guide attached to a tibia.
Figure 40:
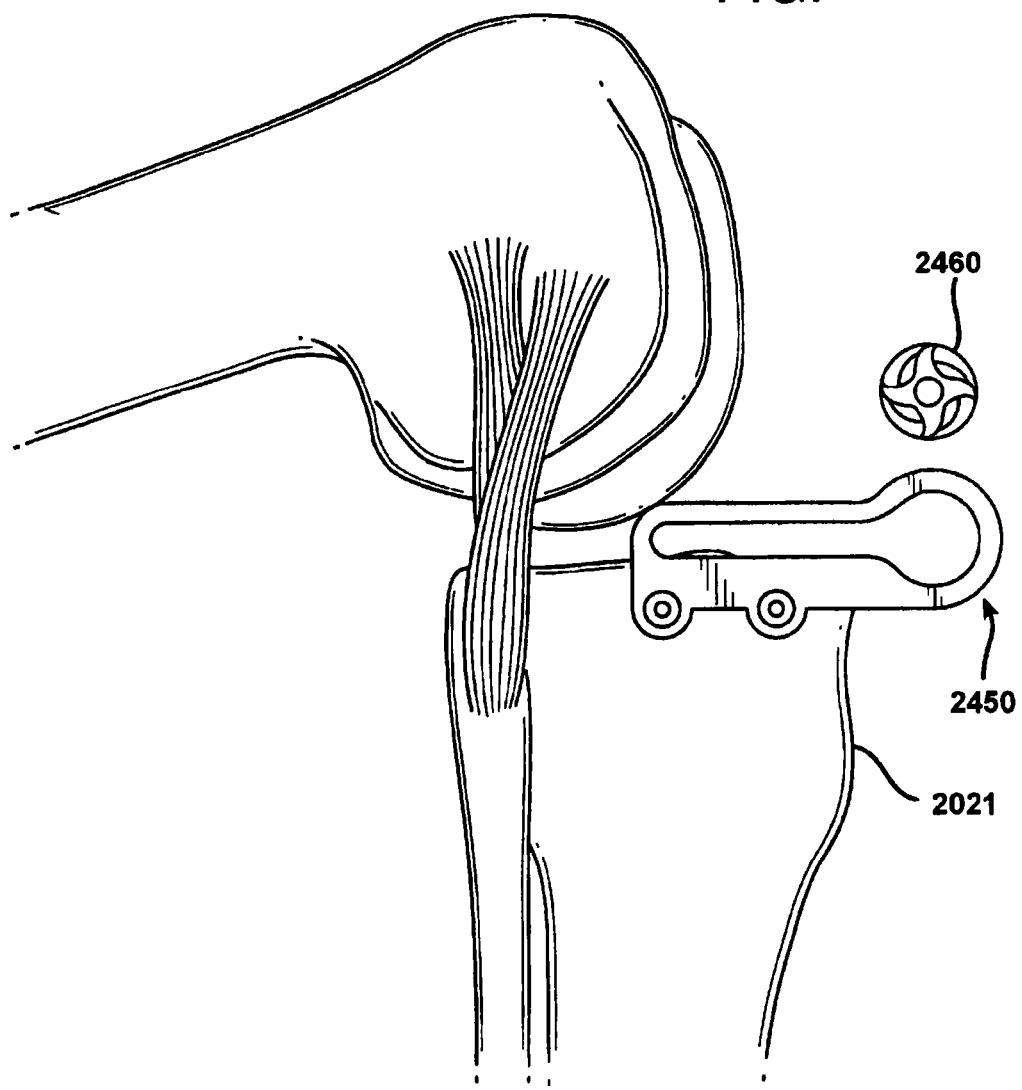

The cutting guide surfaces of the cutting guide need not be coplanar with the surfaces to be created in a bone, but may instead be parallel, but offset. Also the cutting guides may be located over the surfaces of the bone to be cut, but not necessarily located about the sides of the entire bone to be cut. As shown in FIG. 39 a cutting guide 2450 may be applied to the tibia or other bones. In addition, the cutting guide shown in FIGS. 39 and 40 is intentional depicted as only being capable of completing the anterior portion of the tibial resection; this is intended to demonstrate that, when planar cuts are desired, the milled surface can be used to guide the remaining resection of an oscillating sawblade thus preserving the accuracy of the milling technique while minimizing the precision errors of the oscillating sawblade.

Modifications of the foregoing may be made without departing from the spirit and scope of the invention.

What is desired to be protected by Letters Patents is set forth in the appended claims:

1. A femoral prosthetic implant for attachment to a femur during a knee arthroplasty procedure, the femur having a long axis, the implant comprising:
an outer bearing surface having a condylar portion and a patellofemoral portion;
an inner bone contact surface in back to back disposition with the outer bearing surface, the inner bone contact surface including a posterior contact surface and an anterior contact surface configured to contact geometrically corresponding bone cuts in the femur and a distal contact surface, and
at least one inwardly protruding structure formed unitarily with the implant with at least one bone contacting surface extending in both an anterior to posterior direction and inwardly of the inner bone contact surface to provide medial-lateral fixation stability between the implant and the femur, and
wherein:
the anterior contact surface has a profile viewed in a mediolateral direction defining an anterior fixation path that is configured to diverge proximally away from the long axis of the femur and at least a portion of which has a linear profile when viewed in the mediolateral direction;
no portion of the anterior fixation path is configured to converge proximally toward the long axis of the femur when viewed in the mediolateral direction;
the posterior contact surface has a profile viewed in the mediolateral direction defining a posterior fixation path that is configured to converge proximally toward the long axis of the femur;
the posterior fixation path of the posterior contact surface and the anterior fixation path of the anterior contact surface converge toward one another proximally of the distal contact surface when viewed as projected on a plane defined normal to the mediolateral direction; and
the implant is configured to fit a femur having a posterior cut surface and an anterior cut surface defining cutting paths that converge proximally towards each other.

2. The implant of claim 1, wherein the implant is at least partially constructed of a ceramic material.

3. The implant of claim 1, wherein the at least one inwardly protruding structure forms a bulge.

4. The implant of claim 3, wherein the at least one inwardly protruding structure extends in the anterior to posterior direction at least along a portion of the inner bone contact surface corresponding to at least one of at least a portion of an antero-distal, a distal, or a posterodistal resected surface.

5. The implant of claim 1, wherein the at least one inwardly protruding structure is comprised of a plurality of fin-like structures.

6. A femoral prosthetic implant for attachment to a femur during a knee arthroplasty procedure, the femur having a long axis, the femoral implant comprising:
an outer bearing surface having a condylar portion and a patellofemoral portion;
an inner bone contact surface in back to back disposition with the outer bearing surface, the inner bone contact surface including a posterior contact surface, a distal contact surface, and an anterior contact surface configured to contact geometrically corresponding bone cuts in the femur, the inner bone contact surface having a mediolaterally extending fixation profile corresponding to a mediolaterally extending resection profile of cut surfaces on the femur, a portion of the fixation profile including a continuous, non-colinear cross-section including at least partially anterior to posterior extending bone facing elements configured to provide medial-lateral fixation stability between the implant and the femur by a material interference between the resected bone and the inner bone contact surface, and wherein:
the anterior contact surface has a cross-section normal to a mediolateral direction defining an anterior fixation path that is configured to diverge proximally away from the long axis of the femur with no portion configured to converge proximally toward the long axis of the femur when viewed in the mediolateral direction;
the posterior contact surface has a cross-section normal to the mediolateral direction defining a posterior fixation path that is configured to converge proximally toward the long axis of the femur;
the posterior fixation path of the posterior contact surface and the anterior fixation path of the anterior contact surface converge toward one another and intersect at a point proximal of the distal contact surface when viewed as projected on a plane defined normal to the mediolateral direction; and
the implant is configured to fit a femur having a posterior cut surface and an anterior cut surface defining cutting paths that converge proximally towards each other.

7. The implant of claim 6, wherein the implant is at least partially constructed of a ceramic material.

8. The implant of claim 6, wherein the bone facing elements form a bulge.

9. The implant of claim 3 or 8, wherein the bulge defines a curved fixation profile.

10. The implant of claim 3 or 8, wherein the bulge is configured to fit a femur having at least a portion of a distal cut surface at least partially formed by a milling tool.

11. The implant of claim 8, wherein the bone facing elements extend in an anterior to posterior direction at least along a portion of the inner bone contact surface corresponding to at least one of at least a portion of an anterodistal, a distal, or a posterodistal resected surface.

12. The implant of claim 4 or 11, wherein at least one of at least a portion of an anterodistal, a distal or a posterodistal resected surface includes at least two of the surfaces.

13. The implant of claim 6, wherein the bone facing elements are comprised of a plurality of fin-like structures.

14. The implant of claim 5 or 13, wherein the fin-like structures correspond to resected surfaces at least partially formed by a milling tool.

15. The implant of claim 1 or 6, wherein at least one of the anterior fixation path and the posterior fixation path define one of a line or a curve or a combination thereof.

16. The implant of claim 1 or 6, wherein at least one of an anterior fixation profile and a posterior fixation profile define one of a line or a curve or a combination thereof.

17. A system for use in a knee arthroplasty procedure, comprising:
a femoral prosthetic implant for attachment to a femur during the knee arthroplasty procedure, the femur having a long axis, the femoral implant comprising:
an outer bearing surface having a condylar portion and a patellofemoral portion;
an inner bone contact surface in back to back disposition with the outer bearing surface, the inner bone contact surface including a posterior contact surface, and an anterior contact surface configured to contact geometrically corresponding bone cuts in the femur and a distal contact surface, and
at least one inwardly protruding structure formed unitarily with the implant with at least one bone contacting surface extending in both an anterior to posterior direction and inwardly in the inner bone contact surface to provide medial-lateral fixation stability between the implant and the femur, and wherein:
the anterior contact surface has a profile viewed in a mediolateral direction defining an anterior fixation path that is configured to diverge proximally away from the long axis of the femur and at least a portion of which has a linear profile when viewed in the mediolateral direction;
no portion of the anterior fixation path is configured to converge proximally toward the long axis of the femur when viewed in the mediolateral direction;
the posterior contact surface has a profile viewed in the mediolateral direction defining a posterior fixation path that is configured to converge proximally toward the long axis of the femur;
the posterior fixation path of the posterior contact surface and the anterior fixation path of the anterior contact surface converge toward one another proximally of the distal contact surface when viewed as projected on a plane defined normal to the mediolateral direction; and
the femoral implant is configured to fit a femur having a posterior cut surface and an anterior cut surface defining cutting paths that converge proximally towards each other; and
a tibial prosthetic implant for attachment to a resected surface of a tibia during the knee arthroplasty procedure, the tibial implant having an articular surface for articulating with respect to the outer bearing surface of the femoral implant and a bone contact surface for contacting a resected surface of the tibia.

18. The system of claim 17, wherein the at least one inwardly protruding structure of the femoral implant forms a bulge.

19. The system of claim 18, wherein the at least one inwardly protruding structure of the femoral implant extends in the anterior to posterior direction at least along a portion of the inner bone contact surface corresponding to at least one of at least a portion of an anterodistal, a distal, or a posterodistal resected surface.

20. The system of claim 17, wherein the at least one inwardly protruding structure of the femoral implant is comprised of a plurality of fin-like structures.

21. A system for use in a knee arthroplasty procedure, comprising:
a femoral prosthetic implant for attachment to a femur during the knee arthroplasty procedure, the femur having a long axis, the femoral implant comprising:
an outer bearing surface having a condylar portion and a patellofemoral portion;
an inner bone contact surface in back to back disposition with the outer bearing surface, the inner bone contact surface including a posterior contact surface, a distal contact surface, and an anterior contact surface configured to contact geometrically corresponding bone cuts in the femur, the inner bone contact surface having a mediolaterally extending fixation profile corresponding to a mediolaterally extending resection profile of cut surfaces on the femur, a portion of the fixation profile including a continuous, non-colinear cross-section including at least partially anterior to posterior extending bone facing elements configured to provide medial-lateral fixation stability between the implant and the femur by a material interference between the resected bone and the inner bone contact surface, and
wherein:

the anterior contact surface has a cross-section normal to a mediolateral direction defining an anterior fixation path that is configured to diverge proximally away from the long axis of the femur with no portion configured to converge proximally toward the long axis of the femur when viewed in the mediolateral direction;

the posterior contact surface has a cross-section normal to the mediolateral direction defining a posterior fixation path that is configured to converge proximally toward the long axis of the femur;

the posterior fixation path of the posterior contact surface and the anterior fixation path of the anterior contact surface converge toward one another and intersect at a point proximal of the distal contact surface when viewed as projected on a plane defined normal to the mediolateral direction; and the femoral implant is configured to fit a femur having a posterior cut surface and an anterior cut surface defining cutting paths that converge proximally towards each other; and a tibial prosthetic implant for attachment to a resected surface of a tibia during the knee arthroplasty procedure, the tibial implant having an articular surface for articulating with respect to the outer bearing surface of the femoral implant and a bone contact surface for contacting a resected surface of the tibia.

22. The system of claim 17 or 21, wherein the femoral implant is at least partially constructed of a ceramic material.

23. The system of claim 21 wherein the bone facing elements of the femoral implant form a bulge.

24. The system of claim 18 or 23, wherein the bulge defines a curved fixation profile.

25. The system of claim 18 or 23, wherein the bulge is configured to fit a femur having at least a portion of a distal cut surface at least partially formed by a milling tool.

26. The system of claim 23, wherein the bone facing elements of the femoral implant extend in an anterior to posterior direction at least along a portion of the inner bone contact surface corresponding to at least one of at least a portion of an anterodistal, a distal, or a posterodistal resected surface.

27. The system of claim 19 or 26, wherein at least one of at least a portion of an anterodistal, a distal or a posterodistal resected surface includes at least two of the surfaces.

28. The system of claim 21, wherein the bone facing elements of the femoral implant are comprised of a plurality of fin-like structures.

29. The system of claim 20 or 28, wherein the fin-like structures correspond to resected surfaces at least partially formed by a milling tool.

30. The system of claim 17 or 21, wherein at least one of the anterior fixation path and the posterior fixation path define one of a line or a curve or a combination thereof.

31. The system of claim 17 or 21, wherein at least one of an anterior fixation profile and a posterior fixation profile define one of a line or a curve or a combination thereof.

32. The system of claim 17 or 21, further comprising a patellar prosthetic implant that cooperates with the femoral implant and the tibial implant.

33. The system of claim 17 or 21, wherein the articular surface of the tibial implant and the bone contact surface of the tibial implant are a unitary construct.

* * * * *

UNITED STATES PATENT AND TRADEMARK OFFICE
CERTIFICATE OF CORRECTION

| | | |
|---|---|---|
| PATENT NO. | : 8,088,167 B2 | Page 1 of 1 |
| APPLICATION NO. | : 12/638692 | |
| DATED | : January 3, 2012 | |
| INVENTOR(S) | : Haines | |

It is certified that error appears in the above-identified patent and that said Letters Patent is hereby corrected as shown below:

Page 1, (75) Inventor: Please replace "Timothy G. Haines, Columbia City, IN (US)" with "Timothy G. Haines, Seattle, WA (US)"

Column 24, Lines 66-67, replace "resected bone" with "femur"

Column 26, Line 65, replace "resected bone" with "femur"

Column 28, Line 28, remove "and the tibial implant"

Signed and Sealed this
Tenth Day of April, 2012

David J. Kappos
*Director of the United States Patent and Trademark Office*